United States Patent [19]

Miura et al.

[11] Patent Number: 5,032,165
[45] Date of Patent: Jul. 16, 1991

[54] 3-(SUBSTITUTED PHENYL)PYRAZOLE DERIVATIVES, SALTS THEREOF, AND HERBICIDES THEREFROM

[75] Inventors: Yuzo Miura, Nishinomiya; Tsutomu Mabuchi, Kawachinagano; Mitsuru Kajioka, Sakai; Isao Yanai, Osakasayama, all of Japan

[73] Assignee: Nihon Nohyaku Company, Ltd., Tokyo, Japan

[21] Appl. No.: 400,791

[22] Filed: Aug. 30, 1989

[30] Foreign Application Priority Data

Aug. 31, 1988 [JP] Japan .................................. 63-217164

[51] Int. Cl.$^5$ .................. C07D 231/20; C07D 401/06; C07D 413/06; A01N 43/56
[52] U.S. Cl. .......................................... 71/92; 71/86; 71/87; 546/14; 546/22; 546/211; 544/69; 544/140; 548/375; 548/377; 548/110; 548/119; 548/376
[58] Field of Search ................. 71/92, 86, 87; 546/14; 544/69; 548/375, 119, 376

[56] References Cited

U.S. PATENT DOCUMENTS

| | | | |
|---|---|---|---|
| 4,008,249 | 2/1977 | Fischer et al. | 548/377 |
| 4,260,775 | 4/1981 | Plath et al. | 548/377 |
| 4,298,749 | 11/1981 | Plath et al. | 548/377 |
| 4,316,039 | 2/1982 | Plath et al. | 548/377 |
| 4,316,040 | 2/1982 | Plath et al. | 548/377 |
| 4,354,031 | 10/1982 | Plath et al. | 548/377 |
| 4,424,363 | 1/1984 | Plath et al. | 548/362 |

FOREIGN PATENT DOCUMENTS

| | | |
|---|---|---|
| 0052333 | 5/1982 | European Pat. Off. . |
| 1488285 | 2/1975 | United Kingdom . |
| 2073172 | 4/1980 | United Kingdom . |

*Primary Examiner*—John M. Ford
*Attorney, Agent, or Firm*—Cushman, Darby & Cushman

[57] ABSTRACT

There are disclosed a (3-substituted phenyl)pyrazole derivative represented by the general formula

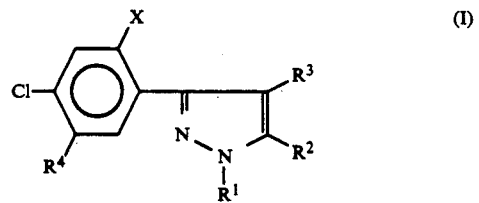

(I)

wherein $R^1$, $R^2$, $R^3$, $R^4$ and X are various substituents and a salt thereof, and its production process. Said pyrazole derivative or its salt is useful as a herbicide for controlling various injurious weeds.

20 Claims, No Drawings

3-(SUBSTITUTED PHENYL)PYRAZOLE DERIVATIVES, SALTS THEREOF, AND HERBICIDES THEREFROM

The present invention relates to 3-(substituted phenyl)pyrazole derivatives or salts thereof, a process for producing said derivatives or salts, and to herbicidal compositions comprising said derivatives or salts and methods for applying said herbicidal compositions. The 3-(substituted phenyl)pyrazole derivatives are represented by the general formula

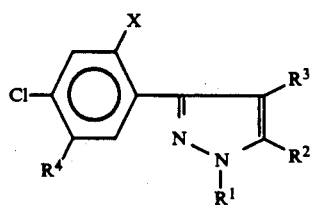

wherein,

X denotes halogen, $R^1$ denotes lower alkyl or lower haloalkyl, $R^2$ denotes —A—$R^5$ wherein, $R^5$ denotes hydrogen, lower alkyl or lower haloalkyl and A denotes —O— or —S—, $R^3$ denotes hydrogen or halogen, and $R^4$ denotes formyl, nitro, —CO—B—$R^6$ [wherein, B denotes —O—, —S—, or —$NR^7$ and $R^6$ and $R^7$ are the same or different and each denote hydrogen, lower alkyl, lower alkenyl, lower alkynyl, lower alkoxycarbonylalkyl, cycloalkyl, lower alkylsulfonyl, lower alkoxyalkyl, or di(lower alkoxy)phosphinylalkyl and when B is —O—, $R^6$ can be an alkali metal atom or a quaternary ammonium salt], —D—$R^8$ [wherein, D denotes —O—, —S(O)n (n being an integer of 0 to 2), or —$NR^9$— and $R^8$ and $R^9$ are the same or different and each denote; hydrogen; alkyl; haloalkyl; lower alkenyl; lower haloalkenyl; lower alkynyl; lower cyanoalkyl; lower cycloalkyl; lower alkoxyalkyl; lower alkylthioalkyl; lower alkoxyalkoxyalkyl; lower alkylsulfonyl; di(lower alkyl)aminosulfonyl; aminosulfonyl having one or more substituents which are the same or different and selected from hydrogen, lower alkynyl and lower alkyl; phenylalkyl or phenoxyalkyl optionally having, on the phenyl ring, one or more substituents which are the same or different and selected from halogen, lower alkyl, lower haloalkyl, and lower alkoxy; tri(lower alkyl)silylalkyl; or di(lower alkoxy)phosphinylalkyl]; or —$(CHR^{10})_m$—CO—E—$R^{12}$ [wherein, E denotes —O—, —S—, or —$NR^{11}$— wherein $R^{11}$ is as defined below, $R^{10}$ denotes hydrogen or lower alkyl, and $R^{11}$ and $R^{12}$ are the same or different and each denote; hydrogen; alkyl; haloalkyl; lower alkenyl; lower haloalkenyl; lower alkynyl; lower haloalkynyl; lower alkoxyalkyl; lower cycloalkyl; lower cyanoalkyl; lower alkylthioalkyl; lower alkoxyalkoxyalkoxy; tri(lower alkyl)silylalkyl; di(lower alkoxy)phosphinylalkyl; phenyl optionally having, on the phenyl ring, one or more substituents selected from halogen, lower alkyl, lower haloalkyl, and lower alkoxy; or phenylalkyl optionally having, on the phenyl ring, one or more substituents selected from halogen, lower alkyl, lower haloalkyl, and lower alkoxy; or $R^{11}$, jointly with $R^{12}$, forms piperidino or morpholino, and when E is —O—, $R^{12}$ can be an alkali metal atom or a quaternary ammonium salt; and m denotes an integer of 0 to 3)].

The present inventors made intensive studies in order to develop a novel herbicide and as a result have found that 3-(substituted phenyl)pyrazole derivatives represented by the above general formula (I) (hereinafter, simply referred to as formula (I)) and salts thereof are novel compounds, not yet written in literature, and they show excellent herbicidal effects on weeds even at lower dosages. Based on this finding, the present invention has been accomplished.

Prior to the present invention, compounds considered as analogous to the present inventive compounds were disclosed as herbicides in Japanese Patent Application Kokai Nos. Sho.50-117936, Sho.52-91861, Sho.54-70270, and Sho.55-9062 and in other literature. However, the present inventive 3-(substituted phenyl)pyrazole derivative represented by formula (I) or salts thereof have never been disclosed and show superior herbicidal effects at lower dosages than those where the compounds disclosed in the above patent applications do.

The present inventive 3-(substituted phenyl)pyrazole derivatives represented by formula (I) and salts thereof include structural isomers as shown below. These structural isomers form simultaneously in the production of 3-(substituted phenyl)pyrazole derivatives and each isomer can be isolated by a suitable separating method, e.g. recrystallization or column chromatography. The scope of the present invention also includes these structural isomers.

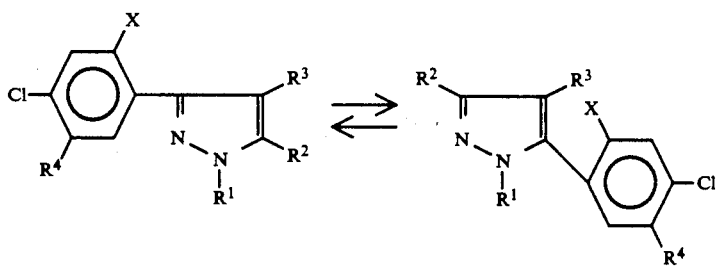

In this formula, $R^1$, $R^2$, $R^3$, $R^4$, and X are as defined above.

Certain compounds of the 3-(substituted phenyl)pyrazole derivatives represented by formula (I) have optical isomers, which are also included in the scope of the present invention.

The substituent $R^1$ in 3-(substituted phenyl)pyrazole derivatives represented by formula (I) and salts thereof can be exemplified by lower alkyl and lower haloalkyl groups, of which preferred are lower alkyls including methyl.

The substituent $R^2$ can be exemplified by hydroxy, mercapto, lower alkoxy, alkylthio, haloalkoxy, and haloalkylthio groups, of which preferred are haloalkoxy groups and particularly preferred is a difluoromethoxy group.

The substituent $R^3$ can be exemplified by hydrogen and halogen atoms, of which preferred are halogen atoms, particularly a chlorine atom.

The substituent $R^4$ can be exemplified by formyl, nitro, —CO—B—$R^6$ (wherein, B and $R^6$ are as defined above) and —D—$R^8$ (wherein, D and $R^8$ are as defined above). Preferred examples of —CO—B—$R^6$ are lower alkoxycarbonyl and lower alkoxycarbonylalkoxycarbonyl groups containing each methoxy, ethoxy, propoxy, butoxy, methoxycarbonylmethyl, ethoxycarbonylmethyl, propoxycarbonylmethyl, methoxycarbonylethyl, ethoxycarbonylethyl, or propoxycarbonylethyl. Preferred examples of —D—$R^8$ are; alkoxy and alkylthio groups containing each methyl, ethyl, propyl, or butyl; alkenyloxy groups containing each propenyl, butenyl, or pentenyl; alkynyloxy groups containing each propynyl, butynyl, or pentynyl; alkenylamino groups containing each propenyl, butenyl, or pentenyl; and alkoxycarbonylalkoxy and alkylthiocarbonylalkoxy groups containing each a lower alkyl group such as methyl, ethyl, propyl, or butyl.

The substituent X is a halogen atom which can be exemplified by chlorine, bromine, fluorine, and iodine, of which preferred are chlorine and fluorine.

In the present invention, however, the substituent $R^1$, $R^2$, $R^3$, $R^4$, or X is not limited to the above examples; 3-(substituted phenyl)pyrazole derivatives and salts thereof having substituents other than the above examples exhibit significant herbicidal effect as well, provided that those substituents conform to the definition given above.

Salts of 3-(substituted phenyl)pyrazole derivatives represented by formula (I) are of mineral acids including, e.g. sulfuric acid and hydrochloric acid and of organic acids including, e.g. p-toluenesulfonic acid.

Salts of 3-(substituted phenyl)pyrazole derivatives represented by formula (I) can be produced by treating these derivatives with a suitable mineral acid or organic acid.

Typical processes for producing 3-(substituted phenyl)pyrazole derivatives of formula (I) or salts thereof can be illustrated by the following reaction schemes ①, ②, and ③.

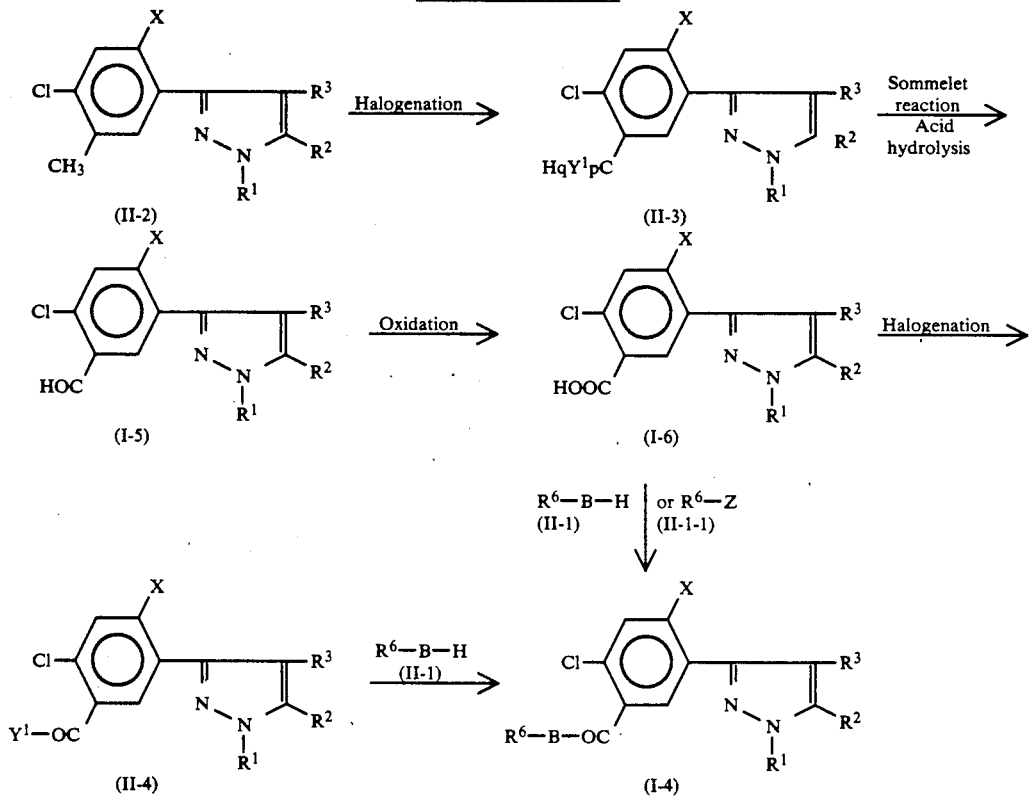

In the above equation, $R^1$, $R^2$, $R^3$, $R^6$, X, and B are as defined above, $Y^1$ and Z denotes halogen, and p and q denote each an integer of 1 or 2 with the provide that the sum of p and q is 3. That is, the 3-(substituted phenyl)pyrazole derivative represented by formula (I-4) can be produced as follows: A pyrazole derivative represented by formula (II-2) is reacted with a halogenating agent in an inert solvent to give a pyrazole derivative represented by formula (II-3), which in turn is subjected to Sommelet reaction with hexamethylenetetramine in an inert solvent and further hydrolyzed with acid to give a 3-(substituted phenyl)pyrazole derivative represented by formula (I-5), which in turn is oxidized in an inert solvent to give (I-6), which in turn is halogenated in an inert solvent to give an acid halide represented by formula (II-4). Pyrazole derivatives represented by the following formula (I-3);

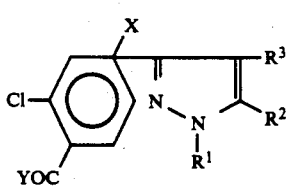

(I-3)

in which $R^1$, $R^2$, $R^3$, $R^6$, X and B are defined above, Y denotes halogen or OH, which consist of a derivative of formula (I-6) (corresponding to the case when Y is OH and a derivative of formula (II-4) (corresponding to the case when Y is halogen) are reacted with a compound represented by formula (II-1) or with a halide represented by formula (II-1-1) in an inert solvent in the presence or absence of a base to produce the 3-(substituted phenyl)pyrazole derivative represented by formula (I-4).

(1) Preparation of compound (II-3) from compound (II-2)

Any inert solvent may be used in this reaction that does not markedly hinder the reaction from proceeding. Such solvents include, though not limited to; halogenated hydrocarbons, e.g. methylene chloride, chloroform, and carbon tetrachloride; aromatic hydrocarbons, e.g. benzene, toluene, and xylene; nitriles, e.g. acetonitrile and benzonitrile; linear ethers, e.g. methyl Cellosolve and diethyl ether; cyclic ethers e.g. dioxane and tetrahydrofuran; and sulforane, dimethyl sulfone and dimethylsulfoxide. These solvents may be used alone or in combination.

Halogenating agents suitable for use in the above reaction include, for example, N-bromosuccinimide (NBS), N-chlorosuccinimide (NCS), bromine, chlorine, t-butyl hypohalogenite, and trichloromethanesulfonyl halide. When NBS or NCS is used as a halogenating agent, it is preferable to use an organic peroxide such as benzoyl peroxide or light as a catalyst or exciter.

The amount of halogenating agent used may be chosen from the range of 1 mole to an excess of 1 mole per mole of the pyrazole derivative of formula (II-2).

The reaction temperature ranges from 0° C. to the boiling point of the inert solvent used.

The reaction period is chosen from the range of several minutes to 48 hours so as to complete the reaction.

After completion of the reaction, the 3-(substituted phenyl)pyrazole derivative of formula (II-3) can be obtained from the reaction product solution by an ordinary method, e.g. solvent extraction, and if necessary, by purification procedure such as recrystallization or column chromatography.

(2) Preparation of compound (I-5) from compound (II-3)

This reaction process consists of the first step of carrying out Sommelet reaction and the second step of carrying out acid hydrolysis. Inert solvents suitable for use in the first step include organic acids, e.g. glacial acetic acid, mineral acids, e.g. hydrochloric acid and sulfuric acid, water, and mixtures of these solvents.

Hexamethylenetetramine is used in an amount equimolar to the pyrazole derivative of formula (II-3). An excess of hexamethylenetetramine can also be used.

The reaction temperature ranges from 10° C. to the boiling point of inert solvent used, preferably from 30° to 180° C.

After completion of the reaction, the resultant solution containing the objective compound is subjected to the acid hydrolysis in the second step.

To the acid hydrolysis, the reaction product solution from the first step is subjected as such or with a large excess of mineral acid such as hydrochloric acid or sulfuric acid added as occasion demands, the latter procedure being preferable.

The reaction temperature is in the range of 80° to 180° C. and the reaction period is chosen from the range of several minutes to 48 hours so as to complete the reaction.

After completion of the reaction, the 3-(substituted phenyl)pyrazole derivative of formula (I-5) can be obtained from the reaction product solution by an ordinary method, e.g. solvent extraction, and if necessary, by purification procedure such as recrystallization or column chromatography.

(3) Preparation of compound (I-6) from compound (I-5)

Inert solvents suitable for use in this reaction include aromatic hydrocarbons such as benzene, toluene, and xylene, and further pyridine and its derivatives and water. These solvents may be used alone or in combination.

Peroxides, e.g. potassium permanganate and potassium dichromate, can be used as oxidizing agents in amounts of 1 to 5 moles, preferably 1 to 2 moles, per mole of the 3-(substituted phenyl)pyrazole derivative of formula (I-5).

The reaction temperature is from 0° C. to the boiling point of inert solvent used, preferably in the range of 30° to 180° C. The reaction period is chosen from the range of several minutes to 48 hours so as to complete the reaction.

After completion of the reaction, the 3-(substituted phenyl)pyrazole derivative of formula (I-6) can be obtained from the reaction product solution by an ordinary method e.g. solvent extraction, and if necessary, by purification procedure such as recrystallization or column chromatography.

(4) Preparation of compound (II-4) from compound (I-6)

Inert solvents suitable for use in this acid halide-forming reaction include; halogenated hydrocarbons, e.g. methylene chloride, chloroform, and carbon tetrachloride; aromatic hydrocarbons, e.g. benzene, toluene, and xylene; linear ethers, e.g. methyl Cellosolve, diethyl ether, and diisopropyl ether; and cyclic ethers, e.g. dioxane and tetrahydrofuran.

Halogenating agents suitable for this reaction include, for example, thionyl chloride, phosphorus pentachloride, and phosphorus trichloride.

The halogenating agent may be used in amounts of 1 mole to an excess of 1 mole, preferably in such an excess, per mole of the 3-(substituted phenyl)pyrazole derivative of formula (I-6).

A catalytic amount of triethylamine, pyridine, dimethylformamide, or the like may be added for the purpose of promoting this reaction.

The reaction temperature is in the range of room temperature to the boiling point of solvent used. The reaction period ranges from several minutes to 48 hours depending upon the amounts of reactants used and the reaction temperature.

After completion of the reaction, the excess halogenating agent and the solvent are removed from the reaction product solution by evaporation to isolate the objective compound, which may be subjected to the next reaction after purification, if necessary, by recrystallization, distillation, or some other method.

(5) Preparation of compound (I-4) from compound (I-6) or from compound (II-4)

This reaction is esterification or amide-forming reaction. The esterification can be carried out by using an excess of the alcohol corresponding to the objective ester in the presence of a mineral acid, e.g. concentrated sulfuric acid, which acts as a reactant and a solvent. For the esterification, the 3-(substituted phenyl)pyrazole derivative of formula (I-6) can also be used in the form of alkali metal salt.

The esterification or the amide-forming reaction can also be carried out in the presence of an inert solvent and a dehalogenating agent. Inert solvents suitable for use in the acid halide-forming reaction can also be used in this case.

The alcohol or amine or the halide of formula (II-1-1) may be used in an equimolar amount or more.

Dehalogenating agents suitable for use in this reaction are inorganic bases and organic bases. The inorganic bases include alkali metal salts, e.g. sodium hydroxide and potassium hydroxide and the organic bases include tertiary amines, e.g. triethylamine, and 4-dimethylaminopyridine, and 1,8-diazabicyclo[5,4,0]-7-undecene (DBU).

The reaction temperature is in the range of 0° C. to the boiling point of the solvent used, preferably in the range of 0° to 150° C. The reaction period ranges from several minutes to 48 hours depending upon the amounts of reactants used, the reaction temperature, etc.

After completion of the reaction, the 3-(substituted phenyl)pyrazole derivative of formula (I-4) can be obtained from the reaction product solution by an ordinary method, e.g. solvent extraction, and if necessary, by purification procedure such as recrystallization or column chromatography.

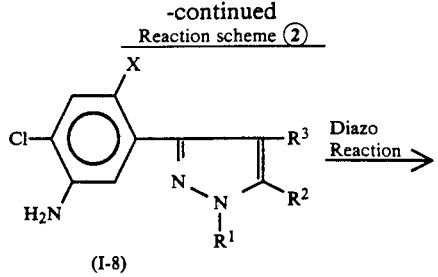

In the above equations, $R^1$, $R^2$, $R^3$, $R^{8-1}$, D, X, and Z are as defined above.

That is, a pyrazole derivative of formula (II-5) is subjected to nitration with a nitrating agent in an inert solvent to give a 3-(substituted phenyl)pyrazole derivative of formula (I-7). This derivative is then reduced in an inert solvent to give a 3-(substituted phenyl)pyrazole derivative of formula (I-8), which is further diazotized in an inert solvent and then decomposed, whereby a 3-(substituted phenyl)pyrazole derivative of formula (I-9) can be obtained. On the other hand, a pyrazole derivative of formula (II-5) is subjected to chlorosulfonyl substitution in an inert solvent to give a pyrazole derivative of formula (II-6), which in turn is reduced, whereby a 3-(substituted phenyl)pyrazole derivative of formula (I-10) can be obtained.

Further, a 3-(substituted phenyl)pyrazole derivative of formula (I-2) can be produced from the 3-(substituted phenyl)pyrazole derivative of formula (I-8), (I-9), or (I-10) by reacting with a halide of formula (II) in an inert solvent in the presence of a base.

When $R^{8-1}$ in the 3-(substituted phenyl)pyrazole derivative of formula (I-2) is —CH —.$R^{10}$—CO.E.$R^{12}$ (wherein, $R^{10}$, $R^{12}$, and E are as defined above), this 3-(substituted phenyl)pyrazole derivative can be produced by converting an acid represented by —CHR$^{10}$—CO—E—H to an acid halide in the same manner as in the above reaction process ①, and subjecting the acid halide to esterification, thiol esterification, or amide-forming reaction.

(1) Preparation of compound (I-7) from compound (II-5)

Nitrating agents suitable for use in this reaction include concentrated nitric acid, a mixture of fuming nitric acid with concentrated sulfuric acid, and acetyl nitrate that is formed by mixing concentrated nitric acid with acetic anhydride.

Mineral acids such as sulfuric acid and hydrochloric acid can be used as solvents in this process.

Since this reaction is an equimolar reaction, the use of an equimolar amount of nitrating agent is sufficient though it may be used in excess.

The reaction temperature is in the range of $-10°$ to $140°$ C., preferably $-10°$ to $20°$ C. The reaction period is chosen from the range of several minutes to 48 hours depending upon the amounts of reactants charged, the reaction temperature, etc.

After completion of the reaction, the intended 3-(substituted-phenyl)pyrazole derivative of formula (I-7) can be -obtained from the reaction product solution by either pouring it into ice-cold water and collecting the precipitated crystals or subjecting the solution to solvent extraction or other separating procedure to isolate the intended product, and if necessary, by further purification procedure such as recrystallization.

(2) Preparation compound (I-8) from compound (I-7)

Any inert solvent that does not markedly hinder the reaction from proceeding may be used in this reaction. Such inert solvents include; alcohols, e.g. methanol, ethanol, and propanol; linear ethers, e.g. diethyl ether and methyl Cellosolve; cyclic ethers, e.g. dioxane and tetrahydrofuran; organic acids, e.g. acetic acid; mineral acids, e.g. hydrochloric acid; and water.

Reducing agents suitable for this reaction in an acidic medium include, for example, zinc, iron, tin, and tin chloride. Zinc dust can be used in a neutral or basic medium. For the catalytic hydrogenation, which can be carried out under normal or elevated pressure, suitable catalysts include, for example, Raney nickel, palladium-carbon, palladium oxide, platinum, platinum black, platinum sulfidecarbon, and rhodium-alumina.

In an acidic medium, the reducing agent may be used in an equimolar amount though generally in excess. For the catalytic hydrogenation, the amount of Raney nickel or the like when it is used is from 5 to 20% by weight based on the weight of the 3-(substituted)-pyrazole derivative of formula (I-7) and the amount of noble metal such as platinum or palladium when it is used is from 0.02 to 5% by weight on the the same basis.

The reaction temperature is in the range of $0°$ to $150°$ C., preferably $10°$ to $100°$ C. The reaction period may be chosen from the range of several minutes to 48 hours depending upon the amounts of reactants charged, the reaction temperature, etc.

After completion of the reaction, the intended 3-(substituted phenyl)pyrazole derivative of formula (I-8) can be obtained in the following manner: When the reaction is carried out in an acidic medium, the reaction product solution is poured into ice-cold water, this mixture is turned basic, and the objective product is isolated by a method such as solvent extraction. In case of catalytic hydrogenation, the catalyst is removed from the reaction product fluid by filtration and the objective product is recovered by concentrating the filtrate. If necessary, the objective product is further purified by recrystallization, column chromatography, or some other method.

(3) Preparation of compound (I-9) from compound (I-8)

This process consists of the step of diazotization and the step of decomposition. In the diazotization step, a mineral acid such as sulfuric acid or hydrochloric acid can be used as an inert solvent. For the diazotization, sodium nitrite in the form of powder or aqueous solution of suitable concentration is used in an equimolar amount or in excess.

The reaction temperature is in the range of $-5°$ to $5°$ C.

The resulting diazonium salt is subjected to decomposition without isolation.

In the decomposition step, 30 to 70% sulfuric acid may be used as an inert solvent.

The decomposition is carried out in the presence of a catalyst at a temperature of $10°$ to $180°$ C. When the diazonium salt in solution form is added dropwise to aqueous sulfuric acid, the reaction is conducted at a temperature of $50°$ to $180°$ C. When cuprous oxide is used, as a catalyst, the reaction temperature is in the range of $10°$ to $50°$ C.

Copper nitrate and cuprous oxide can be used as catalysts. To the reaction system is added copper nitrate and then cuprous oxide is added in limited amounts.

Copper nitrate is used in an amount of 1 to 60 moles, preferably 30 to 60 moles, and cuprous oxide is used in an amount of catalytic to 2 moles, preferably about 1 mole, per mole of the diazonium salt.

The total reaction period of diazotization and decomposition may be chosen from the range of several minutes to 48 hours depending upon the amounts of reactants charged and the reaction temperature.

After completion of the reaction, the 3-(substituted phenyl)pyrazole derivative of formula (I-9) can be obtained by pouring the reaction product solution into ice-cold water, isolating the objective product from the mixture by a method such as solvent extraction, and if necessary, purifying the isolated product by recrystallization, column chromatography, or some other method.

(4) Preparation of compound (II-6) from compound (II-5)

Any solvent may be used for this reaction that does not markedly hinder the reaction. Such solvents include; halogenated hydrocarbons, e.g. methylene chloride, chloroform, and carbon tetrachloride, aliphatic nitriles, e.g. acetonitrile; linear ethers, e.g. methyl Cellosolve; cyclic ethers, e.g. dioxane and tetrahydrofuran; and mineral acids, e.g. concentrated sulfuric acid.

For this chlorosulfonyl substitution, chlorofulfonic acid or the like may be used. Another available method comprises sulfonating the starting compound of formula (II-5) with fuming sulfuric acid, converting the resulting sulfonic acid to an alkali metal salt, and chlorinating it with phosphorus pentachloride to give the objective product. A further method comprises reacting the starting compound with fuming sulfuric acid, followed by the reaction with carbon tetrachloride to give the objective product.

Chlorosulfonic acid is used in an equimolar amount or in excess, preferably in excess.

Fuming sulfuric acid is used also in an equimolar amount or in excess, preferably in excess. Carbon tetrachloride is used in an amount chosen properly from the range of an equimolar amount to an excess.

The reaction temperature is in the range of 0° to 180° C., preferably 15° to 100° C. The reaction period may be chosen from the range of several minutes to 48 hours depending upon the amounts of reactants charged and the reaction temperature.

After completion of the reaction, the 3-(substituted phenyl)pyrazole derivative of formula (II-6) ca be obtained by pouring the reaction product solution into water, isolating the objective product from the resulting mixture by solvent extraction, and if necessary, purifying the isolated product by recrystallization, column chromatography, or some other procedure.

(5) Preparation of compound (I-10) from compound (II-6)

This reduction can be carried out in an inert solvent such as glacial acetic acid. Reducing agents suitable for this reaction include, for example, zinc, tin, and tin chloride, which may be used in an amount of 1 mole or more, preferably 5 moles or more, per mole of the compound of formula (II-6).

The reaction temperature is in the range of 0° to 180° C., preferably 15° to 120° C. The reaction period is chosen from the range of several minutes to 48 hours depending upon the amounts of reactants charged and the reaction temperature.

After completion of the reaction, the 3-(substituted phenyl)pyrazole derivative of formula (I-10) can be obtained by pouring the reaction product solution into water, isolating the objective product from the mixture by solvent extraction, and if necessary, purifying the isolated product by recrystallization, column chromatography, or some other procedure.

(6) Preparation of compound (I-2) from compound (I-9) or compound (I-10)

This reaction can be carried out according to the procedure of the above reaction process ①-5, whereby the 3-(substituted phenyl)pyrazole derivative of formula (I-2) can be produced.

③ Salts of 3-(substituted phenyl)pyrazole derivatives of formula (I)

These salts are formed from acids including mineral acids, e.g. hydrochloric acid and sulfuric acid, and organic acids, e.g. p-toluenesulfonic acid. The production of these salts can be carried out by treating 3-(substituted phenyl)pyrazole derivatives of formula (I), obtained according to the above stated process, with the above-cited mineral acid or organic acid.

Typical examples of the 3-(substituted phenyl)-pyrazole derivatives represented by formula (I) and the salts thereof are shown in Table 1.

TABLE 1

Formula (I)

| Comp'd No. | $R^1$ | $R^2$ | $R^3$ | $R^4$ | X | Property |
|---|---|---|---|---|---|---|
| 1 | $CH_3$ | $CH_3S$ | H | HO | Cl | m.p. 157.1° C. |
| 2 | $CH_3$ | $CH_3S$ | Cl | HO | Cl | m.p. 163.2° C. |
| 3 | $CH_3$ | $CH_3S$ | Cl | $i-C_3H_7O$ | Cl | nD 1.5882(26.5° C.) |
| 4 | $CH_3$ | $CH_3S$ | Cl | $CH_2=CHCH_2O$ | Cl | nD 1.6131(25.3° C.) |
| 5 | $CH_3$ | $CH_3S$ | Cl | $CH\equiv CCH_2O$ | Cl | m.p. 71.5-72.5° C. |
| 6 | $CH_3$ | $CH_3S$ | Cl | $C_2H_5OCH_2CH_2O$ | Cl | nD 1.5944(25,8° C.) |
| 7 | $CH_3$ | $CH_3S$ | Cl | $\mathrm{C_6H_5\text{-}OCH_2CH_2O}$ | Cl | nD 1.6075(25.6° C.) |
| 8 | $CH_3$ | $CH_3S$ | Cl | (2,4-dichlorophenyl)-OOCO | Cl | nD 1.5988(25.9° C.) |
| 9 | $CH_3$ | $CH_3S$ | Cl | $HOOCCH(CH_3)O$ | Cl | m.p. 191-194° C. |
| 10 | $CH_3$ | $CH_3S$ | Cl | $CH_3OOCCH(CH_3)O$ | Cl | m.p. 90-93° C. |
| 11 | $CH_3$ | $CH_3S$ | Cl | $C_2H_5OOCCH(CH_3)O$ | Cl | nD 1.5763(28.8° C.) |
| 12 | $CH_3$ | $CH_3S$ | Cl | $i-C_3H_7OOCCH(CH_3)O$ | Cl | m.p. 87-90° C. |
| 13 | $CH_3$ | $CH_3S$ | Cl | $CH_2=CHCH_2OOCCH(CH_3)O$ | Cl | nD 1.5802(23.4° C.) |
| 14 | $CH_3$ | $CH_3S$ | Cl | $CH\equiv CCH_2OOCCH(CH_3)O$ | Cl | nD 1.5858(23.7° C.) |
| 15 | $CH_3$ | $CH_3S$ | Cl | HS | Cl | nD 1.6303(24.3° C.) |
| 16 | $CH_3$ | $CH_3S$ | Cl | $i-C_3H_7S$ | Cl | m.p. 91.8° C. |
| 17 | $CH_3$ | $CH_3S$ | Cl | $CHF_2S$ | Cl | m.p. 87.2° C. |
| 18 | $CH_3$ | $CH_3S$ | Cl | $CHF_2CF_2S$ | Cl | nD 1.5820(24.7° C.) |
| 19 | $CH_3$ | $CH_3S$ | Cl | $CH_2=CHCH_2S$ | Cl | Viscous substance |

TABLE 1-continued

Formula (I)

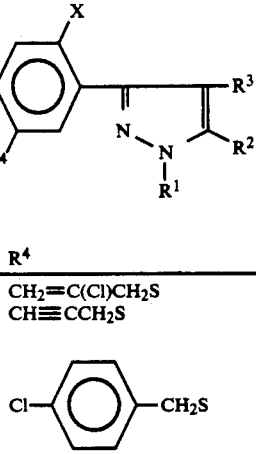

| Comp'd No. | R¹ | R² | R³ | R⁴ | X | Property |
|---|---|---|---|---|---|---|
| 20 | CH₃ | CH₃S | Cl | CH₂=C(Cl)CH₂S | Cl | nD 1.6370(25.1° C.) |
| 21 | CH₃ | CH₃S | Cl | CH≡CCH₂S | Cl | m.p. 94.5° C. |
| 22 | CH₃ | CH₃S | Cl | Cl-C₆H₄-CH₂S | Cl | nD 1.6528(24.9° C.) |
| 23 | CH₃ | CH₃S | Cl | C₂H₅OOCCH₂S | Cl | m.p. 112.1° C. |
| 24 | CH₃ | CH₃S | Cl | C₂H₅OOCCH₂CH₂S | Cl | m.p. 74.8° C. |
| 25 | CH₃ | CH₃S | Cl | HO₂CCH(CH₃)S | Cl | m.p. 180.0° C. |
| 26 | CH₃ | CH₃S | Cl | i-C₃H₇NH₃⊕ ⊖OOCCH(CH₃)S | Cl | nD 1.5878(22.1° C.) |
| 27 | CH₃ | CH₃S | Cl | (CH₃)₂NH₂⊕ ⊖OOCCH(CH₃)S | Cl | m.p. 176.1° C. |
| 28 | CH₃ | CH₃S | Cl | CH₃OOCCH(CH₃)S | Cl | nD 1.6131(24.9° C.) |
| 29 | CH₃ | CH₃S | Cl | C₂H₅OOCCH(CH₃)S | Cl | nD 1.6010(25.0° C.) |
| 30 | CH₃ | CH₃S | Cl | i-C₃H₇OOCCH(CH₃)S | Cl | nD 1.5936(25.0° C.) |
| 31 | CH₃ | CH₃S | Cl | Cl(CH₂)₃OOCCH(CH₃)S | Cl | nD 1.6025(25.2° C.) |
| 32 | CH₃ | CH₃S | Cl | CH₂=CHCH₂OOCCH(CH₃)S | Cl | nD 1.6030(25.0° C.) |
| 33 | CH₃ | CH₃S | Cl | CH≡CCH₂OOCCH(CH₃)S | Cl | nD 1.5954(25.0° C.) |
| 34 | CH₃ | CH₃S | Cl | C₂H₅CH(CH₃)CH₂OOCCH(CH₃)S | Cl | nD 1.5834(25.0° C.) |
| 35 | CH₃ | CH₃S | Cl | (C₂H₅)₂NCOCH(CH₃)S | Cl | nD 1.5983(26.4° C.) |
| 36 | CH₃ | CH₃S | Cl | H₂NSO₂ | Cl | m.p. 203.5° C. |
| 37 | CH₃ | CH₃S | Cl | CH₃NHSO₂ | Cl | m.p. 79.1° C. |
| 38 | CH₃ | CH₃S | Cl | (CH₃)₂NSO₂ | Cl | m.p. 135.7° C. |
| 39 | CH₃ | CH₃S | Cl | n-C₃H₇NHSO₂ | Cl | m.p. 102-105° C. |
| 40 | CH₃ | CH₃S | Cl | CH₃SO₂NHSO₂ | Cl | m.p. 184-187° C. |
| 41 | CH₃ | CH₃S | Cl | H₂N | Cl | nD 1.6403(25.0° C.) |
| 42 | " | " | " | Cl⊖H₃N⊕ | " | m.p. 174.5° C. |
| 43 | " | " | " | CH₃NH | " | nD 1.6368(21.7° C.) |
| 44 | " | " | " | (CH₃)₂N | " | nD 1.6241(22.1° C.) |
| 45 | " | " | " | CH₂=CHCH₂NH | " | nD 1.6238(22.2° C.) |
| 46 | " | " | " | (CH₂=CHCH₂)₂N | " | nD 1.6088(21.6° C.) |
| 47 | " | " | " | CH≡CCH₂NH | " | m.p. 140.8° C. |
| 48 | " | " | " | CH₃OOCNH | " | nD 1.6301(22.2° C.) |
| 49 | " | " | " | HOOC | " | m.p. 213-214° C. |
| 50 | " | " | " | C₂H₅OOC | " | nD 1.6029(20.1° C.) |
| 51 | " | " | " | CH₃SO₂NH | " | nD 1.6002(25.9° C.) |
| 52 | " | " | " | CH₃NHSO₂NH | " | m.p. 134.5° C. |
| 53 | " | " | " | CH₃NHSO₂N(CH₃) | " | nD 1.5763(26.4° C.) |
| 54 | " | " | " | (CH₃)₂NSO₂N(CH₃) | " | nD 1.5839(26.0° C.) |
| 55 | " | " | " | i-C₃H₇NHSO₂NH | " | m.p. 148.6° C. |
| 56 | CH₃ | CH₃S | Cl | CH≡CCH₂N(CH₃)SO₂N(CH≡CCH₂) | Cl | m.p. 111.5° C. |
| 57 | " | " | " | CH₃OCH₂CH₂OOCNH | " | m.p. 112-115° C. |
| 58 | " | " | " | BrCH₂CH₂OOCNH | " | m.p. 119.5° C. |
| 59 | " | " | " | NCCH₂CH₂OOCNH | " | nD 1.5938(24.7° C.) |
| 60 | " | " | " | CH₂=C(CH₃)CH₂OOCNH | " | m.p. 125.8° C. |
| 61 | " | " | " | C₆H₅-CH₂CH₂OOCNH | " | m.p. 103-105° C. |
| 62 | " | " | " | CH₂=CHCH₂OOCCH₂NH | " | m.p. 112.0° C. |
| 63 | " | " | " | CH≡CCH₂OOCCH₂NH | " | m.p. 127.0° C. |
| 64 | " | " | " | C₂H₅OOCCH(CH₃)NH | " | Viscous substance |
| 66 | " | " | " | HOOCCH₂NH | " | m.p. 207.1° C. |
| 67 | " | " | " | CH₃OOCCH₂NH | " | m.p. 132.4° C. |
| 68 | " | " | " | HOOCCH(CH₃)NH | " | m.p. 218.7° C. |
| 69 | " | " | " | CH₃OOCCH(CH₃)NH | " | m.p. 144.2° C. |
| 70 | CH₃ | CH₃SO | Cl | NO₂ | Cl | m.p. 168.1° C. |
| 71 | " | " | " | CH₃SO₂NH | " | m.p. 168.0° C. |

TABLE 1-continued

Formula (I)

| Comp'd No. | R¹ | R² | R³ | R⁴ | X | Property |
|---|---|---|---|---|---|---|
| 72 | " | " | " | CH₃NHSO₂NH | " | m.p. 146.3° C. |
| 73 | " | " | " | i-C₃H₇NHSO₂NH | " | m.p. 184.8° C. |
| 74 | " | " | " | CH₃NHSO₂N(CH≡CCH₂) | " | m.p. 192.5° C. |
| 75 | CHF₂ | CH₃S | " | NH₂ | " | m.p. 87.4° C. |
| 76 | " | " | " | CH₃NHSO₂NH | " | m.p. 133.3° C. |
| 77 | " | " | " | CH₃NHSO₂N(CH≡CCH₂) | " | nD 1.5625(25.6° C.) |
| 78 | " | " | " | CH₃N(CH≡CCH₂)SO₂N(CH≡CCH₂) | " | nD 1.5675(25.6° C.) |
| 79 | " | CH₃SO | " | NH₂ | " | m.p. 187.1° C. |
| 80 | " | " | " | NO₂ | " | m.p. 165.1° C. |
| 81 | CH₃ | CHF₂O | " | CH₃O | " | nD 1.5567(23.4° C.) |
| 82 | " | " | " | C₂H₅O | " | nD 1.5434(23.5° C.) |
| 83 | " | " | " | n-C₃H₇O | " | nD 1.5410(25.1° C.) |
| 84 | " | " | " | i-C₃H₇O | " | nD 1.5422(23.5° C.) |
| 85 | CH₃ | CHF₂O | Cl | cyclopentyl-O | Cl | nD 1.5482(25.4° C.) |
| 86 | " | " | " | CH₂=CHCH₂O | " | nD 1.5536(28.4° C.) |
| 87 | " | " | " | CH≡CCH₂O | " | m.p. 84.0° C. |
| 88 | " | " | " | C₂H₅OCH₂CH₂O | " | m.p. 79.5° C. |
| 89 | " | " | " | NCCH₂O | " | m.p. 98.9° C. |
| 90 | " | " | " | CH₃OOCO | " | nD 1.5387(23.2° C.) |
| 91 | " | " | " | CH₃OOCCH₂O | " | m.p. 119.8° C. |
| 92 | " | " | " | n-C₃H₇OOCCH₂O | " | m.p. 89.7° C. |
| 93 | " | " | " | i-C₃H₇OOCCH₂O | " | m.p. 105.0° C. |
| 94 | " | " | " | n-C₄H₉OOCCH₂O | " | m.p. 75.3° C. |
| 95 | " | " | " | CH₃CH₂CH(CH₃)OOCCH₂O | " | m.p. 107.8° C. |
| 96 | " | " | " | n-C₆H₁₃OOCCH₂O | " | nD 1.5244(23.0° C.) |
| 97 | " | " | " | CH₂=CHCH₂OOCCH₂O | " | m.p. 84.7° C. |
| 98 | " | " | " | CH≡CCH₂OOCCH₂O | " | m.p. 119.6° C. |
| 99 | CH₃ | CHF₂O | Cl | cyclohexyl-OOCCH₂O | Cl | m.p. 91.8° C. |
| 100 | " | " | " | C₂H₅O(CH₂)₂OOCCH₂O | " | nD 1.5261(22.9° C.) |
| 101 | " | " | " | C₂H₅O(CH₂)₂O(CH₂)₂OOCCH₂O | " | nD 1.5287(23.0° C.) |
| 102 | " | " | " | C₆H₅-CH₂OOCCH₂O | " | m.p. 139.1° C. |
| 103 | " | " | " | HOOCCH(CH₃)O | " | m.p. 158.7° C. |
| 104 | " | " | " | i-C₃H₇NH₃⊕ ⊖OOCCH(CH₃)O | " | Viscous substance |
| 105 | " | " | " | C₂H₅OOCCH(CH₃)O | " | nD 1.5238(25.7° C.) |
| 106 | " | " | " | n-C₄H₉OOCCH(CH₃)O | " | nD 1.5253(18.5° C.) |
| 107 | " | " | " | CH₂=CHCH₂OOCCH(CH₃)O | " | m.p. 84.3° C. |
| 108 | " | " | " | CH≡CCH₂OOCCH(CH₃)O | " | m.p. 109.7° C. |
| 109 | " | " | " | CH₃NHCOCH(CH₃)O | " | nD 1.5365(35.2° C.) |
| 110 | " | " | " | (CH₃)₂NCOCH(CH₃)O | " | m.p. 148.9° C. |
| 111 | " | " | " | HS | " | nD 1.5828(21.8° C.) |
| 112 | CH₃ | CHF₂O | Cl | CH₃S | Cl | m.p. 95.7° C. |
| 113 | " | " | " | C₂H₅S | " | m.p. 110.5° C. |
| 114 | " | " | " | i-C₃H₇S | " | m.p. 83.8° C. |
| 115 | " | " | " | n-C₄H₉S | " | m.p. 155.4° C. |
| 116 | " | " | " | CHF₂S | " | m.p. 123.4° C. |
| 117 | " | " | " | CH₂=CHCH₂S | " | m.p. 52.0–55.0° C. |
| 118 | " | " | " | CH₂=CHCH₂SO | " | m.p. 91.5° C. |
| 119 | " | " | " | CH≡CCH₂S | " | m.p. 127–129° C. |

TABLE 1-continued

Formula (I)

[Structure: Cl-substituted phenyl ring with X, R⁴ substituents, connected to pyrazole ring with R¹, R², R³]

| Comp'd No. | R¹ | R² | R³ | R⁴ | X | Property |
|---|---|---|---|---|---|---|
| 120 | " | " | " | C₆H₅-CH₂S | " | nD 1.5972(20.2° C.) |
| 121 | " | " | " | (C₂H₅O)₂P(O)CH₂S | " | nD 1.5245(25.3° C.) |
| 122 | " | " | " | CH₃OOCS | " | nD 1.5656(17.2° C.) |
| 123 | " | " | " | CH₃OOCCH₂S | " | m.p. 102.0° C. |
| 124 | " | " | " | C₂H₅OOCCH₂S | " | m.p. 171.5° C. |
| 125 | " | " | " | CH₂=CHCH₂OOCCH₂S | " | m.p. 102.4° C. |
| 126 | CH₃ | CHF₂O | Cl | HOOCCH(CH₃)S | Cl | m.p. 188.9° C. |
| 127 | " | " | " | ⊕ ⊖ NaOOCCH(CH₃)S | " | m.p. 205.4° C. |
| 128 | " | " | " | ⊕ ⊖ i-C₃H₇NH₃OOCCH(CH₃)S | " | Viscous substance |
| 129 | " | " | " | CH₃OOCCH(CH₃)S | " | nD 1.5654(19.8° C.) |
| 130 | " | " | " | C₂H₅OOCCH(CH₃)S | " | nD 1.5565(28.0° C.) |
| 131 | " | " | " | C₂H₅OOCCH(CH₃)S(O) | " | nD 1.5582(20.0° C.) |
| 132 | " | " | " | C₂H₅OOCCH(CH₃)SO₂ | " | m.p. 105.8° C. |
| 133 | " | " | " | i-C₃H₇OOCCH(CH₃)S | " | nD 1.5417(22.1° C.) |
| 134 | " | " | " | n-C₄H₉OOCCH(CH₃)S | " | nD 1.5458(20.2° C.) |
| 135 | " | " | " | (CH₃)₂CH(CH₂)₂OOCCH(CH₃)S | " | nD 1.5437 (22.2° C.) |
| 136 | " | " | " | CH₂=CHCH₂OOCCH(CH₃)S | " | nD 1.5600(20.4° C.) |
| 137 | " | " | " | CH≡CCH₂OOCCH(CH₃)S | " | nD 1.5602(22.2° C.) |
| 138 | " | " | " | CH₃O(CH₂)₂O(CH₂)₂OOCCH(CH₃)S | " | nD 1.5431(23.5° C.) |
| 139 | " | " | " | (C₂H₅O)₂P(O)CH₂OOCCH(CH₃)S | " | nD 1.5386(21.2° C.) |
| 140 | CH₃ | CHF₂O | Cl | CH₃NHCOCH(CH₃)S | Cl | m.p. 99.9° C. |
| 141 | " | " | " | (CH₃)₂NCOCH(CH₃)S | " | nD 1.5672(19.9° C.) |
| 142 | " | " | " | (C₂H₅)₂NCOCH(CH₃)S | " | nD 1.5532(19.8° C.) |
| 143 | " | " | " | i-C₃H₇NHCOCH(CH₃)S | " | m.p. 99.9° C. |
| 144 | " | " | " | C₆H₅-NHCOCH(CH₃)S | " | m.p. 132.3° C. |
| 145 | " | " | " | O(CH₂CH₂)₂N-COCH(CH₃)S (morpholino) | " | nD 1.5457(19.9° C.) |
| 146 | " | " | " | NO₂ | " | m.p. 99.1° C. |
| 147 | " | " | " | NH₂ | " | nD 1.5743(20.8° C.) |
| 148 | " | " | " | CH₃SO₂NH | " | m.p. 142.9° C. |
| 149 | " | " | " | CH₃NHSO₂NH | " | m.p. 133.0° C. |
| 150 | " | " | " | CH₃NH | " | nD 1.4952(25.2° C.) |
| 151 | " | " | " | (CH₃)₂N | " | nD 1.5561(24.9° C.) |
| 152 | " | " | " | CH₂=CHCH₂NH | " | nD 1.5719(25.3° C.) |
| 153 | " | " | " | CH≡CCH₂NH | " | m.p. 76.3° C. |
| 154 | CH₃ | CHF₂O | Cl | CH₃OOCNH | Cl | m.p. 162.3° C. |
| 155 | " | " | " | Cl⊖H₃N⊕ | " | m.p. 137.1° C. |
| 156 | " | " | " | CH₃-C₆H₄-SO₃⊖H₃N⊕ | " | m.p. 244.1° C. |
| 157 | " | " | " | CH₃OOCCH₂NH | " | m.p. 96.2° C. |
| 158 | " | " | " | HOOCCH(CH₃)NH | " | m.p. 192.3° C. |

TABLE 1-continued

Formula (I)

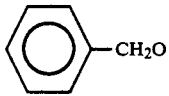

| Comp'd No. | R¹ | R² | R³ | R⁴ | X | Property |
|---|---|---|---|---|---|---|
| 159 | " | " | " | Na⊕ ⊖OOCCH(CH₃)NH | " | m.p. 248.0 (decomp.) |
| 160 | " | " | " | i-C₃H₇NH₃⊕ ⊖OOCCH(CH₃)NH | " | Viscous substance |
| 161 | " | " | " | C₂H₅OOCCH(CH₃)NH | " | nD 1.5371(23.4° C.) |
| 162 | " | " | " | CH₃NHOCCH(CH₃)NH | " | nD 1.5500(25.6° C.) |
| 163 | " | " | " | (CH₃)₂NOCCH(CH₃)NH | " | nD 1.5510(25.2° C.) |
| 164 | " | " | " | CH₃NHSO₂ | " | nD 1.5461(17.9° C.) |
| 165 | " | " | " | (CH₃)₂NSO₂ | " | m.p. 135.2° C. |
| 166 | " | " | " | (C₂H₅)₂NCOS | " | nD 1.5623(17.7° C.) |
| 167 | CH₃ | CHF₂S | Cl | CH₃O | Cl | nD 1.5767(21.9° C.) |
| 168 | " | " | " | C₂H₅O | " | nD 1.5810(23.8° C.) |
| 169 | " | " | " | i-C₃H₇O | " | nD 1.5536(24.2° C.) |
| 170 | " | " | " | n-C₆H₁₃O | " | nD 1.5460(24.2° C.) |
| 171 | " | " | " | CH₂=CHCH₂O | " | nD 1.5791(19.8° C.) |
| 172 | " | " | " | CH≡CCH₂O | " | nD 1.5720(20.0° C.) |
| 173 | " | " | " | 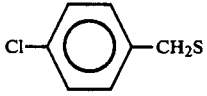—CH₂O | " | nD 1.6226(24.3° C.) |
| 174 | " | " | " | CH₃OOCCH₂O | " | nD 1.5629(23.1° C.) |
| 175 | " | " | " | C₂H₅OOCCH(CH₃)O | " | nD 1.5569(23.6° C.) |
| 176 | " | " | " | HS | " | nD 1.6218(23.5° C.) |
| 177 | " | " | " | CH₃S | " | nD 1.6069(21.7° C.) |
| 178 | " | " | " | C₂H₅S | " | nD 1.6047(24.1° C.) |
| 179 | " | " | " | i-C₃H₇S | " | nD 1.5893(23.6° C.) |
| 180 | " | " | " | n-C₅H₁₁S | " | nD 1.5881(25.0° C.) |
| 181 | CH₃ | CHF₂S | Cl | CHF₂S | Cl | nD 1.5869(24.2° C.) |
| 182 | " | " | " | CH₂=CHCH₂S | " | nD 1.6173(21.3° C.) |
| 183 | " | " | " | CH≡CCH₂S | " | nD 1.6261(23.4° C.) |
| 184 | " | " | " | C₂H₅OCH₂CH₂S | " | nD 1.5816(22.3° C.) |
| 185 | " | " | " | CH₃SCH₂S | " | nD 1.6222(24.2° C.) |
| 186 | " | " | " | NCCH₂S | " | m.p. 95.9° C. |
| 187 | " | " | " | Cl—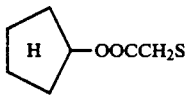—CH₂S | " | nD 1.6273(24.3° C.) |
| 188 | " | " | " | C₂H₅OOCS | " | nD 1.5720(21.8° C.) |
| 189 | " | " | " | CH₃OOCCH₂S | " | m.p. 112.1° C. |
| 190 | " | " | " | C₂H₅OOCCH₂S | " | m.p. 97.8° C. |
| 191 | " | " | " | cyclopentyl-OOCCH₂S | " | m.p. 104.4° C. |
| 192 | " | " | " | CH₃NHOCCH₂S | " | m.p. 138.6° C. |
| 193 | " | " | " | (CH₃)₂NOCCH₂S | " | m.p. 138.3° C. |
| 194 | CH₃ | CHF₂S | Cl | HOOCCH(CH₃)S | Cl | m.p. 149.5° C. |
| 195 | " | " | " | NaOOCCH(CH₃)S | " | m.p. 220.8° C. |
| 196 | " | " | " | i-C₃H₇NH₃⊕ ⊖OOCCH(CH₃)S | " | Viscous substance |
| 197 | " | " | " | C₂H₅OOCCH(CH₃)S | " | nD 1.5788(23.4° C.) |
| 198 | " | " | " | n-C₃H₇OOCCH(CH₃)S | " | nD 1.5643(19.4° C.) |
| 199 | " | " | " | i-C₃H₇OOCCH(CH₃)S | " | nD 1.5695(19.4° C.) |
| 200 | " | " | " | (CH₃)₂CHCH₂OOCCH₂S | " | nD 1.5812(21.2° C.) |

TABLE 1-continued

Formula (I)

| Comp'd No. | R¹ | R² | R³ | R⁴ | X | Property |
|---|---|---|---|---|---|---|
| 201 | " | " | " | CH$_2$=CHCH$_2$OOCCH(CH$_3$)S | " | nD 1.5800(19.4° C.) |
| 202 | " | " | " | C$_2$H$_5$OOC(CH$_2$)$_3$S | " | m.p. 110.7° C. |
| 203 | " | " | " | CH$_3$NHOCCH(CH$_3$)S | " | m.p. 140.8° C. |
| 204 | " | " | " | (CH$_3$)$_2$NOCCH(CH$_3$)S | " | nD 1.5791(21.0° C.) |
| 205 | " | " | " | NO$_2$ | " | m.p. 109.6° C. |
| 206 | " | " | " | NH$_2$ | " | nD 1.5837(20.3° C.) |
| 207 | " | " | " | (CH$_3$)$_2$N | " | nD 1.5838(21.6° C.) |
| 208 | CH$_3$ | CHF$_2$S | Cl | CH$_2$=CHCH$_2$NH | Cl | nD 1.6060(21.2° C.) |
| 209 | " | " | " | (CH$_2$=CHCH$_2$)$_2$N | " | nD 1.5884(24.0° C.) |
| 210 | " | " | " | CH≡CCH$_2$NH | " | nD 1.6052(23.1° C.) |
| 211 | " | " | " | CH$_3$SO$_2$NH | " | m.p. 165.7° C. |
| 212 | " | " | " | CH$_3$NHSO$_2$NH | " | nD 1.5812(20.4° C.) |
| 213 | " | " | " | CH$_3$OOCNH | " | m.p. 144.5° C. |
| 214 | " | " | " | (C$_2$H$_5$)$_2$NCOS | " | nD 1.5753(21.5° C.) |
| 215 | " | CH$_3$S | " | C$_2$H$_5$OOCCH(CH$_3$)O | Cl | nD 1.5584(25.7° C.) Dimethyl sulfate quaternary ammonium salt |
| 216 | " | CHF$_2$O | " | (CH$_3$)$_3$SiCH$_2$S | " | nD 1.5568(22.8° C.) |
| 217 | " | CH$_3$SO | " | 5-NO$_2$ | F | m.p. 151.0° C. |
| 218 | " | CH$_3$S | " | 5-NH$_2$ | " | nD 1.6260(27.3° C.) |
| 219 | " | " | " | 5-SH | " | Viscous substance |
| 220 | " | " | " | 5-CH≡CCH$_2$O | " | nD 1.5980(25.2° C.) |
| 221 | " | " | " | 5-CH≡CCH$_2$S | " | m.p. 93–96° C. |
| 222 | CH$_3$ | CH$_3$S | Cl | 5-C$_2$H$_5$OOCCH(CH$_3$)S | F | nD 1.5880(26.4° C.) |
| 223 | " | SCH$_3$ | " | CH$_3$O—COCH$_2$O | Cl | mp. 126.2° C. |
| 224 | " | " | " | C$_2$H$_5$O—COCH$_2$O | " | mp. 106.5° C. |
| 225 | " | OCHF$_2$ | H | CH$_2$=CHCH$_2$O | " | mp. 56.2° C. |
| 226 | " | " | " | CH≡CCH$_2$O | " | mp. 100.0° C. |
| 227 | " | " | Cl | OHC | " | mp. 138.2° C. |
| 228 | " | " | " | CH$_2$=C(CH$_3$)CH$_2$O | " | nD 1.5387(24.3° C.) |
| 229 | " | " | " | (CH$_3$)$_3$SiCH$_2$O | " | nD 1.5271(23.9° C.) |
| 230 | " | " | " | HO—COCH$_2$O | " | mp. 162.0° C. |
| 231 | " | " | " | Na$^⊕$ $^⊖$O—COCH$_2$O | " | mp. 238.0° C. |
| 232 | " | " | " | K$^⊕$ $^⊖$O—COCH$_2$O | " | mp. 194.0° C. |
| 233 | " | " | " | i-C$_3$H$_7$NH$_3$$^⊕$ $^⊖$O—COCH$_2$O | " | mp. 131.0° C. |
| 234 | " | " | " | C$_2$H$_5$O—COCH$_2$O | " | mp. 102.3° C. |
| 235 | " | " | " | t-C$_4$H$_9$O—COCH$_2$O | " | mp. 92.2° C. |
| 236 | CH$_3$ | OCHF$_2$ | Cl | CH$_2$=CHC(CH$_3$)$_2$O—COCH$_2$O | Cl | mp. 92.8° C. |
| 237 | " | " | " | CH$_3$C≡CCH$_2$O—COCH$_2$O | " | mp. 104.3° C. |
| 238 | " | " | " | CH$_3$S—COCH$_2$O | " | mp. 117.5° C. |
| 239 | " | " | " | C$_2$H$_5$S—COCH$_2$O | " | mp. 86.0° C. |
| 240 | " | " | " | i-C$_3$H$_7$S—COCH$_2$O | " | mp. 98.0° C. |
| 241 | " | " | " | CH$_3$NHCOCH$_2$O | " | mp. 149.7° C. |
| 242 | " | " | " | (CH$_3$)$_2$NCOCH$_2$O | " | mp. 153.3° C. |
| 243 | " | " | " | n-C$_4$H$_9$NHCOCH$_2$O | " | mp. 106.9° C. |
| 244 | " | " | " | H$_2$C=CHCH$_2$NHCOCH$_2$O | " | mp. 127.7° C. |
| 245 | " | " | " | (H$_2$C=CHCH$_2$)$_2$NCOCH$_2$O | " | mp. 80.0° C. |
| 246 | " | " | " | C$_6$H$_5$—NHCOCH$_2$O | " | mp. 205.6° C. |
| 247 | " | " | " | C$_6$H$_5$—N(CH$_3$)COCH$_2$O | " | nD 1.5570(18.7° C.) |
| 248 | " | " | " | CH$_3$SO$_2$NHCOCH$_2$O | " | mp. 124.5° C. |

TABLE 1-continued

Formula (I)

| Comp'd No. | R¹ | R² | R³ | R⁴ | X | Property |
|---|---|---|---|---|---|---|
| 249 | " | " | " | $(CH_3)_3SiCH_2O-COCH_2O$ | " | nD 1.5223(29.5° C.) |
| 250 | $CH_3$ | $OCHF_2$ | Cl | $CH_3OC_2H_4OC_2H_4O-COCH(CH_3)O$ | Cl | nD 1.5142(23.9° C.) |
| 251 | " | " | " | $C_2H_5O-COCH(C_2H_5)O$ | " | nD 1.5286(26.5° C.) |
| 252 | " | " | " | $C_2H_5O-CO(CH_2)_3O$ | " | nD 1.5238(17.3° C.) |
| 253 | " | " | " | $CH_3O-COCH(i-C_3H_7)O$ | " | nD 1.5273(24.3° C.) |
| 254 | " | " | " | $CH_3SO_2NHCOCH(CH_3)O$ | " | mp. 51.6° C. |
| 255 | " | " | " | OHC | F | mp. 107.3° C. |
| 256 | " | " | " | $CH_2=CHCH_2O$ | " | mp. 63.7–64.1° C. |
| 257 | " | " | " | $CH_2=C(CH_3)CH_2O$ | " | nD 1.5376(17.3° C.) |
| 258 | " | " | " | $CH\equiv CCH_2O$ | " | mp. 98.0–98.1° C. |
| 259 | " | " | " | $CH_3C\equiv CCH_2O$ | " | mp. 108.5° C. |
| 260 | " | " | " | $HO-COCH_2O$ | " | mp. 143.7° C. |
| 261 | " | " | " | $CH_3O-COCH_2O$ | " | mp. 122.8–123.1° C. |
| 262 | " | " | " | $C_2H_5O-COCH_2O$ | " | mp. 127.6° C. |
| 263 | " | " | " | $n-C_3H_7O-COCH_2O$ | " | mp. 97.6–97.8° C. |
| 264 | " | " | " | $i-C_3H_7O-COCH_2O$ | " | 120.3–120.5° C. |
| 265 | $CH_3$ | $OCHF_2$ | Cl | $n-C_4H_9O-COCH_2O$ | F | mp. 91.4–91.6° C. |
| 266 | " | " | " | $CH_2=CHCH_2O-COCH_2O$ | " | mp. 89.2–89.4° C. |
| 267 | " | " | " | $CH\equiv CCH_2O-COCH_2O$ | " | mp. 99.0° C. |
| 268 | " | " | " | $C_2H_5S-COCH_2O$ | " | mp. 69.3° C. |
| 269 | " | " | " | $i-C_3H_7S-COCH_2O$ | " | mp. 83.8° C. |
| 270 | " | " | " | $HO-COCH(CH_3)O$ | " | mp. 94.5° C. |
| 271 | " | " | " | $CH_3O-COCH(CH_3)O$ | " | mp. 95.6° C. |
| 272 | " | " | " | $C_2H_5O-COCH(CH_3)O$ | " | mp. 67.0–67.2° C. |
| 273 | " | " | " | $CH_2=CHCH_2O-COCH(CH_3)O$ | " | Viscous substance |
| 274 | " | " | " | $CH\equiv CCH_2O-COCH(CH_3)O$ | " | nD 1.5266(25.8° C.) |
| 275 | " | " | " | $C_2H_5O-COCH(C_2H_5)O$ | " | nD 1.5105(22.6° C.) |
| 276 | " | " | " | $CH_2=C(CH_3)CH_2S$ | Cl | nD 1.5775(21.7° C.) |
| 277 | " | " | " | $CH_2=C(Cl)CH_2S$ | " | nD 1.5865(21.5° C.) |
| 278 | " | " | " | $ClCH=CHCH_2S$ | " | nD 1.5867(21.2° C.) |
| 279 | " | " | " | $ClCH=C(Cl)CH_2S$ | " | nD 1.5926(22.8° C.) |
| 280 | " | " | " | $NCCH_2S$ | " | mp. 122.3° C. |
| 281 | $CH_3$ | $OCHF_2$ | Cl | $Na^{\oplus} \ ^{\ominus}O-COCH_2S$ | Cl | mp. 232.0° C. |
| 282 | " | " | " | $(i-C_3H_7)NH_3^{\oplus} \ ^{\ominus}O-COCH_2S$ | " | mp. 113.0° C. |
| 283 | " | " | " | $HO-COCH_2S$ | " | mp. 164.2° C. |
| 284 | " | " | " | $i-C_3H_7O-COCH_2S$ | " | mp. 99.1° C. |
| 285 | " | " | " | $n-C_4H_9O-COCH_2S$ | " | mp. 62.0° C. |
| 286 | " | " | " | $C_{12}H_{25}O-COCH_2S$ | " | nD 1.5010(27.2° C.) |
| 287 | " | " | " | $CH_3S-COCH_2S$ | " | mp. 98.3° C. |
| 288 | " | " | " | $C_2H_5S-COCH_2S$ | " | mp. 73.1° C. |
| 289 | " | " | " | $i-C_3H_7S-COCH_2S$ | " | mp. 97.0° C. |
| 290 | " | " | " | $CH\equiv CCH_2O-COCH_2S$ | " | mp. 85.9° C. |
| 291 | " | " | " | $C_2H_5OC_2H_4OC_2H_4O-COCH_2S$ | " | mp. 76.5° C. |
| 292 | " | " | " | cyclohexyl-$O-COCH_2S$ | " | mp. 87.8° C. |
| 293 | " | " | " | phenyl-$CH_2O-COCH_2S$ | " | mp. 82.8° C. |
| 294 | $CH_3$ | $OCHF_2$ | Cl | $(CH_3)_3SiCH_2O-COCH_2S$ | Cl | nD 1.5387(29.1° C.) |
| 295 | " | " | " | $CH_3NHCOCH_2S$ | " | mp. 177.8° C. |
| 296 | " | " | " | $(CH_3)_2NCOCH_2S$ | " | mp. 121.6° C. |
| 297 | " | " | " | $H_2C=CHCH_2NHCOCH_2S$ | " | mp. 146.6° C. |
| 298 | " | " | " | $(H_2C=CHCH_2)_2NCOCH_2S$ | " | mp. 71.8° C. |
| 299 | " | " | " | $HC\equiv CCH_2NHCOCH_2S$ | " | mp. 172.0° C. |

TABLE 1-continued

Formula (I)

[Structure: 4-Cl, 2-position connected to CH=N-N(R¹) pyrazoline with R², R³ substituents, and R⁴ at 5-position, X at 6-position]

| Comp'd No. | R¹ | R² | R³ | R⁴ | X | Property |
|---|---|---|---|---|---|---|
| 300 | " | " | " | (phenyl)-NHCOCH₂S | " | mp. 178.1° C. |
| 301 | " | " | " | (phenyl)-N(CH₃)COCH₂S | " | nD 1.5661(21.5° C.) |
| 302 | " | " | " | (pyrrolidine)NCOCH₂S | " | mp. 120.4° C. |
| 303 | " | " | " | (morpholine, O...NCOCH₂S) | " | mp. 126.5° C. |
| 304 | " | " | " | i-C₄H₉O—COCH(CH₃)S | " | Viscous substance |
| 305 | " | " | " | t-C₄H₉CH₂O—COCH(CH₃)S | " | nD 1.5462(13.9° C.) |
| 306 | CH₃ | OCHF₂ | Cl | n-C₆H₁₃O—COCH(CH₃)S | Cl | nD 1.5210(23.2° C.) |
| 307 | " | " | " | (phenyl)-CH₂O—COCH(CH₃)S | " | Viscous substance |
| 308 | " | " | " | C₂H₅S—COCH(CH₃)S | " | nD 1.5790(24.0° C.) |
| 309 | " | " | " | i-C₃H₇S—COCH(CH₃)S | " | nD 1.5669(24.2° C.) |
| 310 | " | " | " | NCCH(CH₃)O—COCH(CH₃)S | " | nD 1.5501(23.1° C.) |
| 311 | " | " | " | CH₃SC₂H₄O—COCH(CH₃)S | " | nD 1.5609(23.1° C.) |
| 312 | " | " | " | (cyclohexyl)-O—COCH(CH₃)S | " | Viscous substance |
| 313 | " | " | " | (phenyl)-S—COCH(CH₃)S | " | nD 1.5956(14.3° C.) |
| 314 | " | " | " | (CH₃)₃SiCH₂O—COCH(CH₃)S | " | nD 1.5429(26.8° C.) |
| 315 | " | " | " | CH₂=CHCH₂NHCOCH(CH₃)S | " | nD 1.5619(22.6° C.) |
| 316 | " | " | " | (H₂C=CHCH₂)₂NCOCH(CH₃)S | " | nD 1.5603(22.9° C.) |
| 317 | " | " | " | HC≡CCH₂NHCOCH(CH₃)S | " | nD 1.5496(23.1° C.) |
| 318 | " | " | " | CH₃CO—O—(CH₂)₂S | " | nD 1.5603(26.9° C.) |
| 319 | " | " | " | C₂H₅O—COC(CH₃)₂S | " | mp. 96.4° C. |
| 320 | CH₃ | OCHF₂ | Cl | CH₃O—COCH(i-C₃H₇)S | Cl | nD 1.5572(23.4° C.) |
| 321 | " | " | " | C₂H₅O—COCH(CH₃)N(CH₃) | " | nD 1.5365(22.8° C.) |
| 322 | " | " | " | HO—CO | " | mp. 216.7° C. |
| 323 | " | " | " | CH₃O—CO | " | mp. 63.9° C. |
| 324 | " | " | " | C₂H₅O—CO | " | nD 1.5446(26.8° C.) |
| 325 | " | " | " | CH₂=CHCH₂O—CO | " | nD 1.5317(26.8° C.) |
| 326 | " | " | " | CH₃O—COCH(CH₃)O—CO | " | nD 1.5370(25.7° C.) |
| 327 | " | " | " | C₂H₅O—COCH(CH₃)O—CO | " | nD 1.5672(26.0° C.) |
| 328 | " | " | " | CH≡CCH₂O—CO | " | mp. 78.5° C. |
| 329 | " | " | Br | BrCH₂CH(Br)CH₂O | " | nD 1.5862(22.3° C.) |
| 330 | " | " | " | BrC≡CCH₂O | " | nD 1.5603(22.9° C.) |
| 331 | " | " | " | CH₃O—COCH₂O | " | mp. 133.8° C. |
| 332 | " | " | " | C₂H₅O—COCH(CH₃)O | " | nD 1.5396(20.8° C.) |

TABLE 1-continued

Formula (I)

| Comp'd No. | R¹ | R² | R³ | R⁴ | X | Property |
|---|---|---|---|---|---|---|
| 333 | " | SCHF$_2$ | Cl | NCCH$_2$O | " | nD 1.5571(26.1° C.) |
| 334 | " | " | " | CH$_2$=C(CH$_3$)CH$_2$O | " | nD 1.5767(26.3° C.) |
| 335 | CH$_3$ | SCHF$_2$ | Cl | ClCH=CHCH$_2$O | Cl | nD 1.5930(25.8° C.) |
| 336 | " | " | " | CH$_3$OCH$_2$O | " | nD 1.5765(23.8° C.) |
| 337 | " | " | " | C$_2$H$_5$OC$_2$H$_4$O | " | nD 1.5713(23.4° C.) |
| 338 | " | " | " | CH$_3$OCH$_2$S | " | mp. 82.6° C. |
| 339 | " | " | " | ClCH=CHCH$_2$S | " | nD 1.6194(26.3° C.) |
| 340 | " | " | " | CH$_2$=C(Cl)CH$_2$S | " | nD 1.6137(26.2° C.) |
| 341 | " | OCHF$_2$ | " | HS | F | mp. 72.6° C. |
| 342 | " | " | " | CH$_3$S | " | mp. 84.5° C. |
| 343 | " | " | " | F$_2$HCS | " | nD 1.5377(24.0° C.) |
| 344 | " | " | " | CH$_2$=CHCH$_2$S | " | nD 1.5670(17.9° C.) |
| 345 | " | " | " | CH$_2$=C(CH$_3$)CH$_2$S | " | nD 1.5637(19.1° C.) |
| 346 | " | " | " | CH≡CCH$_2$S | " | mp. 82.8° C. |
| 347 | " | " | " | C$_2$H$_5$OC$_2$H$_4$S | " | nD 1.5523(24.0° C.) |
| 348 | " | " | " | HO—COCH$_2$S | " | mp. 132.2° C. |
| 349 | " | " | " | CH$_3$O—COCH$_2$S | " | nD 1.5579(24.0° C.) |
| 350 | CH$_3$ | OCHF$_2$ | Cl | C$_2$H$_5$O—COCH$_2$S | F | nD 1.5342(17.9° C.) |
| 351 | " | " | " | C$_2$H$_5$O—COCH$_2$S(O) | " | nD 1.5420(25.0° C.) |
| 352 | " | " | " | n-C$_4$H$_9$O—COCH$_2$S | " | nD 1.5391(24.1° C.) |
| 353 | " | " | " | CH$_2$=CHCH$_2$O—COCH$_2$S | " | nD 1.5562(24.1° C.) |
| 354 | " | " | " | CH$_3$SCH$_2$O—COCH$_2$S | " | mp. 57.9° C. |
| 355 | " | " | " | ⟨cyclohexyl-H⟩—O—COCH$_2$S | " | mp. 58.9° C. |
| 356 | " | " | " | ⟨phenyl⟩—CH$_2$O—COCH$_2$S | " | nD 1.5794(17.9° C.) |
| 357 | " | " | " | CH$_3$NHCOCH$_2$S | " | mp. 147.0° C. |
| 358 | " | " | " | (CH$_3$)$_2$NCOCH$_2$S | " | mp. 141.2° C. |
| 359 | " | " | " | HO—COCH(CH$_3$)S | " | nD 1.5463(19.1° C.) |
| 360 | " | " | " | CH$_3$O—COCH(CH$_3$)S | " | nD 1.5494(25.0° C.) |
| 361 | " | " | " | C$_2$H$_5$O—COCH(CH$_3$)S | " | nD 1.5328(18.0° C.) |
| 362 | " | " | " | n-C$_4$H$_9$O—COCH(CH$_3$)S | " | nD 1.5343(25.1° C.) |
| 363 | CH$_3$ | OCHF$_2$ | Cl | CH$_2$=CHCH$_2$O—COCH(CH$_3$)S | F | nD 1.5471(25.0° C.) |
| 364 | " | " | " | CH≡CCH$_2$O—COCH(CH$_3$)S | " | Viscous substance |
| 365 | " | " | " | CH$_3$OC$_2$H$_4$OC$_2$H$_4$O—COCH(CH$_3$)S | " | nD 1.5355(18.4° C.) |
| 366 | " | " | " | CH$_3$SO$_2$NH | " | mp. 146.9° C. |
| 367 | " | " | " | CH$_3$NHSO$_2$NH | " | mp. 131.2° C. |
| 368 | " | " | " | CH$_2$=CHCH$_2$NH | " | nD 1.5424(23.6° C.) |
| 369 | " | " | " | CH≡CCH$_2$NH | " | nD 1.5510(27.1° C.) |
| 370 | " | " | " | C$_2$H$_5$O—COCH$_2$NH | " | mp. 111.5° C. |
| 371 | " | " | " | C$_2$H$_5$O—COCH(CH$_3$)NH | " | nD 1.5264(26.6° C.) |
| 372 | " | " | " | CH$_3$O—CO | " | nD 1.5430(17.0° C.) |
| 373 | " | " | " | C$_2$H$_5$O—CO | " | nD 1.5320(21.0° C.) |
| 374 | " | " | " | CH$_2$=CHCH$_2$O—CO | " | nD 1.5218(20.5° C.) |
| 375 | " | " | " | CH≡CCH$_2$O—CO | " | nD 1.5820(24.5° C.) |
| 376 | " | " | " | CH$_3$O—COCH(CH$_3$)O—CO | " | nD 1.5314(23.0° C.) |
| 377 | " | " | " | C$_2$H$_5$O—COCH(CH$_3$)O—CO | " | nD 1.5212(14.1° C.) |
| 378 | CH$_3$ | SCHF$_2$ | Cl | ⟨phenyl⟩—OC$_2$H$_4$O | Cl | mp. 102.9° C. |
| 379 | " | " | " | ⟨cyclopentyl-H⟩—O—COCH$_2$S | " | mp. 104.4° C. |
| 380 | " | " | " | HO—COCH$_2$O | " | mp. 157.7° C. |

TABLE 1-continued

Formula (I)

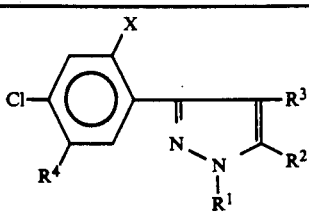

| Comp'd No. | R¹ | R² | R³ | R⁴ | X | Property |
|---|---|---|---|---|---|---|
| 381 | " | " | " | Na⁺ ⁻O—COCH₂O | " | mp. 135.2° C. |
| 382 | " | " | " | C₂H₅O—COCH₂O | " | nD 1.5736(24.0° C.) |
| 383 | " | " | " | i-C₃H₇O—COCH₂O | " | mp. 113.3° C. |
| 384 | " | " | " | CF₃CH₂O—COCH₂O | " | mp. 117.5° C. |
| 385 | " | " | " | CH₂=CHCH₂O—COCH₂O | " | mp. 77.2° C. |
| 386 | " | " | " | (cyclohexyl-H)—O—COCH₂O | " | nD 1.5619(28.3° C.) |
| 387 | " | " | " | CH₃NHCOCH₂O | " | mp. 116.8° C. |
| 388 | " | " | " | CH₃O—COCH(CH₃)O | " | nD 1.5620(23.4° C.) |
| 389 | " | " | " | i-C₃H₇O—COCH(CH₃)O | " | nD 1.5496(24.5° C.) |
| 390 | CH₃ | SCHF₂ | Cl | CH₂=CHCH₂O—COCH(CH₃)O | Cl | nD 1.5643(23.5° C.) |
| 391 | " | " | " | CH₃NHCOCH(CH₃)O | " | nD 1.5641(23.5° C.) |
| 392 | " | " | " | CH₃O—COCH(n-C₄H₉)O | " | nD 1.5488(28.1° C.) |
| 393 | " | " | " | NCCH₂O—COCH₂O | " | nD 1.5694(28.0° C.) |
| 394 | " | " | " | CH₃O—COCH(CH₃)S | " | nD 1.5891(26.4° C.) |
| 395 | " | " | " | NCCH₂O—COCH(CH₃)S | " | nD 1.5801(26.5° C.) |
| 396 | " | " | " | C₂H₅O—CO(CH₂)₃S | " | mp. 107.0° C. |
| 397 | " | " | " | (phenyl)—N(CH₃)COCH₂O | " | mp. 136.9° C. |
| 398 | " | " | " | HO—COCH₂NH | " | mp. 204.0° C. (decomp.) |
| 399 | " | " | " | C₂H₅O—COCH₂NH | " | mp. 110.0° C. |
| 400 | " | " | " | C₂H₅O—COCH(CH₃)NH | " | nD 1.5730(23.9° C.) |
| 401 | " | OCHF₂ | " | (cyclohexyl-H)—OCOCH₂O | " | mp. 91.8° C. |
| 402 | " | " | " | (phenyl)—CH₂O—COCH₂O | " | mp. 139.1° C. |
| 403 | CH₃ | OCHF₂ | Cl | HO—CO | F | Solid substance |
| 404 | " | " | " | NO₂ | " | " |
| 405 | " | " | " | NH₂ | " | Viscous substance |
| 406 | " | " | " | HO— | " | Solid substance |
| 407 | " | " | " | Na⁺ ⁻O—CO | Cl | mp. 246.4° C. |
| 408 | " | " | " | CH₃O—CO—OCH₂S—CO | " | nD 1.5727(24.1° C.) |
| 409 | " | " | " | (CH₃)₂NCO | F | Viscous substance |
| 410 | " | " | " | i-C₃H₇NH₄₃CO | " | nD 1.5269(23.5° C.) |

Table 2 shows NMR data on viscous or crystalline substances shown in Table 1.

TABLE 2

| Comp'd No. | NMR (δ value, CDCl₃/TMS, ppm |
|---|---|
| 19 | 2.38 (3H, s), 3.50 (2H, br), 3.96 (3H, s), 4.93–5.33 (2H, m), 5.46–6.23 (1H, m), 7.25 (1H, s), 7.43 (1H, s). |

TABLE 2-continued

| Comp'd No. | NMR (δ value, CDCl₃/TMS, ppm |
|---|---|
| 64 | 1.23 (3H, t), 1.51 (3H, d), 2.40 (3H, s), 3.97 (3H, s), 4.18 (2H, q), 3.80–4.16 (1H, m), 4.90 (1H, d), 6.64 (1H, s), 7.40 (1H, s). |
| 104 | 1.13 (6H, d), 1.58 (3H, d), 2.83–3.45 |

TABLE 2-continued

| Comp'd No. | NMR ( δ value, CDCl3/TMS, ppm |
|---|---|
|  | (1H, m), 3.80 (3H, s), 4.59 (1H, q), 6.75 (1H, t), 6.92 (1H, s), 7.51 (1H, s), 7.75–8.35 (3H, br). |
| 128 | 1.18 (6H, d), 1.49 (3H, d), 2.92–3.58 (1H, m), 3.81 (3H, s), 4.06 (1H, q), 6.68 (1H, t), 7.43 (2H, s), 7.62–8.32 (3H, br). |
| 160 | 1.12 (6H, d), 1.48 (3H, d), 2.60–3.30 (1H, m), 3.73 (3H, s), 3.91 (1H, q), 6.55 (1H, s), 6.68 (1H, s), 7.33 (1H, s), 7.98 (3H, s). |
| 196 | 1.20 (6H, d), 1.48 (3H, d), 3.28 (1H, m), 3.90 (1H, m), 4.00 (3H, s), 6.74 (1H, t, J=56 Hz), 7.45 (2H, s), 8.00 (3H, s). |
| 219 | 2.28 (3H, t), 3.91 (1H), 3.99 (3H, s), 7.21 (1H, d), 7.50 (1H, d). |
| 273 | 1.70 (3H, d), 3.80 (3H, s), 4.5–4.9 (2H), 5.0–5.5 (2H), 5.5–5.2 (1H), 6.70 (1H, t, J=73 Hz), 7.0–7.4 (2H). |
| 304 | 0.82 (6H, d), 1.56 (3H, d), 3.80 (2H, d), 3.73–4.23 (2H, m), 6.70 (1H, t), 7.20 (1H, s), 7.23 (1H,s). |
| 307 | 1.53 (3H, d), 3.75 (3H, s), 4.06 (1H, q), 5.10 (2H, s), 6.61 (1H, t), 7.18 (5H, s), 7.41 (1H, s). |
| 312 | 1.53 (3H, d), 0.68–2.11 (10H, m), 3.80 (3H, s), 4.10 (1H, q), 4.33–4.90 (1H, br), 6.70 (1H, t), 7.20 (1H, s), 7.23 (1H, s). |
| 364 | 1.54 (3H, d), 2.42 (1H, t), 3.80 (3H, s), 3.98 (1H, q), 4.61 (2H, d), 6.71 (1H, t, J=72 Hz), 7.31 (1H, d, J=9 Hz), 7.80 (1H, d, J=7.6 Hz). |
| 404 (CDCl3 + d6 · DMSO) | 3.80 (3H, s), 6.70 (1H, t, J=72 Hz), 7.22 (1H, d, J=10 Hz), 8.12 (1H, d, J=8 Hz). |
| 405 | 3.83 (3H, s), 6.67 (1H, t, J=72 Hz), 7.36 (1H, d, J=10 Hz), 8.20 (1H, d, J=8 Hz). |
| 406 | 3.73 (3H, s), 3.85 (2H, s, br), 6.64 (1H, t, J=72 Hz), 6.82 (1H, d, J=8 Hz), 7.04 (1H, d, J=10 Hz). |
| 407 | 3.80 (3H, s), 6.00 (1H, Br), 6.65 (1H, t, 72 Hz), 7.01 (1H, d, J=10 Hz), 7.01 (1H, d, J=8 Hz) |
| 410 | 3.10 (6H, s), 3.80 (3H, s), 6.70 (1H, t, J=72 Hz), 7.23 (1H, d, J=10 Hz), 7.53 (1H, d, J=8 Hz) |

Pyrazole derivatives of formula (II-2) that are starting materials for 3-(substituted phenyl)pyrazole derivatives of formula (I) or salts thereof can be produced, for instance, according to the following reaction schemes. Pyrazole derivatives of formula (II-2), in connection with their raw materials, are classified into groups of formulae (II-7), (II-8), (II-9), and (II-10).

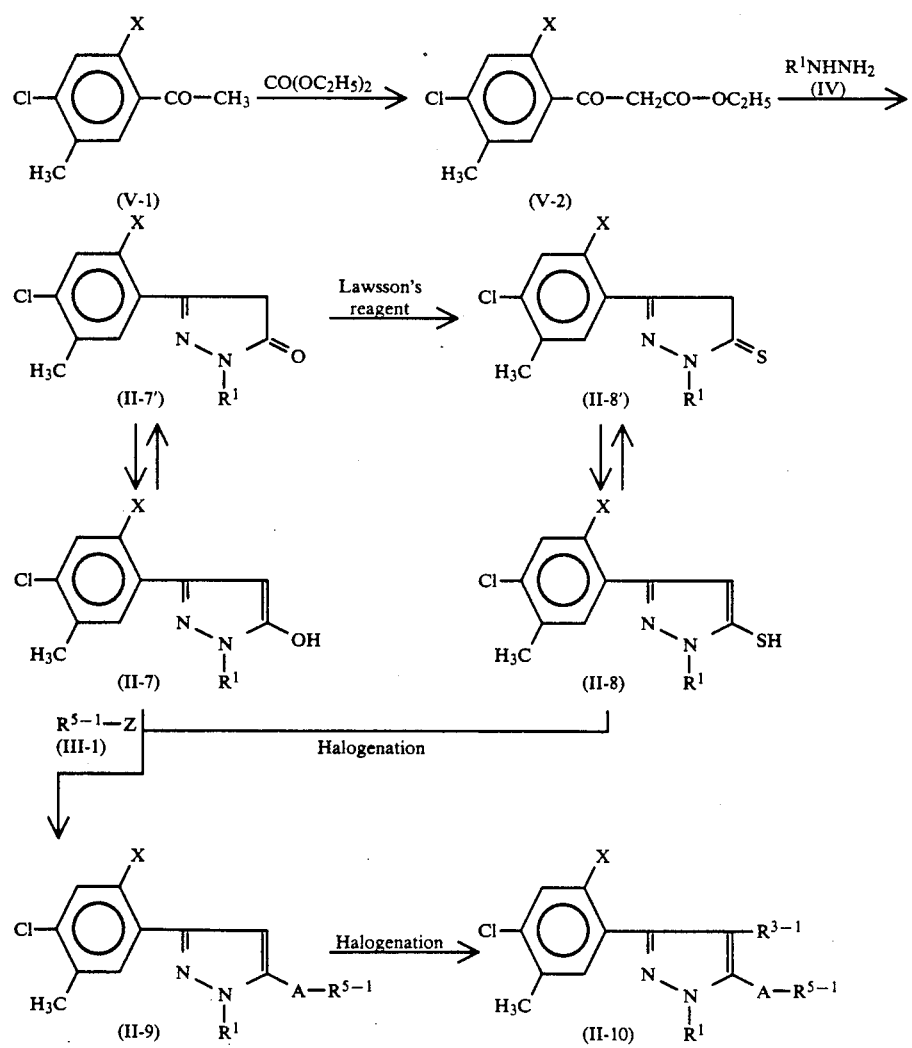

In the above equations, $R^1$, $R^2$, $R^5$, X, and Z are as defined above, $R^{3-1}$ denotes halogen, and $R^{5-1}$ denotes lower alkyl or lower haloalkyl.

As shown above, a pyrazole derivative of formula (II-8') can be prepared by reacting a compound of formula (V-1) with diethyl carbonate, reacting the resulting compound of formula (V-2) with a hydrazine of formula (IV), and reacting the resulting pyrazole derivative of formula (II-7') with Lawsson's reagent.

The pyrazole derivative of formula (II-10) can be produced from a pyrazole derivative of formula (II-7) that is the tautomer of pyrazole derivative of formula (II-7') or from a pyrazole derivative of formula (II-8) that is the tautomer of pyrazole derivative of formula (II-8') by reacting a halide of formula (III-1), followed by halogenating the resulting pyrazole derivative of formula (II-9).

Thus, the pyrazole derivatives of formula (II-2) can be produced that are raw materials used in the above production process ①.

Pyrazole derivatives of formula (II-5) that are raw materials in the process ② A can be produced from compounds of the following formula (V-3) in the same manner as stated above.

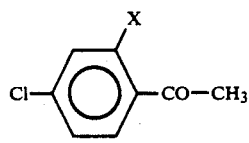
(V-3)

Table III shows typical examples of the compounds of formula (II-2) which have been prepared according to the above process

TABLE 3

Formula (II-2)

| Comp'd No. | $R^1$ | $R^2$ | $R^3$ | X | Property |
|---|---|---|---|---|---|
| II.1 | CH₃ | OCH₃ | Cl | F | nD 1.5633 (26.5° C.) |
| II.2 | CH₃ | OCHF₂ | H | Cl | nD 1.5467 (24.4° C.) |
| II.3 | CH₃ | OCHF₂ | H | F | Oily matter |
| II.4 | CH₃ | OCHF₂ | Cl | Cl | nD 1.5511 (24.5° C.) |
| II.5 | CH₃ | OCHF₂ | Cl | F | mp. 93.7° C. |
| II.6 | CH₃ | OCHF₂ | Br | Cl | nD 1.5627 (24.8° C.) |
| II.7 | CH₃ | OCHF₂ | Br | F | mp. 126.4° C. |
| II.8 | i-C₃H₇ | SCH₃ | H | F | Oily matter |
| II.9 | i-C₃H₇ | SCH₃ | Cl | F | nD 1.5830 (15.1° C.) |
| II.10 | t-C₄H₉ | OCHF₂ | Cl | F | nD 1.5402 (24.8° C.) |
| II.11 | t-C₄H₉ | OCHF₂ | Br | F | nD 1.4848 (24.2° C.) |

Table 4 shows typical examples of the pyrazole derivatives of formula (II-5)

TABLE 4

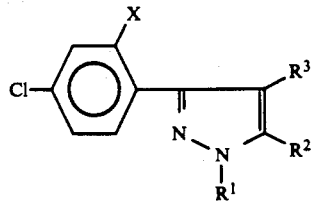
Formula (II-5)

| Comp'd No. | $R^1$ | $R^2$ | $R^3$ | X | Property |
|---|---|---|---|---|---|
| II.12 | CH₃ | OCH₃ | H | Cl | mp. 79.4° C. |
| II.13 | CH₃ | SCH₃ | H | Cl | mp. 59.5–60.0° C. |
| II.14 | CH₃ | SCH₃ | H | F | mp. 40.8° C. |
| II.15 | CH₃ | OCH₃ | Cl | Cl | mp. 71–73° C. |
| II.16 | CH₃ | SCH₃ | Cl | Cl | mp. 62.5 –63.5° C. |
| II.17 | CH₃ | SCH₃ | Cl | F | nD 1.6066 (21.5° C.) |
| II.18 | CH₃ | OCH₃ | Br | Cl | mp. 83–85° C. |
| II.19 | CH₃ | SCH₃ | Br | Cl | mp. 70.0–75.5° C. |
| II.20 | CH₃ | OCHF₂ | H | Cl | mp. 39.2° C. |
| II.21 | CH₃ | SCHF₂ | H | Cl | nD 1.6001 (20.2° C.) |
| II.22 | CH₃ | OCHF₂ | H | F | mp. 41.2–41.5° C. |
| II.23 | CH₃ | OCHF₂ | Cl | Cl | mp. 27–28° C. |
| II.24 | CH₃ | SCHF₂ | Cl | Cl | nD 1.5900 (20.2° C.) |
| II.25 | CH₃ | OCHF₂ | Cl | F | mp. (35.9–36.2° C.) |
| II.26 | CH₃ | OCHF₂ | Br | Cl | nD 1.5664 (21.0° C.) |
| II.27 | CH₃ | SCHF₂ | Br | Cl | nD 1.5993 (18.3° C.) |
| II.28 | CH₃ | OCHF₂ | Br | F | mp. 63.9° C. |
| II.29 | CH₃ | OCHF₂ | F | Cl | nD 1.5441 (20.8° C.) |
| II.30 | CH₃ | OCF₂CHF₂ | H | Cl | nD 1.5237 (20.5° C.) |
| II.31 | CH₃ | OCF₂CHF₂ | Cl | Cl | nD 1.5283 (10.6° C.) |
| II.32 | CH₃ | OCF₂CF₂Cl | Cl | Cl | mp. 68–70° C. |
| II.33 | CH₃ | OCF₂CHFCF₃ | H | Cl | mp. 68–70° C. |
| II.34 | C₂H₅ | OCHF₂ | Cl | Cl | nD 1.5422 (27.3° C.) |

The present invention is illustrated with reference to typical examples thereof, which are not to restrict the scope of the invention.

EXAMPLE 1

Preparation of 2-chloro-5-(4-chloro-5-difluoromethoxy-1-methyl-1H-pyrazol-3-yl)-4-benzoic acid (compound No. 403)

1-1 Preparation of 3-(5-bromomethyl-4-chloro-2-fluorophenyl)-4-chloro-5-difluoromethoxy-1-methyl-1H-pyrazole

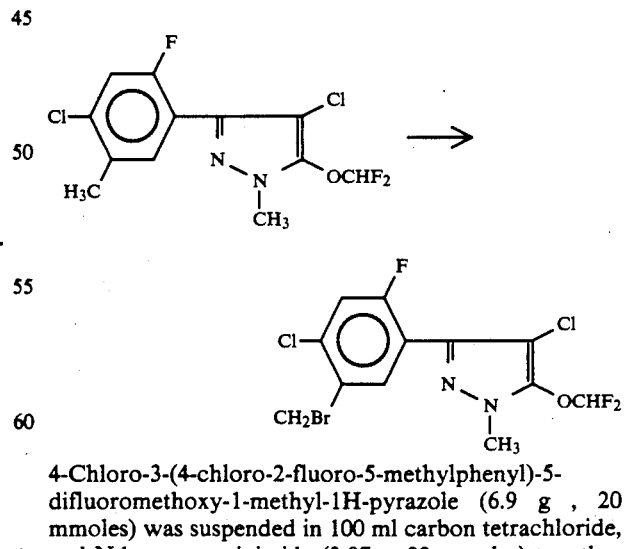

4-Chloro-3-(4-chloro-2-fluoro-5-methylphenyl)-5-difluoromethoxy-1-methyl-1H-pyrazole (6.9 g, 20 mmoles) was suspended in 100 ml carbon tetrachloride, and N-bromosuccinimide (3.97 g, 22 mmoles) together with a catalytic amount of benzoyl peroxide was added and reacted with the pyrazole derivative under reflux for 5 hours. Then the removal of insoluble matter from the product solution by filtration, concentration of the filtrate, and purification of the residue by column chromatography gave the title compound (5.64 g) as a viscous substance, yield 70%.

NMR (CDCl₃/TMS), δ (ppm): 3.83 (3H, s), 4.53 (2H, s), 6.67 (1H, t, J=72 Hz), 7.22 (1H, d, J=10 Hz), 7.60 (1H, d, J=8 Hz).

1-2 Preparation of 2-chloro-(4-chlor--5-difluoromethoxy-1-methyl-1H-pyrazol-3-yl)-4-fluorobenzaldehyde (compound No. 255)

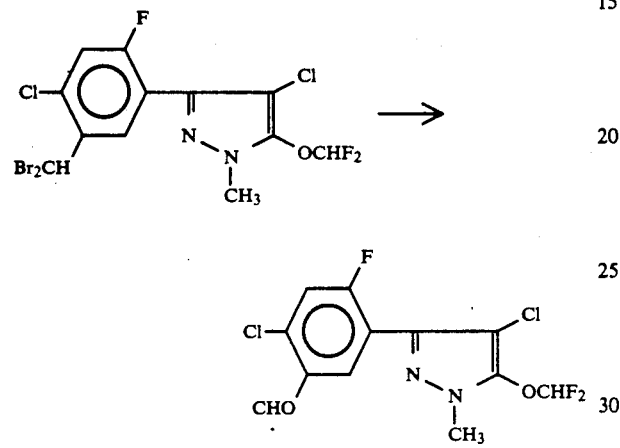

4-Chloro-3-(4-chloro-5-dibromomethyl-2-fluorophenyl)-5-difluromethoxy-1-methyl-1H-pyrazole (14.4 g, 30 mmoles) was suspended in 50 ml conc. hydrochloric acid and reacted under reflux for 5 hours. Then the reaction product solution, poured into ice-cold water, was extracted with ethyl acetate. The extract solution was washed successively with 5% aqueous NaHCO₃ and water, and dehydrated and concentrated. The residue was purified by column chromatography, giving the title compound (6.0 g), m.p. 107.3° C., yield 59%.

1-3 Preparation of 2-chloro-5-(4-chloro-5-difluoromethoxy-1-methyl-1H-pyrazol-3-yl)-4-fluorobenzoic acid (compound No. 403)

A solution of potassium permanate (1.1 g, 7 mmoles) in 22 ml water was dropped slowly into a suspension of 2-chloro-5-(4-chloro-5-difluoromethoxy-1-methyl-1H-pyrazol-3-yl)-4-fluorobenzaldehyde (1.7 g, 5 mmoles) in 18 ml water at 70–80° C. to react. After dropping was finished, the reaction was further continued for 1 hour at 70–80° C. Then the reaction product solution was cooled to room temperature, and made alkaline with 10% aqueous NaOH. The by-product manganese dioxide was filtered off, and washed with hot water. The filtrate and the washing were mixed together, acidified with hydrochloric acid, and extracted with ether. The ether layer was washed with water, dehydrated, and evaporated to dryness, giving the title compound (1.0 g) in block form, yield 56%.

EXAMPLE 2

Preparation of ethyl 5-(4-chloro-1-methyl-5-methylthio-1H-pyrazol-3-yl)-2,4dichlorobenzoate (compound No. 50)

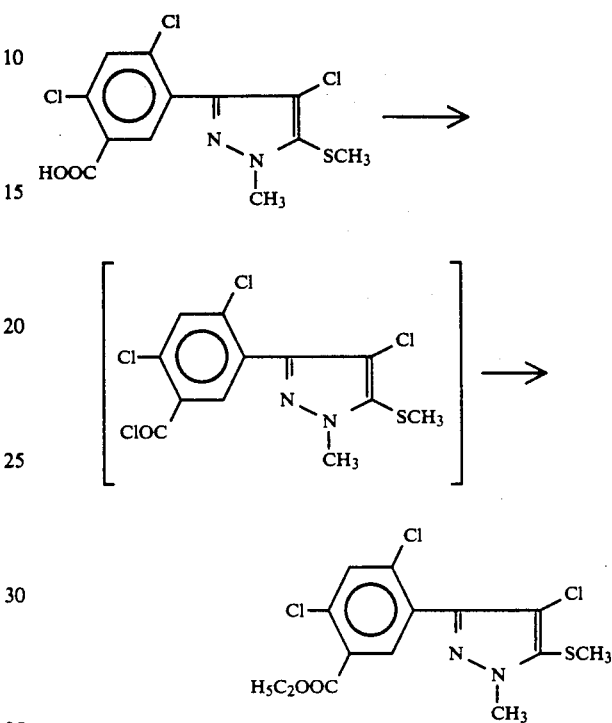

Ethyl 5-(4-chloro-1-methyl-5-methylthio-1H)pyrazol-3-yl)-2,4-dichlorobenzoate (0.30 g, 0.85 mmole) and thionyl chloride (0.10 g, 0.85 mmole), mixed with 20 ml methylene chloride, were reacted together under reflux for 2 hours. Then the solvent was evaporated away under reduced pressure to give an acid chloride, which in turn was reacted with a large excess of ethanol under reflux for 1.5 hours. Then, removal of the solvent by evaporation under reduced pressure and purification of the resulting residue by silica gel column chromatography gave the title compound (0.11 g) in paste form, yield 33.9%.

nD(20.1° C.): 1.6029

EXAMPLE 3

Preparation of methyl 2-chloro-5-(4-chloro-5-difluoromethoxy-1-methyl-1H-pyrazol-3-yl)-4-fluorobenzoate (compound No. 372)

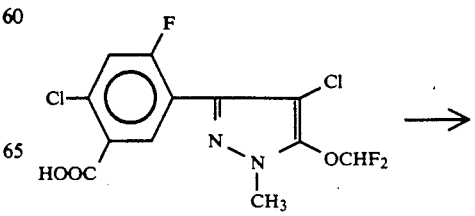

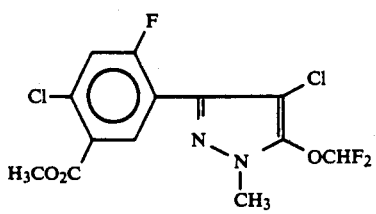

A KOH powder (0.1 g, 1.8 mmoles) and methyl iodide (0.26 g, 1.8 mmols) were added to a solution of 2-chloro-5-(4-chloro-5-difluoromethoxy-1-methyl-1H-pyrazol-3-yl)-4-fluorobenzoic acid (0.30 g, 0.8 moles) in 20 ml acetone and reacted with this pyrazole derivative under reflux 3 hours. Then the extraction with ethylacetate, washing with water, dehydration, and concentration of the extract solution, and purification of the residue by column chromatography gave the title compound (0.15 g), yield 48%.

nD (17.0° C.): 1.5430

EXAMPLE 4

Preparation of 5-(4-chloro-5-difluoromethoxy-1-methyl-1H-pyrazol-3-yl)-2,4-dichlorobenzaldehyde (compound No. 227)

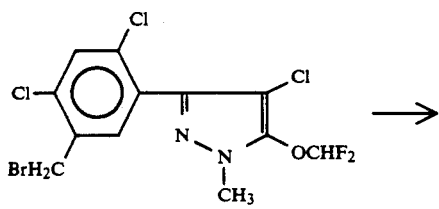

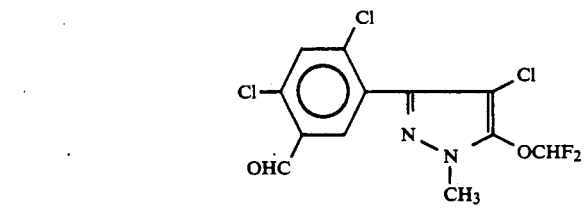

After addition of 100 ml water to a solution of 3-(5-bromomethyl-2,4-dichlorophenyl)-4-chloro-5-difluoromethoxy-1-methyl-1H-pyrazole (26.60 g, 63.3 mmoles) in 100 ml glacial acetic acid, hexamethylenetetramine (8.87 g, 63.3 mmoles) was added and reacted under reflux for 2 hours. Further, 40 ml conc. sulfuric acid was added and reacted under reflux for 13 hours. Then the reaction product mixture, poured into ice-cold water, was extracted with ethyl acetate. The extract solution was washed with 5% aqueous NaHCO$_3$ and then with water, dehydrated, and concentrated. Purification of the residue by column chromatography gave the title compound (12.66 g), m.p. 138.2° C., yield 56.3%.

EXAMPLE 5

Preparation of 4-chloro-3-(4-chloro-2-fluoro-5-nitrophenyl)-5-difluoromethoxy-1-methyl-1H-pyrazole (compound No. 405)

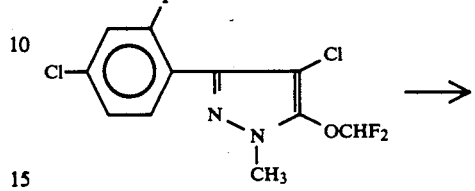

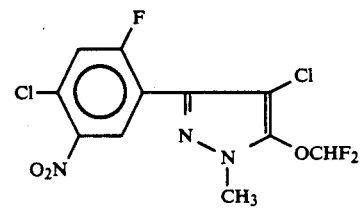

A mixture of 60% nitric acid (1.58 g, 0.015 mole) and conc. sulfuric acid (4.90 g, 0.05 mole) was added dropwise to a solution of 4-chloro-3-(4-chloro-2-fluorophenyl)-5-difluoromethoxy-1-methyl-1H-pyrazole (3.11 g, 0.01 mole) in 6 ml conc. sulfuric acid at temperatures of −10° to 10° C. Thereafter the reaction mixture was further stirred for 3 hours at room temperature. The reaction product mixture, poured into ice-cold water, was extracted with ethyl acetate. The ethyl acetate layer was washed successively with 5% aqueous NaHCO$_3$ and water, dehydrated, and evaporated to dryness, giving the title compound (3.0 g), yield 84%.

NMR, δ (ppm): 3.83 (3H, s), 6.67 (1H, t, J=72 Hz), 7.36 (1H, d, J=10 Hz), 8.20 (1H, d, J=8 Hz).

EXAMPLE 6

Preparation of 4-chloro-3-(4-chloro-2-fluoro-5-nitrophenyl)-1-methyl-5-methylsulfinyl-1H-pyrazole (compound No. 217)

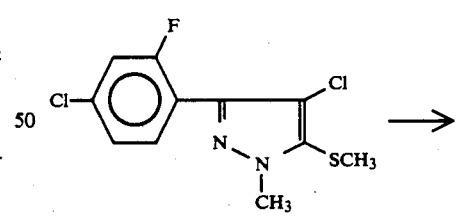

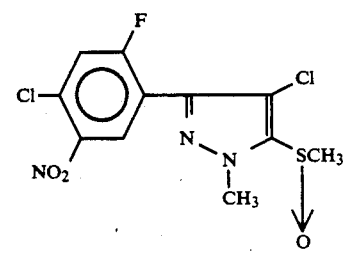

A mixture of conc. sulfuric acid (1.65 g) and conc. nitric acid (sp. gr. 1.38, 8.4 mmoles) was added dropwise to a solution of 4-chloro-3-(4-chloro-2-fluorophenyl)-1-methyl-5-methylthio-1H-pyrazole (0.98 g, 3.4 mmoles) in 2 ml conc. sulfuric acid under cooling with ice. After the addition was finished, the reaction mixture was further stirred for 2 hours at room temperature, and allowed to stand overnight. Then the resulting mixture was poured into ice-cold water, and the formed crystals were filtered off, washed successively with water and ether, and dried, crystals (1.04 g) of the title compound, m.p. 151.0° C., yield 87.5%.

EXAMPLE 7

Preparation of 3-(5-amino-4-chloro-2-fluorophenyl)-4-chloro-5-difluoromethoxy-1-methyl-1H-pyrazole (compound No. 405)

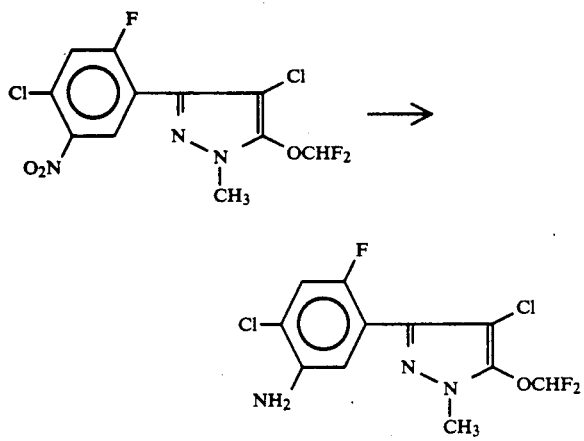

To 4-chloro-3-(4-chloro-2-fluoro-5-nitrophenyl)-5-difluoromethoxy-1-methyl-1H-pyrazole (3.0 g, 8.5 mmoles) in a mixture of 15 ml ethanol and 15 ml conc. hydrochloric acid was added stannous chloride (7.70 g, 34 mmole) and the reduction was conducted under reflux for 8 hours. Then the product solution was poured into ice-cold water, the resulting mixture was made alkaline with 20% aqueous NaOH, and the objective product was extracted with ethyl acetate. Dehydration and concentration of the extract solution and purification of the residue by column chromatography gave the title compound (2.15 g), yield 78%.

NMR, δ (ppm): 3.73 (3H, s), 3.85 (2H, s, br), 6.64 (1H, t, J=72 Hz), 6.82 (1H, d, J=8 Hz), 7.04 (1H, d, J=10 Hz).

EXAMPLE 8

Preparation of 4-chloro-3-(2,4-dichloro-5-hydrophenyl)-1-methyl-5-methylthio-1H-pyrazole (compound No. 2)

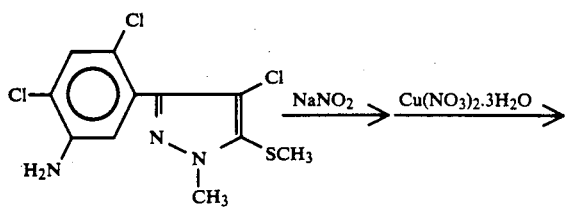

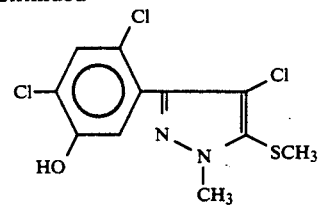

A solution of sodium nitrite (1.33 g) in 4.5 ml water was added dropwised to a 5° C. or lower temperature solution of 4-chloro-3-(5-amino-2,4-dichlorophenyl)-1-methyl-5-methylthio-1H-pyrazole (5.67 g, 17 mmoles) in 20 ml 50% sulfuric acid while maintaining the reaction temperature between −5° and +5° C. After the addition was finished, the reaction mixture was further stirred for 20 minutes at 0–5° C. Then the resulting solution was removed into a 1-l Elenmeyer flask, and a 40% aqueous copper nitrate solution (about 100 g of a total of 318.8 g) was first added dropwise to the former solution kept at temperatures of 0–10° C., and secondly the remainder copper nitrate solution was added dropwise. After stirring of the whole mixture for 30 minutes at room temperature, cuprous oxide (2.51 g, 17 mmoles) was added in limited amounts, conducting the reaction for 1 hour at room temperature. Then the resulting solution was poured into ice-cold water, and the objective product was extracted with ethyl acetate. The extract solution was washed with water and concentrated. The residue was purified by recrystallization from methylene chloride, giving crystals (2.61 g) of the title compound, m.p. 163.2° C., yield 46.4%.

EXAMPLE 9

Preparation of 4-chloro-3-(2,4-dichloro-5-mercaptophenyl)-1-methyl-5-methylthio-1H-pyrazole (compound No. 15)

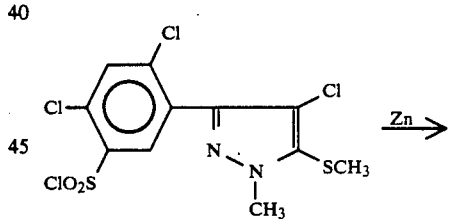

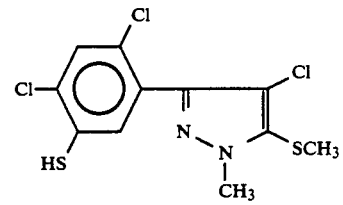

A mixture of 4-chloro-3-(5-chlorosulfonyl-2,4-dichlorophenyl)-1-methyl-5-methylthio-1H-pyrazole (7.71 g, 19 mmoles), 80 ml glacial acetic acid, and zinc dust (24.8 g, 380 mmoles) was subjected to reaction under reflux for 3.5 hours. The resulting solution was poured into ice-cold water, and the objective product was extracted with ethyl acetate. The extract solution was washed with water, dehydrated, and concentrated, giving the title compound (5.75 g) as oily matter, yield 89.1%.

nD (24.3° C.): 1.6303

EXAMPLE 10

Preparation of 4-chloro-3-[4-chloro-2-fluoro-5-(2-propynylthio)-phenyl]-1-methyl-5-methylthio-1H-pyrazole (compound No. 221)

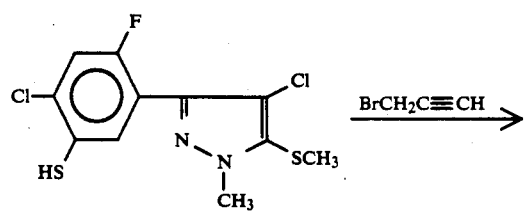

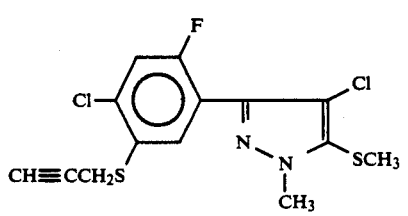

A mixture of 4-chloro-3-(4-chloro-2-fluoro-5-mercaptophenyl)-1-methyl-5-methylthio-1H-pyrazole (0.60 g, 1.86 mmoles), 30 ml acetone, a $K_2CO_3$ powder (2.04 mmoles), and propargyl bromide (2.23 mmoles), was subjected to reaction under reflux for 2 hours. Then the resulting solution was filtered to remove acetone-insoluble matter and the filtrate was concentrated and purified by silica gel column chromatography, giving crystals (0.54 g) of the title compound, m.p. 93–96° C., yield 80.5%.

EXAMPLE 11

Preparation of 4-chloro-3-2,4-dichloro-5-(2-propynyloxy)phenyl]-1-methyl-5-methylthio-1H-pyrazole (compound No. 5)

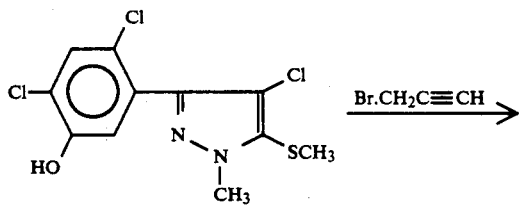

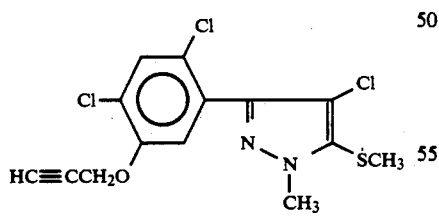

A mixture of 4-chloro-3-(2,4-dichloro-5-hydroxyphenyl)-1-methyl-5-methylthio-1H-pyrazole (2.00 g, 6.2 mmoles), 20 ml acetone, anhydrous $K_2CO_3$ (1.28 g, 9.3 mmoles), and propargyl bromide (1.10 g, 9.3 mmoles) was subjected to reaction under reflux for 2 hours. Then the resulting solution was filtered to remove acetone-insoluble matter. The filtrate was concentrated and purified by silica gel column chromatography, giving crystals (1.89 g) of the title compound, m.p. 71.5–72.5° C., yield 84.3%.

EXAMPLE 12

Preparation of ethyl 2-[5-(4-chloro-1-methyl-5-methylthio-1H-pyrazol-3-yl)-2,4-dichloro-phenoxy]propionate (compound No. 11)

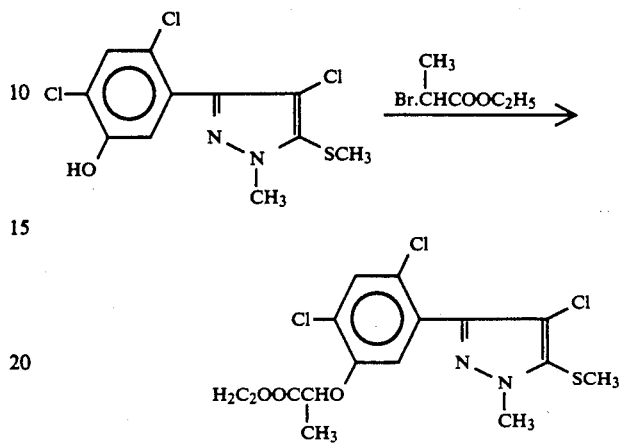

A mixture of 4-chloro-3-(2,4-dichloro-5-hydroxyphenyl)-1-methyl-5-methylthio-1H-pyrazole (3.50 g, 10.8 mmoles), 50 ml acetone, anhydrous $K_2CO_3$, and ethyl 2-bromopropionate (2.06 g, 11.4 mmoles) was subjected to reaction under reflux for 2 hours. Then the resulting solution was filtered to remove acetone-insoluble matter, and the filtrate was concentrated and purified by silica gel column chromatography, give the title compound as oily substance; Yield 70.0 nD(28.8° C.): 1.5763.

EXAMPLE 13

Preparation of 2-[5-(4-chloro-1-methyl-5-methylthio-1H-pyrazol-3-yl)-2,4-dichlorophenylthio]propionic acid (compound No. 25)

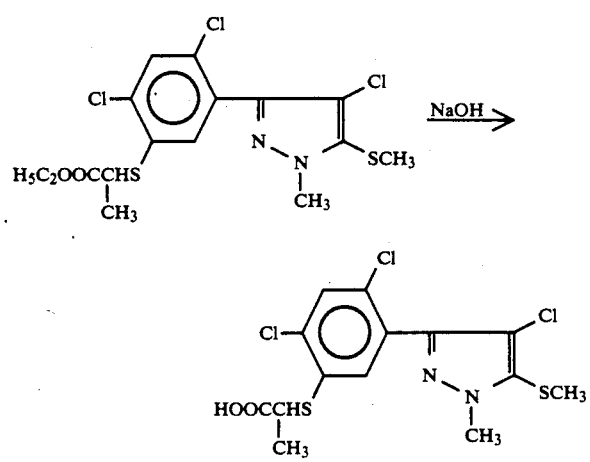

After addition of NaOH (0.31 g, in pellet form, 95% content) to a solution of ethyl 2-[5-(4-chloro-1-methyl-5-methylthio-1H-pyrazol-3-yl)-2,4-dichlorophenylthio]propionate (2.28 g, 5.18 mmoles) in 50 ml ethanol, several drops of water added, thereby conducting the reaction for 3 hours at room temperature. Then the solvent was removed by evaporation of the resulting solution under reduced pressure. Water and ethyl acetate were added to the residue and the formed aqueous layer was separated. The aqueous layer was acidified with hydrochloric acid. The objective product was extracted from the aqueous layer with ethyl acetate. The extract solution was washed with water, dehydrated, and evaporated to dryness, giving crystals (1.74 g) of the title compound, m.p. 180.0° C., yield 81.6%.

EXAMPLE 14

Preparation of 4-chloro-3-(2,4-dichloro-5-dimethylaminophenyl)-5-difluoromethyl-thio-1-methyl-1H-pyrazole (compound No. 207)

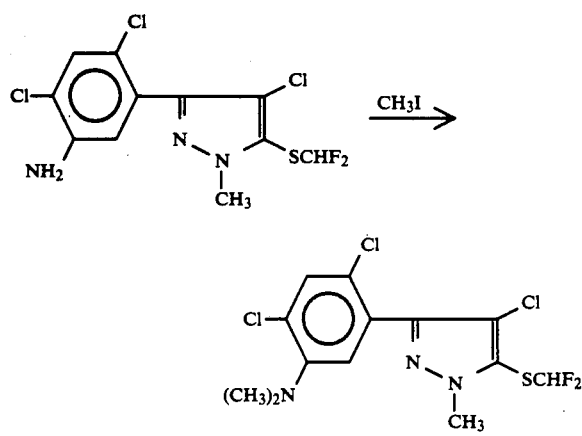

A mixture of 3-(5-amino-2,4-dichlorophenyl)-4-chloro-5-difluoromethylthio-1-methyl-1H-pyrazole (0.72 g, 2 mmoles), 15 ml sulforane, NaHCO$_3$ (0.18 g, 2.2 mmoles), and methyl iodide (0.34 g, 2.4 mmoles) was subjected to reaction at 80° C. for 16 hours. Then the resulting mixture was poured into water and the objective product was extracted with ether. The extract solution was washed with water, dehydrated, and evaporated to dryness, giving the title compound (0.62 g) in paste form, yield 80.2%.

nD (21.6° C.): 1.5838

EXAMPLE 15

Preparation of N,N-dimethyl 2-[5-(4-chloro-5-difluoromethoxy-1-methyl-1H-pyrazol-3-yl)-2,4-dichlorophenoxy]propionamide (compound No. 110)

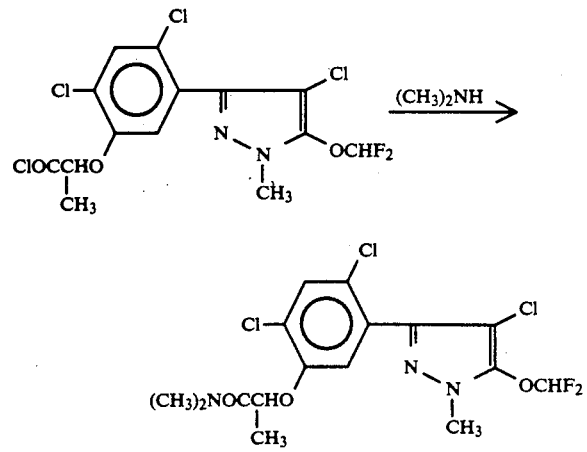

A solution of 2-[5-(4-chloro-5-difluoromethoxy-1-methyl-1H-pyrazole-3-yl)-2,4-dichlorophenoxy]propionyl chloride (0.80 g, 1.78 mmoles) in 20 ml anhydrous tetrahydrofuran was added dropwise to a solution of 50% dimethylamine (0.32 g, 3.56 mmoles) in 20 ml tetrahydrofuran at room temperature to react the pyrazole derivative with dimethylamine. After the addition was finished, the reaction was continued further for 1 hour. Then ethyl acetate was added to the reaction product solution, and the mixture was washed with water. The separated organic layer was dehydrated, concentrated under reduced pressure, and purified by silica gel chromatography, giving crystals (0.24 g) of the title compound, m.p. 148.9° C., yield 27%.

EXAMPLE 16

Preparation of 4-chloro-3-(2,4-dichloro-5-methylaminosulfonylaminophenyl)-5-difluoromethoxy-1-methyl-1H-pyrazole (compound No. 149)

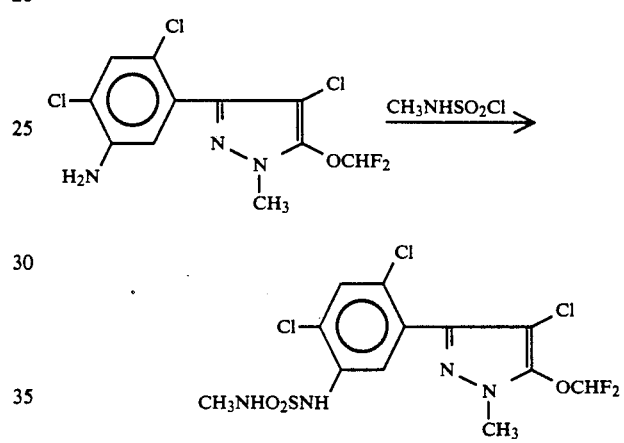

N-Methylaminosulfonyl chloride (0.22 g, 1.67 mmoles) was added dropwise to a solution of 3-(5-amino-2,4-dichlorophenyl)-4-chloro-5-difluoromethoxy-1-methyl-1H-pyrazole (0.44 g, 1.28 mmoles) and triethylamine (0.17 g, 1.67 mmoles) in 20 ml anhydrous tetrahydrofuran under cooling with ice to react with the pyrazole derivative. After the addition was finished, the reaction was continued further for 2 hours. Then ethyl acetate was added to the reaction product solution, and the mixture was washed with water. The separated organic layer was dehydrated, concentrated, and purified by recrystallization from a n-hexane-ether mixture, giving the title compound (0.40 g), m.p. 133.0° C., yield 71.7%.

EXAMPLE 17

Preparation of 5-(4-chloro-5-difluoromethoxy-1-methyl-1H-pyrazol-3-yl)-N-methyl-2,4-dichlorobenzenesulfonamide (compound No. 164)

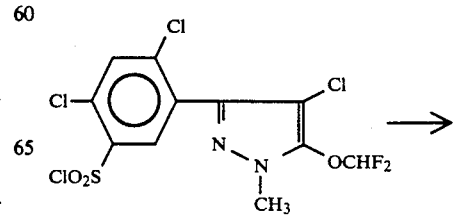

-continued

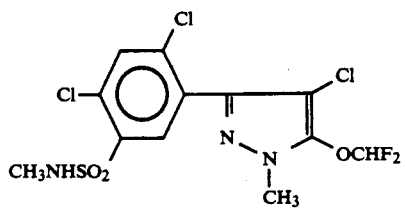

A solution of 4-chloro-3-(5-chlorosulfonyl-2,4-dichlorophenyl)-5-difluoromethoxy-1-methyl-1H-pyrazole (0.43 g, 1 mmole) in 2 ml tetrahydrofuran was added dropwise to a 40% aqueous methylamine solution dissolved in 20 ml tetrahydrofuran to react the pyrazole derivative with methylamine. After the addition was finished, the reaction was continued further for 30 minutes at room temperature. Then ethyl acetate was added to the reaction product solution to extract the objective product. The extract solution was washed with water, dehydrated, and evaporated to dryness, giving the title compound (0.42 g) in paste form, yield 100%.

$n_D$ (17.9° C.) 1.5461

EXAMPLE 18

Preparation of 2-[5-(4-chloro-5-difluoromethoxy-1-methyl-1H-pyrazol-3-yl)-2,4-dichloroanilino]isopropylammonium propionate (compound No. 160)

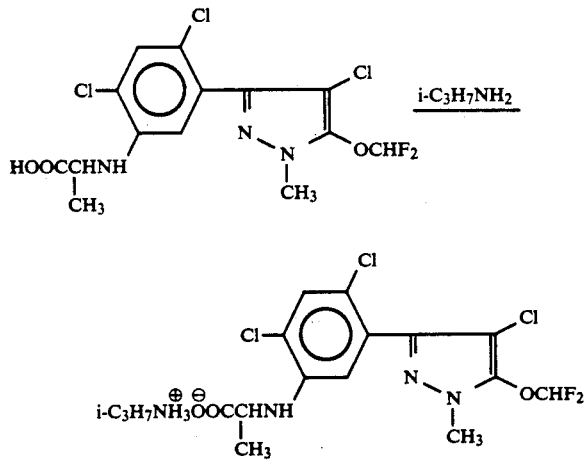

Isopropylamine (0.05 g, 0.88 mmole) was added to a solution of 2-[5-(4-chloro-5-difluoromethoxy-1-methyl-1H-pyrazol-3-yl)-2,4-dichloroanlino]propionic acid (0.33 g, 0.8 mmole) in 20 ml tetrahydrofuran, thereby being reacted with the acid for 30 minutes at room temperature. Thereafter the solvent was removed from the reaction product solution by evaporation under reduced pressure, giving the title compound quantitatively (100% yield) as oily matter.

NMR δ (ppm); 1.12 (6H, d), 1.48 (3H, d), 2.60–3.30 (1H, m), 3.73 (3H, s), 3.91 (1H, q), 6.55 (1H, s), 6.68 (1H, s) 7.73 (1H, s), 7.98 (3H, s).

EXAMPLE 19

Preparation of ethyl 2-[5-(4-chloro-1,2-dimethyl-5-methylthio-1H-pyrazolium-3-yl)-2,4-dichlorophenoxy]propionatemethyl sulfate (compound No. 215)

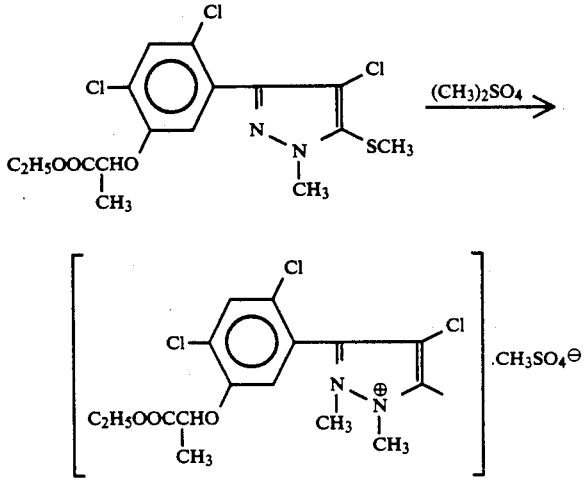

Dimethyl sulfate (0.13 g, 1.04 mmoles) was added to a solution of ethyl 2-[5-(4-chloro-1-methyl-5-methylthio-1H-pyrazol-3-yl)-2,4-dichlorophenoxy]propionate (0.22 g, 0.52 mmole) in 20 ml benzene, thereby being reacted with the pyrazole derivative under reflux for 5 days. Thereafter the solvent was removed from the reaction product solution by evaporation under reduced pressure. The residue was dissolved in ethyl acetate, the solution was washed with a small amount of water, and the organic layer was dehydrated and evaporated to dryness, giving the title quateranry salt in paste form, yield 52.6%.

$n_D$ (25.7° C.): 1.5548

The present inventive 3-(substituted phenyl)pyrazole derivatives represented by formula (I) and salts thereof are capable of controlling annual and perennial weeds grown in paddy fields, upland fields, orchards, and swamps, such as barnyardgrass (*Echinochloa Crus-galli Beauv.*, an annual gramineous grass which is a typical weed strongly injurious, grown in paddy fields), Mizugayatsuri (*Cyperus serotinus Rottb.*, a perennial weed of Cyperaceae family, grown in swamps, ditches and paddy fields), Urikawa (*Sagittaria pygmaea Miq.*, an injurious perennial weed of Alismataceae family, grown in swamps, ditches, and paddy fields), Hotarui (*Scirpus juncoides Roxb.* subsp. *juncoides.*, a perennial cyperaceous weed grown in swamps, water ways, and paddy fields), wild oats (*Avena fatua L.*, an annual gramineous grass grown in plains, highlands, and upland fields), large crabgrass (*Digitaraia adscendcus Henr.*, an annual gramineous grass which is a typical strongly injurious weed grown in upland fields and orchards), Curlydock (*Rumex japonicus Houtt*, a perennial polygonaceous weed grown in upland fields and on roadsides), umbrella sedge (*Cyperus Iria L.*, an annual cyperaceous weed grown in upland fields and on roadsides), Redroot pigweed (*Amaranthus vetroflexus L.*, an annual weed of Amaranthaceae family grown in upland fields, roadsides, and vacant lands), Cleavers (*Galium aparine L echinospermon*, a strongly injurious annual weed of Rubiaceae family grown in upland fields), Bridseye Speedwell (*Veronica persica L.*, a strongly injurious weed of Scrophulariaceae family grown in upland fields and orchards), Scented mayweed (*Matricaria chamomilla L.*, injurious composite weed grown in upland fields), velvetleaf (*Abutilon theophrasti L.*, a strongly injurious weed of Malvaceae family grown in upland fields), cocklebur (*Xanthium strumarium L.*, a strongly injurious annual composite weed grown in upland fields), and tall morningglory (*Ipomoea purpurea Voigt*, a strongly injurious weed of Convolvulaceae family grown in upland fields).

Since the 3-(substituted phenyl)pyrazole derivatives of formula (I) and salts thereof exhibit excellent controlling effect on weeds before or immediately after germination, characteristic physiological activities of these compounds can be manifested by treating fields with the derivative or the salt before or after planting of useful plants therein (including fields where useful plants are already planted) in the stage prior to weed emergence or in the period from the initial stage to the middle stage of weed growth. However, the applications of the present inventive herbicides are not limited such forms as stated above. The present herbicides can be applied to control not only weeds in paddy fields or upland fields but also general weeds grown in other places, for example, reaped fields, temporarily non-cultivated paddy fields and upland fields, ridges between paddy fields, agricultural pathways, waterways, lands constructed for pasture, graveyards, parks, roads, playgrounds, unoccupied areas around buildings, reclaimed lands, railways, and forests. It is most desirable in economy as well to treat these areas with the present herbicides, before the end of the initial stage of weed growth, but the treatment is not limited to this but can be carried out in the middle stage of weed growth.

The 3-(substituted phenyl)pyrazole derivative of formula (I) or salt thereof, when applied as a herbicide, is generally made up, according to the customary procedure for preparing agricultural chemicals, into a form convenient to use. That is, the pyrazole derivative or salt thereof is blended with a suitable inert carrier and if necessary, further with an adjuvant, in proper ratios, and the mixture is made up into a suitable form of preparation, e.g. a suspension, emulsifiable concentrate, solution, wettable powder, granules, dust, or tablets, through dissolution, disersion, suspension, mixing, impregnation, adsorption, or sticking. In the present invention, either solid or liquid inert carriers may be used. Suitable materials as solid carriers include soybean flour, cereal flour, wood flour, bark flour, saw dust, powdered tobacco stalks, powdered walnut shells, bran, powdered cellulose, extraction residues of vegetables, powdered synthetic polymers or resins; clays (e.g. kaolin, bentonite, and acid clay), talcs (e.g. talc and pyrophyllite), silica powders or flakes (e.g. diatomaceous earth, silica sand, mica and white carbon, i.e. highly dispersed silicic acid, also called finely divided hydrated silica or hydrated silicic acid), activated carbon, powdered sulfur, powdered pumice, calcined diatomaceous earth, ground brick, fly ash, sand, calcium carbonate powder, calcium phosphate powder, and other inorganic or mineral powders, chemical fertilizers (e.g. ammonium sulfate, ammonium nitrate, urea, and ammonium chloride) and compost. These materials may be used alone or in combination.

Suitable materials as liquid carriers include liquids which themselves have solvent power as well as liquids which do not have solvent power but can disperse active ingredients with the aid of adjuvants. Typical examples of such liquids, which may be used alone or in combination, are water, alcohols (including methanol, ethanol, isopropanol, butanol, and ethylene glycol), ketones (including acetone, methyl ethyl ketone, methyl isobutyl ketone, diisobutyl ketone, and cyclohexanone), ethers (including ethyl ether, dioxane, Cellosolve, dipropyl ether, and tetrahydrofuran), aliphatic hydrocarbons (including gasoline, and mineral oils), aromatic hydrocarbons (including benzene, toluene, xylene, solvent naphtha, and alkylnaphthalenes), halogenated hydrocarbons (including dichloroethane, chloroform and carbon tetrachloride), esters (including ethyl acetate, diisopropyl phthalate, dibutyl phthalate, and dioctyl phthalate), amides (including dimethylformamide, diethylformamide, and dimethylacetamide), nitriles (including acetonitrile), and dimethylsulfoxide.

The following materials are cited as typical examples of the adjuvants which may be used alone or in combination or may not be used at all.

For the purpose of emulsifying, dispersing, solubilizing, and/or wetting active ingredients, there may be used surface active agents such as polyoxyethylene alkyl ethers, polyoxyethylene alkylaryl ethers, polyoxyethylene higher fatty acid esters, polyoxyethylene resinates, polyoxyethylene sorbitan monolaurate, polyoxyethylene sorbitan monooleate, alkylarylsulfonates, naphthalenesulfonic acid condensation products, ligninsulfonates, and higher alcohol sulfate esters.

For the purpose of stabilizing the dispersion of active ingredients, tackifying and/or binding them, there may be used adjuvants, for example, casein, gelatin, starch, methylcellulose, carboxymethylcellulose, gum arabic, polyvinyl alcohol, turpentine, bran oil, bentonite, and ligninsulfonates.

For the purpose of improving flow properties of solid herbicidal products there may be used adjuvants, for example, waxes, stearates, and alkyl phosphates.

Adjuvants, e.g. naphthalenesulfonic acid condensation products and polyphosphates, can be used as peptizers in dispersible herbicidal products.

Adjuvants, e.g. silicone oils, can also the used as defoaming agents.

The content of active ingredients may be varied as occasion demands; the suitable contents are from 0.01 to 50% by weight for preparing, for example, dusts or granules as well as emulsifiable concentrates or wettable powders.

For destroying various weeds or inhibiting their growth, the herbicidal composition containing the 3-(substituted phenyl)pyrazole derivative of formula (I) or salt thereof as an active ingredient is applied as such or after being properly diluted with or suspended in water or other media, in amounts effective for destroying weeds or inhibiting their growth, to the foliage and stalks of the weeds or to soil in the area where the emergence or growth of weeds is undesirable.

The amount of the present herbicidal composition to be used, depending upon various factors, e.g. the purpose of application, object weeds, emergence or growth states of weeds and crops, emergence tendency of weeds, weather, environmental conditions, form of the herbicidal composition, mode of the application, type or state of the application locus, and time of the application, is chosen properly according to the purpose from the range of 1.0 g to 10 Kg, in terms of the amount of active ingredient, per hectare.

When the present herbicidal composition is applied to paddy fields or upland fields, it is desirable to choose such low doses as not to injure crops but to destroy weeds or control their growth. When the composition is applied to non-farming areas, suitable doses of active ingredient for destroying the weeds are chosen from amounts of 100 g/hectare and more.

The present herbicidal composition can be applied jointly with other herbicides for the purpose of expanding both the range of controllable weed species and the period of time when effective applications are possible or for the purpose of reducing the dosage.

The following examples illustrate herbicidal effects and formulations of the present inventive herbicidal composition without limiting the scope of the invention.

TEST EXAMPLE 1

Herbicidal effect on paddy field weeds of pre-emergence stage

Pots (1/10,000-are) were filled with soil to simulate a paddy field, then plated separately with seeds of barnyardgrass, konagi (Monochoria vaginalis (Burm.f.) Presl var plantaginae), and hotarui and with tubers of arrowhead, which are all injurious weeds grown in paddy fields, and were conditioned so that the seeds might become in pre-emergence stage.

Soil in each pot was sprayed with each of solutions containing compounds (listed in Table 1) of the present invention as active ingredients at a predetermined concentration. 21 Days later, the herbicidal effect was examined, the percentages of killed weeds were calculated in comparison with those on the untreated soil, and the herbicidal activity was judged and the chemical injury of a rice plant was examined at the same time and judged according to the following criterion:

| | Herbicidal activity |
|---|---|
| Rating | Percentage of killed weed |
| 5 | 95% or more |
| 4 | 70–95% (exclusive) |
| 3 | 50–70% (exclusive) |
| 2 | 30–50% (exclusive) |
| 1 | 10–30% (exclusive) |
| 0 | less than 10% |

| | Phytotoxicity |
|---|---|
| Rating | Degree of phytotoxicity |
| 0 | No phytotoxicity |
| 1 | Browning occurs but disappears in the initial growth stage, growth inhibition is not observed. |
| 2 | Browning and distinct growth inhibition are observed but normal conditions are soon restored. |
| 3 | Browning and growth inhibition are remarkable and the restoration is slow. |
| 4 | Browning and growth inhibition are remarkable and some of the rice plants are killed. |
| 5 | All the rice plants were killed. |

For comparison the following compounds were also tested.

Compound A: 3-phenyl-5-methylthiopyrazole, described on page 3 in Japanese Patent Application Kokai No. Sho. 51-91861; compound B: described in Example 1 on page 4 in the same patent application; compound C: compound No. 8 described in Japanese Patent Application Kokai No. Sho. 54-70270; compound D: compound No. 159 described on page 9 in Japanese Patent Application Kokai No. Sho. 55-9062.

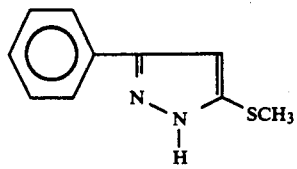

Compound A.

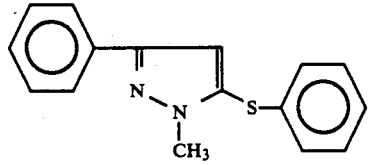

Compound B.

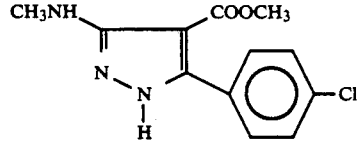

Compound C.

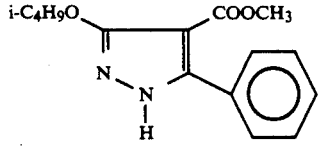

Compound D.

Results of the test are shown in Table 5.

TABLE 5

| Comp'd No. | Amount of active ingredient Kg/ha | Phyto- toxicity rice | Pre-emergence treatment | | |
|---|---|---|---|---|---|
| | | | Barnyard- grass | Hatarui | Konagi |
| 86 | 0.8 | 5 | 5 | 5 | 5 |
| | 0.1 | 4 | 5 | 5 | 5 |
| 87 | 0.8 | 5 | 5 | 5 | 5 |
| | 0.1 | 4 | 5 | 5 | 5 |
| 117 | 0.8 | 4 | 5 | 5 | 5 |
| | 0.1 | 3 | 5 | 5 | 5 |
| 119 | 0.8 | 4 | 5 | 5 | 5 |
| | 0.1 | 2 | 5 | 5 | 5 |
| 152 | 0.8 | 3 | 5 | 5 | 5 |
| | 0.1 | 2 | 5 | 5 | 5 |
| 153 | 0.8 | 5 | 5 | 5 | 5 |
| | 0.1 | 3 | 5 | 5 | 5 |
| 253 | 0.8 | 5 | 5 | 5 | 5 |
| | 0.1 | 1 | 3 | 5 | 5 |
| 256 | 0.8 | 5 | 5 | 5 | 5 |
| | 0.1 | 4 | 5 | 5 | 5 |
| 257 | 0.8 | 5 | 5 | 5 | 5 |
| | 0.1 | 3 | 5 | 5 | 5 |
| 258 | 0.8 | 5 | 5 | 5 | 5 |
| | 0.1 | 4 | 5 | 5 | 5 |
| 259 | 0.8 | 5 | 4 | 5 | 5 |
| | 0.1 | 3 | 2 | 4 | 4 |
| 260 | 0.8 | 5 | 5 | 5 | 5 |
| | 0.1 | 3 | 2 | 5 | 5 |
| 268 | 0.8 | 5 | 5 | 5 | 5 |
| | 0.1 | 3 | 5 | 5 | 5 |
| 269 | 0.8 | 5 | 5 | 5 | 5 |
| | 0.1 | 3 | 2 | 5 | 5 |
| 275 | 0.8 | 5 | 5 | 5 | 5 |
| | 0.1 | 2 | 3 | 5 | 5 |
| 344 | 0.8 | 5 | 5 | 5 | 5 |
| | 0.1 | 4 | 5 | 5 | 5 |
| 346 | 0.8 | 5 | 5 | 5 | 5 |
| | 0.1 | 4 | 5 | 5 | 5 |
| 359 | 0.8 | 5 | 5 | 5 | 5 |
| | 0.1 | 3 | 5 | 5 | 5 |
| 368 | 0.8 | 5 | 5 | 5 | 5 |

TABLE 5-continued

| Comp'd No. | Amount of active ingredient Kg/ha | Phyto- toxicity rice | Pre-emergence treatment | | |
|---|---|---|---|---|---|
| | | | Barnyard- grass | Hatarui | Konagi |
| | 0.1 | 2 | 5 | 5 | 5 |
| 369 | 0.8 | 5 | 5 | 5 | 5 |
| | 0.1 | 3 | 5 | 5 | 5 |
| 370 | 0.8 | 5 | 5 | 5 | 5 |
| | 0.1 | 2 | 2 | 5 | 5 |
| 371 | 0.8 | 5 | 5 | 5 | 5 |
| | 0.1 | 2 | 1 | 5 | 5 |
| A | 5 | 0 | 0 | 0 | 0 |
| B | 5 | 0 | 0 | 2 | 0 |
| C | 5 | 0 | 0 | 0 | 0 |
| D | 5 | 0 | 0 | 0 | 0 |

As shown in table 5, the present 3-(substituted phenyl) pyrazole derivatives or salt thereof, represented by the general formula (I), exhibit more excellent controlling effects of weeds than comparative compound A, B, C or D at pre-emergence treatment in paddy fields. Even when the derivatives exhibit both herbicidal activity on weeds and phytotoxicity on crops at the same dosage, however, by the selection of a proper lower dosage, sufficient herbicidal activity is retained but phytotoxicity on crops is reduced remarkably.

TEST EXAMPLE 2

Herbicidal effect on paddy field weeds of post-emergence stage

Pots (1/10,000-are) were filled with soil to simulate a paddy field, then planted separately with seeds of barnyardgrass and hotarui and with tubers of mizugayatsuri and urikawa, which are all injurious weeds grown in paddy fields, and were conditioned so that these weeds might grow to 1-leaf stage.

Soil in each pot was sprayed with each of solutions containing compounds (listed in Table 1) of the present invention as active ingredient at a predetermined concentration. 21 Days later, the herbicidal effect was examined, the percentages of killed weeds were calculated in the same manner as in Test Example 1, and the phytotoxicity of a rice plant also examined and judged according the criterior shown in Test Example 1.

Results of the test are shown in Table 6.

TABLE 6

| Comp'd No. | Amount of active ingredient Kg/ha | Phyto- toxicity rice | Effect of past-emergence treatment | | | |
|---|---|---|---|---|---|---|
| | | | Barnyardgrass | Hotarui | Mizugaytsuri | Urikawa |
| 2 | 5 | 1 | 4 | 1 | 0 | 0 |
| 3 | 5 | 2 | 5 | 4 | 2 | 3 |
| 4 | 5 | 5 | 5 | 5 | 3 | 4 |
| | 0.8 | 3 | 5 | 3 | 1 | 2 |
| 5 | 5 | 5 | 5 | 5 | 5 | 5 |
| | 0.8 | 4 | 5 | 4 | 4 | 3 |
| 6 | 5 | 3 | 5 | 4 | 5 | 3 |
| 7 | 5 | 4 | 5 | 4 | 3 | 1 |
| | 0.8 | 2 | 4 | 1 | 0 | 1 |
| 8 | 5 | 3 | 5 | 4 | 1 | 2 |
| 9 | 5 | 5 | 5 | 5 | 5 | 5 |
| | 0.8 | 4 | 5 | 4 | 5 | 5 |
| 10 | 5 | 5 | 5 | 5 | 5 | 5 |
| | 0.8 | 5 | 5 | 4 | 5 | 5 |
| | 0.1 | 2 | 5 | 2 | 3 | 4 |
| 11 | 5 | 5 | 5 | 5 | 5 | 5 |
| | 0.8 | 4 | 5 | 4 | 5 | 4 |
| | 0.1 | 2 | 5 | 3 | 5 | 2 |
| 12 | 5 | 5 | 5 | 5 | 5 | 5 |
| | 0.8 | 4 | 5 | 4 | 5 | 5 |
| | 0.1 | 0 | 3 | 2 | 0 | 3 |
| 13 | 5 | 5 | 5 | 5 | 5 | 5 |
| | 0.8 | 4 | 5 | 4 | 5 | 5 |
| | 0.1 | 1 | 3 | 1 | 0 | 2 |
| 14 | 5 | 5 | 5 | 5 | 5 | 5 |
| | 0.8 | 5 | 5 | 4 | 5 | 5 |
| 16 | 5 | 1 | 3 | 2 | 0 | 3 |
| 18 | 5 | 1 | 4 | 2 | 1 | 3 |
| 19 | 5 | 2 | 5 | 2 | 0 | 3 |
| 20 | 5 | 1 | 5 | 1 | 0 | 2 |
| 21 | 5 | 2 | 5 | 2 | 5 | 3 |
| 23 | 5 | 2 | 5 | 3 | 2 | 4 |
| 25 | 5 | 5 | 5 | 5 | 3 | 5 |
| | 0.8 | 3 | 4 | 2 | 3 | 4 |
| 26 | 5 | 5 | 5 | 5 | 4 | 5 |
| | 0.8 | 2 | 3 | 3 | 3 | 4 |
| 27 | 5 | 4 | 5 | 5 | 4 | 5 |
| | 0.8 | 3 | 3 | 2 | 3 | 3 |
| 28 | 5 | 5 | 5 | 5 | 2 | 5 |
| | 0.8 | 2 | 5 | 2 | 0 | 4 |
| 29 | 5 | 5 | 5 | 5 | 4 | 5 |
| | 0.8 | 3 | 5 | 3 | 2 | 4 |
| 30 | 5 | 5 | 5 | 5 | 2 | 5 |
| | 0.8 | 2 | 5 | 2 | 0 | 4 |
| 31 | 5 | 5 | 5 | 5 | 4 | 5 |
| | 0.8 | 3 | 5 | 2 | 1 | 4 |
| 32 | 5 | 5 | 5 | 5 | 2 | 5 |
| | 0.8 | 2 | 5 | 2 | 0 | 4 |
| 33 | 5 | 5 | 5 | 5 | 2 | 5 |

TABLE 6-continued

| Comp'd No. | Amount of active ingredient Kg/ha | Phyto-toxicity rice | Effect of past-emergence treatment | | | |
|---|---|---|---|---|---|---|
| | | | Barnyardgrass | Hotarui | Mizugaytsuri | Urikawa |
| | 0.8 | 2 | 5 | 2 | 0 | 4 |
| 34 | 5 | 5 | 5 | 5 | 2 | 5 |
| | 0.8 | 2 | 5 | 2 | 0 | 4 |
| 35 | 5 | 5 | 5 | 5 | 2 | 5 |
| | 0.8 | 2 | 5 | 2 | 0 | 4 |
| 37 | 5 | 5 | 5 | 4 | 5 | 5 |
| | 0.8 | 2 | 5 | 2 | 2 | 5 |
| 38 | 5 | 2 | 5 | 4 | 3 | 5 |
| 41 | 5 | 1 | 5 | 2 | 2 | 4 |
| 42 | 5 | 1 | 4 | 2 | 0 | 2 |
| 43 | 5 | 1 | 5 | 2 | 4 | 5 |
| 44 | 5 | 1 | 5 | 2 | 1 | 4 |
| 45 | 5 | 1 | 5 | 2 | 1 | 4 |
| 46 | 5 | 1 | 5 | 2 | 2 | 4 |
| 47 | 5 | 1 | 2 | 1 | 2 | 4 |
| 48 | 5 | 1 | 5 | 2 | 1 | 4 |
| 49 | 5 | 5 | 5 | 5 | 5 | 5 |
| | 0.8 | 3 | 5 | 5 | 3 | 5 |
| 50 | 5 | 5 | 5 | 5 | 5 | 4 |
| | 0.8 | 4 | 5 | 3 | 3 | 4 |
| | 0.1 | 1 | 5 | 2 | 0 | 2 |
| 51 | 5 | 5 | 5 | 5 | 5 | 5 |
| | 0.8 | 2 | 0 | 1 | 0 | 3 |
| 52 | 5 | 3 | 5 | 4 | 4 | 4 |
| 53 | 5 | 4 | 5 | 5 | 5 | 5 |
| | 0.8 | 2 | 3 | 1 | 0 | 2 |
| 54 | 5 | 2 | 5 | 4 | 5 | 3 |
| 55 | 5 | 2 | 5 | 2 | 2 | 2 |
| 57 | 5 | 0 | 2 | 2 | 0 | 1 |
| 59 | 5 | 2 | 5 | 3 | 4 | 2 |
| 62 | 5 | 3 | 5 | 3 | 2 | 5 |
| | 0.8 | 1 | 2 | 0 | 0 | 5 |
| 63 | 5 | 3 | 5 | 3 | 2 | 5 |
| | 0.8 | 1 | 2 | 0 | 0 | 5 |
| 64 | 5 | 5 | 5 | 5 | 2 | 5 |
| | 0.8 | 2 | 5 | 3 | 0 | 5 |
| 66 | 5 | 3 | 3 | 2 | 1 | 5 |
| 67 | 5 | 3 | 5 | 3 | 2 | 5 |
| | 0.8 | 1 | 2 | 0 | 0 | 5 |
| 68 | 5 | 5 | 3 | 2 | 1 | 5 |
| | 0.8 | 2 | 0 | 0 | 0 | 5 |
| 69 | 5 | 5 | 5 | 5 | 3 | 5 |
| | 0.8 | 2 | 5 | 3 | 0 | 5 |
| 71 | 5 | 5 | 5 | 5 | 5 | 5 |
| | 0.8 | 5 | 5 | 5 | 5 | 4 |
| | 0.1 | 2 | 5 | 3 | 3 | 1 |
| 72 | 5 | 5 | 5 | 5 | 5 | 5 |
| | 0.8 | 3 | 3 | 5 | 5 | 2 |
| 73 | 5 | 2 | 4 | 4 | 4 | 2 |
| 74 | 5 | 5 | 5 | 4 | 4 | 4 |
| | 0.8 | 3 | 3 | 1 | 0 | 1 |
| 75 | 5 | 2 | 0 | 2 | 4 | 0 |
| 76 | 5 | 2 | 4 | 4 | 5 | 2 |
| 77 | 5 | 2 | 5 | 4 | 1 | 2 |
| 78 | 5 | 1 | 5 | 2 | 2 | 0 |
| 81 | 5 | 5 | 5 | 5 | 5 | 5 |
| | 0.8 | 3 | 5 | 5 | 5 | 5 |
| 82 | 5 | 5 | 5 | 5 | 5 | 5 |
| | 0.8 | 3 | 5 | 4 | 5 | 5 |
| 83 | 5 | 3 | 5 | 4 | 4 | 5 |
| 84 | 5 | 5 | 5 | 5 | 5 | 5 |
| | 0.8 | 3 | 5 | 4 | 5 | 5 |
| 85 | 5 | 2 | 5 | 3 | 5 | 5 |
| 86 | 5 | 5 | 5 | 5 | 5 | 5 |
| | 0.1 | 3 | 5 | 0 | 5 | 1 |
| 87 | 5 | 5 | 5 | 5 | 5 | 5 |
| | 0.1 | 3 | 5 | 3 | 5 | 4 |
| 88 | 5 | 5 | 5 | 5 | 5 | 5 |
| | 0.8 | 3 | 5 | 4 | 5 | 5 |
| 89 | 5 | 5 | 5 | 5 | 5 | 5 |
| | 0.8 | 4 | 5 | 5 | 5 | 5 |
| 90 | 5 | 5 | 5 | 5 | 5 | 5 |
| | 0.8 | 3 | 5 | 3 | 3 | 3 |
| 91 | 5 | 5 | 5 | 5 | 5 | 5 |
| | 0.1 | 3 | 4 | 3 | 5 | 5 |
| 92 | 0.8 | 5 | 5 | 5 | 5 | 5 |
| | 0.1 | 3 | 4 | 5 | 5 | 5 |
| 93 | 0.8 | 5 | 5 | 5 | 5 | 5 |

TABLE 6-continued

| Comp'd No. | Amount of active ingredient Kg/ha | Phyto-toxicity rice | Effect of past-emergence treatment | | | |
|---|---|---|---|---|---|---|
| | | | Barnyardgrass | Hotarui | Mizugaytsuri | Urikawa |
| | 0.1 | 2 | 2 | 2 | 0 | 5 |
| 94 | 0.8 | 5 | 5 | 5 | 5 | 5 |
| | 0.1 | 3 | 5 | 4 | 5 | 5 |
| 95 | 5 | 5 | 5 | 5 | 5 | 5 |
| | 0.8 | 4 | 5 | 5 | 5 | 5 |
| 96 | 5 | 5 | 5 | 5 | 5 | 5 |
| | 0.8 | 4 | 5 | 5 | 5 | 5 |
| 97 | 0.8 | 5 | 5 | 5 | 5 | 5 |
| | 0.1 | 2 | 4 | 4 | 5 | 5 |
| 98 | 0.8 | 5 | 5 | 5 | 5 | 5 |
| | 0.1 | 2 | 4 | 3 | 5 | 5 |
| 99 | 5 | 5 | 5 | 5 | 5 | 5 |
| | 0.8 | 3 | 5 | 5 | 5 | 5 |
| 100 | 5 | 5 | 5 | 5 | 5 | 5 |
| | 0.8 | 4 | 5 | 5 | 5 | 5 |
| 101 | 0.8 | 5 | 5 | 5 | 5 | 5 |
| | 0.1 | 2 | 3 | 1 | 0 | 5 |
| 102 | 5 | 5 | 5 | 5 | 5 | 5 |
| | 0.8 | 4 | 5 | 5 | 5 | 5 |
| 103 | 0.8 | 5 | 5 | 5 | 5 | 5 |
| | 0.1 | 2 | 0 | 0 | 1 | 5 |
| 104 | 0.8 | 5 | 5 | 5 | 5 | 5 |
| | 0.1 | 2 | 0 | 0 | 0 | 5 |
| 105 | 0.8 | 5 | 5 | 5 | 5 | 5 |
| | 0.1 | 4 | 4 | 4 | 1 | 5 |
| 106 | 0.8 | 5 | 5 | 5 | 5 | 5 |
| | 0.1 | 3 | 4 | 0 | 0 | 5 |
| 108 | 5 | 5 | 5 | 5 | 5 | 5 |
| | 0.1 | 3 | 4 | 4 | 5 | 5 |
| 109 | 5 | 5 | 5 | 5 | 5 | 5 |
| | 0.1 | 3 | 5 | 5 | 5 | 5 |
| 110 | 5 | 5 | 5 | 5 | 5 | 5 |
| | 0.1 | 4 | 5 | 3 | 0 | 5 |
| 111 | 5 | 5 | 5 | 4 | 5 | 5 |
| | 0.8 | 2 | 5 | 2 | 4 | 3 |
| 112 | 0.8 | 5 | 5 | 5 | 5 | 5 |
| | 0.1 | 2 | 5 | 0 | 4 | 1 |
| 113 | 5 | 5 | 5 | 5 | 3 | 5 |
| | 0.8 | 3 | 5 | 2 | 1 | 5 |
| 114 | 5 | 5 | 5 | 5 | 5 | 5 |
| | 0.8 | 3 | 5 | 5 | 5 | 5 |
| 115 | 5 | 5 | 5 | 5 | 4 | 5 |
| | 0.8 | 2 | 5 | 2 | 3 | 4 |
| 116 | 5 | 5 | 5 | 5 | 5 | 5 |
| | 0.1 | 3 | 5 | 0 | 5 | 0 |
| 117 | 5 | 5 | 5 | 5 | 5 | 5 |
| | 0.8 | 2 | 5 | 3 | 5 | 5 |
| 118 | 5 | 5 | 5 | 3 | 2 | 5 |
| | 0.8 | 3 | 5 | 0 | 0 | 5 |
| 119 | 5 | 5 | 5 | 5 | 5 | 5 |
| | 0.8 | 2 | 5 | 3 | 5 | 3 |
| 120 | 5 | 3 | 5 | 3 | 5 | 5 |
| 121 | 5 | 5 | 5 | 5 | 5 | 5 |
| | 0.8 | 3 | 5 | 3 | 5 | 5 |
| 122 | 5 | 4 | 5 | 5 | 5 | 5 |
| | 0.8 | 3 | 5 | 3 | 3 | 4 |
| 123 | 5 | 5 | 5 | 5 | 5 | 5 |
| | 0.1 | 2 | 5 | 3 | 0 | 5 |
| 125 | 5 | 5 | 5 | 5 | 5 | 5 |
| | 0.8 | 4 | 5 | 5 | 5 | 5 |
| | 0.1 | 3 | 4 | 3 | 3 | 4 |
| 126 | 5 | 5 | 5 | 5 | 5 | 5 |
| | 0.8 | 5 | 5 | 5 | 5 | 5 |
| | 0.1 | 3 | 5 | 2 | 1 | 4 |
| 127 | 5 | 5 | 5 | 5 | 5 | 5 |
| | 0.8 | 5 | 5 | 4 | 5 | 5 |
| | 0.1 | 3 | 3 | 3 | 2 | 4 |
| 128 | 5 | 5 | 5 | 5 | 5 | 5 |
| | 0.8 | 5 | 5 | 5 | 4 | 5 |
| | 0.1 | 3 | 1 | 2 | 0 | 4 |
| 129 | 5 | 5 | 5 | 5 | 5 | 5 |
| | 0.8 | 5 | 5 | 5 | 5 | 5 |
| | 0.1 | 5 | 5 | 4 | 2 | 5 |
| 130 | 0.8 | 5 | 5 | 5 | 5 | 5 |
| | 0.1 | 2 | 5 | 5 | 2 | 5 |
| 131 | 5 | 5 | 5 | 5 | 5 | 5 |
| | 0.8 | 3 | 5 | 2 | 0 | 3 |
| 132 | 5 | 5 | 5 | 5 | 5 | 5 |

TABLE 6-continued

| Comp'd No. | Amount of active ingredient Kg/ha | Phyto-toxicity rice | Effect of past-emergence treatment | | | |
|---|---|---|---|---|---|---|
| | | | Barnyardgrass | Hotarui | Mizugaytsuri | Urikawa |
| | 0.8 | 3 | 4 | 3 | 1 | 3 |
| 133 | 5 | 5 | 5 | 5 | 5 | 5 |
| | 0.8 | 5 | 5 | 5 | 5 | 5 |
| | 0.1 | 3 | 5 | 0 | 5 | 5 |
| 134 | 5 | 5 | 5 | 5 | 5 | 5 |
| | 0.8 | 5 | 5 | 5 | 5 | 5 |
| | 0.1 | 3 | 5 | 5 | 0 | 5 |
| 135 | 5 | 5 | 5 | 5 | 5 | 5 |
| | 0.8 | 5 | 5 | 5 | 5 | 5 |
| | 0.1 | 3 | 5 | 4 | 3 | 5 |
| 136 | 5 | 5 | 5 | 4 | 5 | 5 |
| | 0.8 | 5 | 5 | 3 | 5 | 5 |
| | 0.1 | 3 | 5 | 2 | 2 | 5 |
| 137 | 5 | 5 | 5 | 5 | 5 | 5 |
| | 0.8 | 5 | 5 | 5 | 5 | 5 |
| | 0.1 | 3 | 5 | 5 | 3 | 5 |
| 138 | 5 | 5 | 5 | 5 | 5 | 5 |
| | 0.8 | 3 | 5 | 5 | 5 | 5 |
| 139 | 5 | 5 | 5 | 5 | 5 | 5 |
| | 0.8 | 5 | 5 | 5 | 5 | 5 |
| | 0.1 | 3 | 5 | 2 | 0 | 5 |
| 140 | 5 | 5 | 5 | 5 | 5 | 5 |
| | 0.8 | 5 | 5 | 5 | 5 | 5 |
| | 0.1 | 3 | 5 | 5 | 5 | 5 |
| 141 | 5 | 5 | 5 | 5 | 5 | 5 |
| | 0.8 | 5 | 5 | 5 | 5 | 5 |
| | 0.1 | 4 | 5 | 3 | 0 | 5 |
| 142 | 5 | 5 | 5 | 5 | 5 | 5 |
| | 0.8 | 5 | 5 | 5 | 5 | 5 |
| | 0.1 | 3 | 5 | 0 | 3 | 4 |
| 143 | 5 | 5 | 5 | 5 | 5 | 5 |
| | 0.8 | 5 | 5 | 5 | 5 | 5 |
| | 0.1 | 3 | 5 | 3 | 0 | 5 |
| 144 | 5 | 4 | 5 | 4 | 5 | 5 |
| | 0.8 | 3 | 5 | 4 | 5 | 4 |
| 145 | 5 | 5 | 5 | 5 | 5 | 5 |
| | 0.8 | 5 | 5 | 5 | 5 | 5 |
| | 0.1 | 3 | 5 | 2 | 0 | 4 |
| 146 | 5 | 2 | 5 | 4 | 5 | 5 |
| 147 | 5 | 2 | 5 | 5 | 5 | 5 |
| 148 | 5 | 5 | 5 | 5 | 5 | 5 |
| | 0.8 | 3 | 5 | 5 | 5 | 5 |
| 149 | 5 | 5 | 5 | 5 | 5 | 5 |
| | 0.8 | 3 | 5 | 5 | 5 | 5 |
| 150 | 5 | 5 | 5 | 5 | 5 | 5 |
| | 0.8 | 4 | 5 | 3 | 4 | 5 |
| | 0.1 | 2 | 5 | 2 | 2 | 5 |
| 151 | 5 | 5 | 5 | 5 | 5 | 5 |
| | 0.8 | 5 | 5 | 5 | 5 | 5 |
| | 0.1 | 3 | 5 | 1 | 0 | 3 |
| 152 | 5 | 5 | 5 | 5 | 5 | 5 |
| | 0.8 | 3 | 5 | 5 | 3 | 5 |
| 153 | 5 | 5 | 5 | 5 | 5 | 5 |
| | 0.8 | 5 | 5 | 5 | 5 | 5 |
| | 0.1 | 3 | 5 | 2 | 3 | 3 |
| 154 | 5 | 3 | 5 | 4 | — | 5 |
| 155 | 5 | 5 | 5 | 5 | 5 | 5 |
| | 0.8 | 3 | 4 | 2 | 5 | 5 |
| 156 | 5 | 5 | 5 | 5 | 5 | 5 |
| | 0.8 | 2 | 4 | 2 | 5 | 5 |
| 157 | 5 | 5 | 5 | 5 | 5 | 5 |
| | 0.8 | 3 | 5 | 5 | 5 | 5 |
| 158 | 5 | 5 | 5 | 5 | 3 | 5 |
| | 0.8 | 3 | 5 | 4 | 1 | 5 |
| 159 | 5 | 5 | 5 | 5 | 2 | 5 |
| | 0.8 | 3 | 4 | 3 | 0 | 4 |
| 160 | 5 | 5 | 5 | 3 | 2 | 5 |
| | 0.8 | 3 | 5 | 0 | 0 | 5 |
| 161 | 5 | 5 | 5 | 5 | 5 | 5 |
| | 0.8 | 5 | 5 | 5 | 4 | 5 |
| | 0.1 | 2 | 5 | 4 | 2 | 5 |
| 162 | 5 | 5 | 5 | 5 | 5 | 5 |
| | 0.8 | 4 | 5 | 5 | 5 | 5 |
| | 0.1 | 3 | 5 | 3 | 5 | 5 |
| 163 | 0.8 | 5 | 5 | 5 | 5 | 5 |
| | 0.1 | 3 | 5 | 5 | 3 | 5 |
| 164 | 5 | 5 | 5 | 5 | 5 | 5 |
| | 0.8 | 5 | 5 | 5 | 5 | 5 |

TABLE 6-continued

| Comp'd No. | Amount of active ingredient Kg/ha | Phyto-toxicity rice | Effect of past-emergence treatment | | | |
|---|---|---|---|---|---|---|
| | | | Barnyardgrass | Hotarui | Mizugaytsuri | Urikawa |
| | 0.1 | 2 | 5 | 3 | 0 | 5 |
| 165 | 5 | 3 | 5 | 5 | 4 | 4 |
| 166 | 5 | 3 | 5 | 4 | 5 | 4 |
| 167 | 5 | 5 | 5 | 5 | 2 | 5 |
| | 0.8 | 3 | 5 | 3 | 0 | 5 |
| 168 | 5 | 5 | 5 | 5 | 4 | 5 |
| | 0.8 | 3 | 5 | 2 | 2 | 4 |
| 169 | 5 | 5 | 5 | 3 | 5 | 5 |
| | 0.8 | 2 | 5 | 2 | 5 | 3 |
| 170 | 5 | 5 | 5 | 2 | 2 | 5 |
| | 0.8 | 2 | 4 | 0 | 0 | 5 |
| 171 | 5 | 3 | 5 | 0 | 4 | 5 |
| 172 | 5 | 3 | 5 | 4 | 5 | 5 |
| 173 | 5 | 5 | 5 | 2 | 5 | 5 |
| | 0.8 | 2 | 4 | 0 | 4 | 4 |
| 174 | 5 | 2 | 5 | 5 | 5 | 5 |
| 175 | 5 | 3 | 5 | 5 | 5 | 5 |
| 176 | 5 | 3 | 3 | 2 | 1 | 5 |
| 177 | 5 | 2 | 5 | 3 | 5 | 5 |
| 178 | 5 | 2 | 5 | 3 | 5 | 4 |
| 179 | 5 | 5 | 5 | 3 | 4 | 2 |
| | 0.8 | 2 | 5 | 0 | 2 | 0 |
| 180 | 5 | 3 | 5 | 2 | 2 | 5 |
| 181 | 5 | 2 | 5 | 4 | 5 | 2 |
| 182 | 5 | 5 | 5 | 5 | 5 | 5 |
| | 0.8 | 3 | 5 | 4 | 5 | 5 |
| 183 | 5 | 5 | 5 | 4 | 5 | 5 |
| | 0.8 | 3 | 5 | 4 | 0 | 5 |
| 184 | 5 | 2 | 5 | 3 | 5 | 3 |
| 185 | 5 | 3 | 5 | 4 | 5 | 5 |
| 186 | 5 | 2 | 5 | 4 | 5 | 5 |
| 187 | 5 | 1 | 5 | 2 | 4 | 0 |
| 188 | 5 | 5 | 5 | 2 | 4 | 2 |
| | 0.8 | 2 | 5 | 0 | 2 | 0 |
| 189 | 0.8 | 5 | 5 | 5 | 3 | 5 |
| | 0.1 | 1 | 4 | 0 | 1 | 1 |
| 190 | 5 | 5 | 5 | 5 | 5 | 5 |
| | 0.8 | 2 | 5 | 3 | 5 | 5 |
| 191 | 5 | 5 | 5 | 5 | 3 | 5 |
| | 0.8 | 3 | 4 | 4 | — | 5 |
| 192 | 5 | 5 | 5 | 5 | 3 | 5 |
| | 0.8 | 3 | 4 | 3 | 1 | 5 |
| 193 | 5 | 3 | 3 | 2 | 1 | 4 |
| 194 | 5 | 5 | 5 | 5 | 5 | 5 |
| | 0.8 | 3 | 3 | 3 | 5 | 5 |
| 195 | 5 | 4 | 5 | 5 | 5 | 5 |
| | 0.8 | 3 | 3 | 3 | 3 | 4 |
| 196 | 5 | 5 | 5 | 5 | 5 | 5 |
| | 0.8 | 2 | 3 | 2 | 2 | 3 |
| 197 | 5 | 5 | 5 | 5 | 5 | 5 |
| | 0.8 | 3 | 5 | 5 | 3 | 5 |
| 198 | 5 | 5 | 5 | 5 | 3 | 5 |
| | 0.8 | 3 | 5 | 2 | — | 5 |
| 199 | 5 | 5 | 5 | 5 | 5 | 5 |
| | 0.8 | 3 | 5 | 2 | 4 | 5 |
| 200 | 0.8 | 5 | 5 | 5 | 2 | 5 |
| | 0.1 | 1 | 3 | 0 | 0 | 5 |
| 201 | 0.8 | 5 | 5 | 3 | 5 | 5 |
| | 0.1 | 3 | 4 | 0 | 0 | 5 |
| 202 | 5 | 5 | 5 | 5 | 2 | 5 |
| | 0.8 | 2 | 3 | 2 | 0 | 5 |
| 203 | 5 | 5 | 5 | 4 | 4 | 5 |
| | 0.8 | 2 | 4 | 2 | 2 | 5 |
| 204 | 5 | 5 | 5 | 5 | 4 | 5 |
| | 0.8 | 3 | 5 | 2 | 2 | 5 |
| 205 | 5 | 2 | 5 | 4 | 0 | 4 |
| 206 | 5 | 5 | 5 | 5 | 4 | 5 |
| | 0.8 | 1 | 5 | 3 | 1 | 5 |
| 207 | 5 | 2 | 5 | 2 | 5 | 2 |
| 208 | 5 | 2 | 5 | 4 | 5 | 5 |
| 209 | 5 | 5 | 5 | 4 | 5 | 5 |
| | 0.8 | 2 | 5 | 1 | 5 | 5 |
| 210 | 5 | 3 | 5 | 5 | 5 | 5 |
| 211 | 5 | 5 | 5 | 5 | 5 | 5 |
| | 0.8 | 2 | 4 | 4 | 4 | 5 |
| 212 | 5 | 5 | 5 | 5 | 5 | 5 |
| | 0.8 | 3 | 5 | 5 | 5 | 5 |
| 213 | 5 | 4 | 5 | 4 | 3 | 3 |

TABLE 6-continued

| Comp'd No. | Amount of active ingredient Kg/ha | Phyto-toxicity rice | Effect of past-emergence treatment | | | |
|---|---|---|---|---|---|---|
| | | | Barnyardgrass | Hotarui | Mizugaytsuri | Urikawa |
| 214 | 5 | 4 | 5 | 3 | 3 | 3 |
| 216 | 5 | 5 | 5 | 5 | 2 | 5 |
| | 0.8 | 2 | 5 | 5 | 0 | 5 |
| 218 | 5 | 1 | 5 | 2 | 0 | 5 |
| 220 | 5 | 5 | 5 | 5 | 5 | 5 |
| | 0.8 | 3 | 5 | 5 | 3 | 5 |
| 221 | 5 | 5 | 5 | 5 | 5 | 2 |
| | 0.8 | 3 | 5 | 3 | 5 | 1 |
| 222 | 5 | 5 | 5 | 5 | 5 | 5 |
| | 0.8 | 3 | 5 | 4 | 5 | 5 |
| 223 | 5 | 5 | 5 | 5 | 5 | 5 |
| | 0.8 | 3 | 5 | — | 4 | 5 |
| 224 | 5 | 5 | 5 | 5 | 5 | 5 |
| | 0.8 | 3 | 5 | 5 | 5 | 5 |
| 225 | 5 | 2 | 5 | 2 | 4 | 2 |
| 226 | 5 | 2 | 5 | 2 | 5 | 2 |
| 227 | 0.8 | 3 | 4 | 5 | 5 | 5 |
| 228 | 5 | 5 | 5 | 5 | 5 | 5 |
| | 0.8 | 4 | 5 | 5 | 5 | 5 |
| | 0.1 | 3 | 5 | 1 | 2 | 5 |
| 229 | 5 | 5 | 5 | 5 | 5 | 5 |
| | 0.8 | 3 | 5 | 2 | 2 | 5 |
| 230 | 0.8 | 5 | 5 | 5 | 5 | 5 |
| | 0.1 | 2 | 2 | 3 | 0 | 5 |
| 231 | 0.8 | 5 | 4 | 5 | 5 | 5 |
| | 0.1 | 3 | 3 | 2 | 2 | 3 |
| 232 | 5 | 5 | 5 | 5 | 5 | 5 |
| | 0.8 | 3 | 5 | 5 | 5 | 5 |
| 233 | 0.8 | 5 | 5 | 5 | 5 | 5 |
| | 0.1 | 2 | 1 | 0 | 2 | 5 |
| 234 | 0.8 | 5 | 5 | 5 | 5 | 5 |
| | 0.1 | 2 | 0 | 0 | 0 | 5 |
| 235 | 0.8 | 5 | 5 | 5 | 5 | 5 |
| | 0.1 | 3 | 5 | 5 | 2 | 5 |
| 236 | 5 | 5 | 5 | 5 | 5 | 5 |
| | 0.8 | 2 | 5 | 5 | 5 | 5 |
| 237 | 0.8 | 5 | 5 | 5 | 5 | 5 |
| | 0.1 | 3 | 4 | 5 | 5 | 5 |
| 238 | 5 | 5 | 5 | 5 | 5 | 5 |
| | 0.8 | 4 | 5 | 5 | 5 | 5 |
| | 0.1 | 3 | 5 | 5 | 5 | 5 |
| 239 | 0.8 | 5 | 5 | 5 | 5 | 5 |
| | 0.1 | 3 | 5 | 5 | 5 | 5 |
| 240 | 5 | 5 | 5 | 5 | 5 | 5 |
| | 0.8 | 4 | 5 | 5 | 5 | 5 |
| | 0.1 | 3 | 5 | 5 | 0 | 5 |
| 241 | 0.8 | 3 | 5 | 5 | 5 | 5 |
| 242 | 0.8 | 5 | 5 | 5 | 5 | 5 |
| | 0.1 | 3 | 5 | 4 | 3 | 5 |
| 243 | 5 | 3 | 5 | 5 | 5 | 5 |
| | 0.8 | 1 | 5 | 4 | 5 | 5 |
| 244 | 5 | 5 | 5 | 5 | 5 | 5 |
| | 0.8 | 3 | 5 | 0 | 5 | 5 |
| 245 | 0.8 | 5 | 5 | 5 | 5 | 5 |
| | 0.1 | 1 | 5 | 0 | 5 | 5 |
| 246 | 5 | 3 | 2 | 4 | 2 | 3 |
| 247 | 0.8 | 5 | 5 | 5 | 5 | 5 |
| | 0.1 | 2 | 3 | 2 | 0 | 5 |
| 248 | 5 | 5 | 5 | 5 | 5 | 5 |
| | 0.8 | 4 | 5 | 5 | 5 | 5 |
| | 0.1 | 3 | 5 | 5 | 0 | 5 |
| 249 | 5 | 5 | 5 | 5 | 5 | 5 |
| | 0.8 | 4 | 5 | 5 | 5 | 5 |
| | 0.1 | 2 | 5 | 5 | 2 | 5 |
| 250 | 0.8 | 5 | 5 | 5 | 5 | 5 |
| | 0.1 | 3 | 2 | 3 | 1 | 5 |
| 251 | 0.8 | 5 | 5 | 5 | 5 | 5 |
| | 0.1 | 2 | 3 | 5 | 0 | 5 |
| 252 | 5 | 5 | 5 | 5 | 5 | 5 |
| | 0.8 | 3 | 5 | 5 | 5 | 5 |
| 253 | 0.8 | 5 | 5 | 5 | 5 | 5 |
| | 0.1 | 4 | 5 | 5 | 5 | 5 |
| 254 | 0.8 | 5 | 5 | 5 | 5 | 5 |
| | 0.1 | 4 | 5 | 5 | 2 | 5 |
| 255 | 0.2 | 5 | 5 | 5 | 5 | 5 |
| | 0.1 | 5 | 5 | 5 | 0 | 5 |
| 256 | 0.2 | 5 | 5 | 5 | 5 | 5 |
| | 0.1 | 3 | 5 | 5 | 5 | 5 |

TABLE 6-continued

| Comp'd No. | Amount of active ingredient Kg/ha | Phyto-toxicity rice | Effect of past-emergence treatment | | | |
|---|---|---|---|---|---|---|
| | | | Barnyardgrass | Hotarui | Mizugaytsuri | Urikawa |
| 257 | 0.2 | 5 | 5 | 5 | 5 | 5 |
| | 0.1 | 3 | 5 | 3 | 5 | 5 |
| 258 | 0.2 | 5 | 5 | 5 | 5 | 5 |
| | 0.1 | 4 | 5 | 5 | 5 | 5 |
| 259 | 0.8 | 5 | 5 | 5 | 5 | 5 |
| | 0.2 | 4 | 4 | 5 | 5 | 5 |
| | 0.1 | 3 | 3 | 0 | 5 | 5 |
| 260 | 0.8 | 5 | 5 | 5 | 5 | 5 |
| | 0.2 | 3 | 4 | 5 | 5 | 5 |
| 261 | 0.2 | 5 | 5 | 5 | 5 | 5 |
| | 0.1 | 3 | 3 | 5 | 5 | 5 |
| 262 | 0.2 | 5 | 5 | 5 | 5 | 5 |
| | 0.1 | 5 | 5 | 5 | 5 | 5 |
| 263 | 0.2 | 5 | 5 | 5 | 5 | 5 |
| | 0.1 | 5 | 5 | 5 | 5 | 5 |
| 264 | 0.2 | 5 | 5 | 5 | 5 | 5 |
| | 0.1 | 5 | 5 | 5 | 5 | 5 |
| 265 | 0.2 | 5 | 5 | 5 | 5 | 5 |
| | 0.1 | 5 | 5 | 5 | 5 | 5 |
| 266 | 0.2 | 5 | 5 | 5 | 5 | 5 |
| | 0.1 | 5 | 5 | 5 | 5 | 5 |
| 267 | 0.2 | 5 | 5 | 5 | 5 | 5 |
| | 0.1 | 4 | 5 | 5 | 5 | 5 |
| 268 | 0.8 | 5 | 5 | 5 | 5 | 5 |
| | 0.2 | 4 | 5 | 5 | 5 | 5 |
| | 0.1 | 3 | 5 | 5 | 5 | 5 |
| 269 | 0.8 | 5 | 5 | 5 | 5 | 5 |
| | 0.2 | 4 | 5 | 5 | 5 | 5 |
| | 0.1 | 3 | 5 | 3 | 5 | 5 |
| 270 | 0.8 | 5 | 5 | 5 | 5 | 5 |
| | 0.2 | 3 | 4 | 5 | 4 | 5 |
| 271 | 0.2 | 5 | 5 | 5 | 5 | 5 |
| | 0.1 | 3 | 5 | 5 | 5 | 5 |
| 272 | 0.2 | 5 | 5 | 5 | 5 | 5 |
| | 0.1 | 3 | 5 | 5 | 5 | 5 |
| 273 | 0.8 | 5 | 5 | 5 | 5 | 5 |
| | 0.2 | 4 | 5 | 5 | 5 | 5 |
| | 0.1 | 3 | 5 | 5 | 5 | 5 |
| 274 | 0.2 | 5 | 5 | 5 | 5 | 5 |
| | 0.1 | 4 | 5 | 5 | 5 | 5 |
| 275 | 0.8 | 5 | 5 | 5 | 5 | 5 |
| | 0.2 | 3 | 5 | 5 | 5 | 5 |
| | 0.1 | 2 | 5 | 3 | 3 | 5 |
| 276 | 5 | 5 | 5 | 5 | 5 | 5 |
| | 0.8 | 3 | 5 | 5 | 4 | 5 |
| 277 | 5 | 5 | 5 | 5 | 5 | 5 |
| | 0.8 | 2 | 5 | 5 | 4 | 5 |
| 278 | 5 | 5 | 5 | 5 | 2 | 5 |
| | 0.8 | 2 | 5 | 5 | 0 | 5 |
| 279 | 5 | 4 | 5 | 5 | 4 | 5 |
| | 0.8 | 1 | 5 | 4 | 2 | 4 |
| 280 | 5 | 5 | 5 | 5 | 5 | 5 |
| | 0.8 | 3 | 5 | 5 | 5 | 5 |
| 281 | 5 | 5 | 5 | 5 | 5 | 5 |
| | 0.8 | 3 | 4 | 4 | 4 | 5 |
| 282 | 5 | 5 | 5 | 5 | 5 | 5 |
| | 0.8 | 3 | 5 | 5 | 4 | 5 |
| 283 | 5 | 5 | 5 | 5 | 5 | 5 |
| | 0.8 | 3 | 5 | 5 | 5 | 5 |
| 284 | 5 | 5 | 5 | 5 | 5 | 5 |
| | 0.8 | 3 | 5 | 5 | 5 | 5 |
| 285 | 5 | 5 | 5 | 5 | 5 | 5 |
| | 0.8 | 4 | 5 | 5 | 5 | 5 |
| | 0.1 | 3 | 3 | 0 | 3 | 5 |
| 286 | 5 | 5 | 5 | 5 | 5 | 5 |
| | 0.8 | 4 | 4 | 3 | 5 | 5 |
| 287 | 5 | 5 | 5 | 5 | 5 | 5 |
| | 0.8 | 4 | 5 | 5 | 5 | 5 |
| | 0.1 | 3 | 5 | 3 | 5 | 5 |
| 288 | 0.8 | 5 | 5 | 5 | 5 | 5 |
| | 0.1 | 3 | 5 | 5 | 0 | 5 |
| 289 | 0.8 | 5 | 5 | 5 | 5 | 5 |
| | 0.1 | 3 | 5 | 4 | 0 | 5 |
| 290 | 5 | 5 | 5 | 5 | 5 | 5 |
| | 0.8 | 3 | 5 | 5 | 4 | 5 |
| 291 | 5 | 5 | 5 | 5 | 5 | 5 |
| | 0.8 | 3 | 5 | 5 | 5 | 5 |
| 292 | 5 | 5 | 5 | 5 | 5 | 5 |

TABLE 6-continued

| Comp'd No. | Amount of active ingredient Kg/ha | Phyto-toxicity rice | Effect of past-emergence treatment ||||
|---|---|---|---|---|---|---|
| | | | Barnyardgrass | Hotarui | Mizugaytsuri | Urikawa |
| | 0.8 | 4 | 5 | 5 | 4 | 5 |
| | 0.1 | 3 | 5 | 2 | 0 | 5 |
| 293 | 5 | 5 | 5 | 5 | 5 | 5 |
| | 0.8 | 4 | 5 | 5 | 5 | 5 |
| | 0.1 | 3 | 5 | 2 | 0 | 5 |
| 294 | 5 | 5 | 5 | 5 | 5 | 5 |
| | 0.8 | 4 | 5 | 5 | 5 | 5 |
| | 0.1 | 2 | 5 | 3 | 0 | 5 |
| 295 | 5 | 5 | 5 | 5 | 5 | 5 |
| | 0.8 | 3 | 5 | 5 | 5 | 5 |
| 296 | 5 | 5 | 5 | 5 | 5 | 5 |
| | 0.8 | 4 | 5 | 5 | 5 | 5 |
| | 0.1 | 2 | 4 | 0 | 0 | 5 |
| 297 | 5 | 5 | 5 | 5 | 5 | 5 |
| | 0.8 | 3 | 5 | 3 | 4 | 5 |
| 298 | 5 | 5 | 5 | 5 | 4 | 5 |
| | 0.8 | 3 | 5 | 3 | 2 | 5 |
| 299 | 5 | 5 | 5 | 5 | 5 | 5 |
| | 0.8 | 3 | 5 | 5 | 5 | 5 |
| 300 | 5 | 5 | 5 | 5 | 2 | 5 |
| | 0.8 | 3 | 4 | 4 | 0 | 5 |
| 301 | 5 | 5 | 5 | 5 | 5 | 5 |
| | 0.8 | 3 | 5 | 4 | 4 | 5 |
| 302 | 5 | 5 | 5 | 5 | 5 | 5 |
| | 0.8 | 4 | 5 | 5 | 5 | 5 |
| | 0.1 | 2 | 5 | 3 | 0 | 5 |
| 303 | 5 | 5 | 5 | 5 | 5 | 5 |
| | 0.8 | 3 | 5 | 5 | 3 | 5 |
| 304 | 0.8 | 5 | 5 | 5 | 5 | 5 |
| | 0.1 | 3 | 5 | 4 | 0 | 0 |
| 305 | 0.8 | 5 | 5 | 5 | 5 | 5 |
| | 0.1 | 3 | 5 | 3 | 0 | 5 |
| 306 | 5 | 5 | 5 | 5 | 5 | 5 |
| | 0.8 | 3 | 5 | 5 | 4 | 5 |
| 307 | 0.8 | 5 | 5 | 5 | 0 | 5 |
| | 0.1 | 3 | 3 | 2 | 0 | 0 |
| 308 | 5 | 5 | 5 | 5 | 5 | 5 |
| | 0.8 | 4 | 5 | 5 | 5 | 5 |
| | 0.1 | 3 | 5 | 5 | 3 | 5 |
| 309 | 5 | 5 | 5 | 5 | 5 | 5 |
| | 0.8 | 4 | 5 | 5 | 5 | 5 |
| | 0.1 | 3 | 5 | 5 | 0 | 5 |
| 310 | 5 | 5 | 5 | 5 | 5 | 5 |
| | 0.8 | 4 | 5 | 5 | 4 | 5 |
| | 0.1 | 2 | 5 | 0 | 0 | 5 |
| 311 | 5 | 5 | 5 | 5 | 5 | 5 |
| | 0.8 | 4 | 5 | 5 | 5 | 5 |
| | 0.1 | 2 | 4 | 3 | 0 | 5 |
| 312 | 5 | 5 | 5 | 5 | 2 | 4 |
| | 0.8 | 4 | 5 | 5 | 0 | 2 |
| | 0.1 | 2 | 3 | 3 | 0 | 0 |
| 313 | 5 | 5 | 5 | 5 | 5 | 5 |
| | 0.8 | 4 | 5 | 5 | 5 | 5 |
| | 0.1 | 3 | 5 | 3 | 0 | 5 |
| 314 | 5 | 5 | 5 | 5 | 5 | 5 |
| | 0.8 | 4 | 5 | 5 | 4 | 5 |
| | 0.1 | 2 | 3 | 0 | 4 | 5 |
| 315 | 5 | 5 | 5 | 5 | 5 | 5 |
| | 0.8 | 4 | 5 | 5 | 5 | 5 |
| | 0.1 | 3 | 5 | 5 | 0 | 5 |
| 316 | 5 | 5 | 5 | 5 | 5 | 5 |
| | 0.8 | 4 | 5 | 5 | 5 | 5 |
| | 0.1 | 3 | 5 | 4 | 0 | 5 |
| 317 | 5 | 5 | 5 | 5 | 5 | 5 |
| | 0.8 | 4 | 5 | 5 | 5 | 5 |
| | 0.1 | 2 | 5 | 4 | 0 | 5 |
| 318 | 5 | 5 | 5 | 5 | 5 | 5 |
| | 0.8 | 4 | 5 | 5 | 4 | 5 |
| | 0.1 | 2 | 3 | 2 | 0 | 5 |
| 319 | 5 | 5 | 5 | 5 | 5 | 5 |
| | 0.8 | 4 | 5 | 4 | 3 | 5 |
| | 0.1 | 2 | 4 | 2 | 3 | 5 |
| 320 | 5 | 5 | 5 | 5 | 5 | 5 |
| | 0.8 | 3 | 5 | 4 | 5 | 5 |
| 321 | 5 | 3 | 5 | 5 | 2 | 5 |
| | 0.8 | 1 | 5 | 2 | 0 | 5 |
| 322 | 0.8 | 5 | 4 | 5 | 5 | 5 |
| | 0.1 | 3 | 1 | 3 | 0 | 5 |

TABLE 6-continued

| Comp'd No. | Amount of active ingredient Kg/ha | Phyto-toxicity rice | Effect of past-emergence treatment | | | |
|---|---|---|---|---|---|---|
| | | | Barnyardgrass | Hotarui | Mizugaytsuri | Urikawa |
| 323 | 0.8 | 5 | 5 | 5 | 5 | 5 |
| | 0.1 | 5 | 5 | 5 | 5 | 5 |
| 324 | 0.8 | 5 | 5 | 5 | 5 | 5 |
| | 0.1 | 5 | 5 | 5 | 5 | 5 |
| 325 | 0.8 | 5 | 5 | 5 | 5 | 5 |
| | 0.1 | 5 | 5 | 5 | 5 | 5 |
| 326 | 0.8 | 5 | 5 | 5 | 5 | 5 |
| | 0.1 | 5 | 5 | 5 | 5 | 5 |
| 327 | 0.8 | 5 | 5 | 5 | 5 | 5 |
| | 0.1 | 5 | 5 | 5 | 5 | 5 |
| 328 | 0.8 | 5 | 5 | 5 | 5 | 5 |
| | 0.1 | 5 | 5 | 5 | 5 | 5 |
| 329 | 5 | 5 | 5 | 5 | 4 | 5 |
| | 0.8 | 2 | 5 | 3 | 2 | 5 |
| 330 | 5 | 3 | 5 | 4 | 2 | 5 |
| | 0.1 | 1 | 3 | 2 | 0 | 4 |
| 331 | 0.8 | 5 | 5 | 5 | 5 | 5 |
| | 0.1 | 2 | 3 | 5 | 0 | 5 |
| 332 | 0.8 | 5 | 5 | 5 | 5 | 5 |
| | 0.1 | 3 | 5 | 5 | 0 | 5 |
| 333 | 5 | 5 | 5 | 5 | 5 | 5 |
| | 0.8 | 2 | 5 | 5 | 5 | 5 |
| 334 | 5 | 5 | 5 | 5 | 5 | 5 |
| | 0.8 | 2 | 5 | 3 | 4 | 5 |
| 335 | 5 | 4 | 5 | 5 | 2 | 4 |
| | 0.8 | 1 | 5 | 4 | 0 | 2 |
| 336 | 5 | 5 | 5 | 5 | 5 | 5 |
| | 0.8 | 3 | 5 | 5 | 5 | 5 |
| 337 | 5 | 5 | 5 | 5 | 5 | 5 |
| | 0.8 | 3 | 5 | 4 | 5 | 5 |
| 338 | 5 | 5 | 5 | 5 | 5 | 5 |
| | 0.8 | 2 | 5 | 5 | 5 | 5 |
| 339 | 5 | 3 | 5 | 5 | 2 | 5 |
| | 0.8 | 1 | 5 | 3 | 0 | 4 |
| 340 | 5 | 4 | 5 | 5 | 4 | 5 |
| | 0.8 | 2 | 5 | 3 | 2 | 3 |
| 341 | 0.8 | 5 | 5 | 5 | 4 | 5 |
| | 0.2 | 2 | 4 | 4 | 2 | 5 |
| 342 | 0.2 | 5 | 5 | 5 | 5 | 5 |
| | 0.1 | 3 | 5 | 5 | 3 | 5 |
| 343 | 0.2 | 5 | 5 | 5 | 5 | 5 |
| | 0.1 | 5 | 5 | 5 | 3 | 5 |
| 344 | 0.2 | 5 | 5 | 5 | 5 | 5 |
| | 0.1 | 5 | 5 | 5 | 5 | 5 |
| 345 | 0.8 | 5 | 5 | 5 | 5 | 5 |
| | 0.2 | 4 | 5 | 5 | 5 | 5 |
| | 0.1 | 3 | 5 | 5 | 3 | 5 |
| 346 | 0.2 | 5 | 5 | 5 | 5 | 5 |
| | 0.1 | 4 | 5 | 5 | 5 | 5 |
| 347 | 0.2 | 5 | 5 | 5 | 5 | 5 |
| | 0.1 | 1 | 1 | 0 | 0 | 5 |
| 348 | 0.2 | 5 | 5 | 5 | 5 | 5 |
| | 0.1 | 5 | 5 | 3 | 3 | 5 |
| 349 | 0.2 | 5 | 5 | 5 | 5 | 5 |
| | 0.1 | 5 | 5 | 5 | 5 | 5 |
| 350 | 0.2 | 5 | 5 | 5 | 5 | 5 |
| | 0.1 | 3 | 5 | 4 | 0 | 5 |
| 351 | 0.8 | 3 | 5 | 5 | 5 | 5 |
| | 0.2 | 1 | 5 | 4 | 5 | 5 |
| 352 | 0.2 | 5 | 5 | 5 | 5 | 5 |
| | 0.1 | 5 | 5 | 5 | 5 | 5 |
| 353 | 0.2 | 5 | 5 | 5 | 5 | 5 |
| | 0.1 | 5 | 5 | 5 | 5 | 5 |
| 354 | 0.8 | 5 | 5 | 5 | 5 | 5 |
| | 0.2 | 3 | 5 | 4 | 5 | 5 |
| 355 | 0.2 | 5 | 5 | 5 | 5 | 5 |
| | 0.1 | 3 | 5 | 4 | 0 | 5 |
| 356 | 0.2 | 5 | 5 | 5 | 5 | 5 |
| | 0.1 | 3 | 4 | 2 | 0 | 5 |
| 357 | 0.2 | 5 | 5 | 5 | 5 | 5 |
| | 0.1 | 4 | 5 | 4 | 4 | 5 |
| 358 | 0.2 | 5 | 5 | 5 | 5 | 5 |
| | 0.1 | 3 | 4 | 0 | 0 | 5 |
| 359 | 0.8 | 5 | 5 | 4 | 5 | 5 |
| | 0.2 | 3 | 5 | — | 4 | 5 |
| 360 | 0.2 | 5 | 5 | 5 | 5 | 5 |
| | 0.1 | 3 | 5 | 5 | 5 | 5 |
| 361 | 0.2 | 5 | 5 | 5 | 5 | 5 |

TABLE 6-continued

| Comp'd No. | Amount of active ingredient Kg/ha | Phyto-toxicity rice | Effect of past-emergence treatment | | | |
|---|---|---|---|---|---|---|
| | | | Barnyardgrass | Hotarui | Mizugaytsuri | Urikawa |
| | 0.1 | 3 | 5 | 3 | 5 | 5 |
| 362 | 0.2 | 5 | 5 | 5 | 5 | 5 |
| | 0.1 | 3 | 5 | 3 | 3 | 5 |
| 363 | 0.2 | 5 | 5 | 5 | 5 | 5 |
| | 0.1 | 3 | 5 | 5 | 0 | 5 |
| 364 | 0.2 | 5 | 5 | 5 | 5 | 5 |
| | 0.1 | 3 | 5 | 3 | 0 | 5 |
| 365 | 0.2 | 5 | 5 | 5 | 5 | 5 |
| | 0.1 | 3 | 5 | 0 | 0 | 5 |
| 366 | 0.2 | 5 | 5 | 5 | 5 | 5 |
| | 0.1 | 3 | 5 | 5 | 3 | 5 |
| 367 | 0.8 | 5 | 5 | 5 | 5 | 5 |
| | 0.2 | 3 | 5 | 5 | 5 | 5 |
| 368 | 0.8 | 5 | 5 | 5 | 5 | 5 |
| | 0.1 | 3 | 5 | 2 | 0 | 5 |
| 369 | 0.2 | 5 | 5 | 5 | 5 | 5 |
| | 0.1 | 3 | 5 | 2 | 5 | 5 |
| 370 | 0.2 | 5 | 5 | 5 | 2 | 5 |
| | 0.1 | 1 | 3 | 3 | 0 | 4 |
| 371 | 0.2 | 5 | 5 | 5 | 2 | 5 |
| | 0.1 | 2 | 4 | 5 | 0 | 4 |
| 372 | 0.2 | 5 | 5 | 5 | 5 | 5 |
| | 0.1 | 5 | 5 | 5 | 5 | 4 |
| 373 | 0.8 | 5 | 5 | 5 | 5 | 5 |
| | 0.1 | 5 | 5 | 5 | 5 | 5 |
| 374 | 0.8 | 5 | 5 | 5 | 5 | 5 |
| | 0.1 | 5 | 5 | 5 | 5 | 5 |
| 375 | 0.8 | 5 | 5 | 5 | 5 | 5 |
| | 0.1 | 5 | 5 | 5 | 5 | 5 |
| 376 | 0.8 | 5 | 5 | 5 | 5 | 5 |
| | 0.1 | 5 | 5 | 5 | 5 | 5 |
| 377 | 0.2 | 5 | 5 | 5 | 5 | 5 |
| | 0.1 | 5 | 5 | 5 | 0 | 5 |
| 378 | 5 | 5 | 5 | 5 | 5 | 5 |
| | 0.8 | 2 | 5 | 2 | 4 | 5 |
| 379 | 5 | 5 | 5 | 5 | 3 | 5 |
| | 0.8 | 4 | 4 | 4 | — | 5 |
| 380 | 5 | 5 | 5 | 5 | 5 | 5 |
| | 0.8 | 2 | 5 | 5 | 4 | 5 |
| 381 | 5 | 5 | 5 | 5 | 5 | 5 |
| | 0.8 | 3 | 4 | 5 | 5 | 5 |
| 382 | 5 | 5 | 5 | 5 | 5 | 5 |
| | 0.8 | 3 | 5 | 5 | 5 | 5 |
| 383 | 5 | 5 | 5 | 5 | 5 | 5 |
| | 0.8 | 4 | 5 | 5 | 5 | 5 |
| | 0.1 | 1 | 5 | 0 | 0 | 5 |
| 384 | 5 | 5 | 5 | 5 | 5 | 5 |
| | 0.8 | 4 | 5 | 5 | 5 | 5 |
| 385 | 5 | 5 | 5 | 5 | 2 | 5 |
| | 0.8 | 5 | 5 | 5 | 0 | 5 |
| | 0.1 | 0 | 5 | 2 | 0 | 5 |
| 386 | 5 | 5 | 5 | 5 | 5 | 5 |
| | 0.8 | 3 | 5 | 4 | 2 | 5 |
| 387 | 5 | 5 | 5 | 3 | 5 | 5 |
| | 0.8 | 3 | 5 | 5 | 5 | 5 |
| 388 | 0.8 | 5 | 5 | 5 | 5 | 5 |
| | 0.1 | 2 | 4 | 3 | 0 | 5 |
| 389 | 5 | 5 | 5 | 5 | 5 | 5 |
| | 0.8 | 4 | 5 | 5 | 5 | 5 |
| | 0.1 | 2 | 5 | 5 | 0 | 5 |
| 390 | 5 | 5 | 5 | 5 | 5 | 5 |
| | 0.8 | 3 | 5 | 5 | 5 | 5 |
| 391 | 5 | 5 | 5 | 5 | 5 | 5 |
| | 0.8 | 3 | 5 | 4 | 5 | 5 |
| 392 | 5 | 4 | 5 | 5 | 2 | 5 |
| | 0.8 | 2 | 5 | 3 | 0 | 5 |
| 393 | 5 | 5 | 5 | 5 | 5 | 5 |
| | 0.8 | 4 | 4 | 5 | 5 | 5 |
| 394 | 5 | 5 | 5 | 5 | 2 | 5 |
| | 0.8 | 3 | 5 | 5 | 0 | 5 |
| 395 | 5 | 5 | 5 | 5 | 3 | 5 |
| | 0.8 | 4 | 5 | 5 | 0 | 5 |
| | 0.1 | 1 | 4 | 2 | 0 | 5 |
| 396 | 5 | 3 | 5 | 5 | 2 | 5 |
| | 0.8 | 1 | 3 | 2 | 0 | 5 |
| 397 | 5 | 5 | 5 | 5 | 5 | 5 |
| | 0.8 | 3 | 5 | 4 | 2 | 5 |
| 398 | 5 | 3 | 2 | 4 | 2 | 5 |

TABLE 6-continued

| Comp'd No. | Amount of active ingredient Kg/ha | Phyto- toxicity rice | Effect of past-emergence treatment | | | |
|---|---|---|---|---|---|---|
| | | | Barnyardgrass | Hotarui | Mizugaytsuri | Urikawa |
| | 0.8 | 1 | 0 | 2 | 0 | 5 |
| 399 | 5 | 5 | 5 | 5 | 2 | 5 |
| | 0.8 | 2 | 5 | 4 | 0 | 5 |
| 400 | 5 | 5 | 5 | 5 | 5 | 5 |
| | 0.8 | 2 | 5 | 5 | 5 | 5 |
| 401 | 5 | 5 | 5 | 5 | 5 | 5 |
| | 0.8 | 4 | 5 | 5 | 5 | 5 |
| 402 | 5 | 5 | 5 | 5 | 5 | 5 |
| | 0.8 | 4 | 5 | 5 | 5 | 5 |
| 403 | 0.2 | 5 | 5 | 4 | 5 | 5 |
| | 0.1 | 4 | 3 | 2 | 0 | 5 |
| 404 | 0.2 | 5 | 5 | 5 | 5 | 5 |
| | 0.1 | 5 | 5 | 5 | 0 | 5 |
| 405 | 0.2 | 5 | 5 | 4 | 5 | 5 |
| | 0.1 | 3 | 3 | 3 | 0 | 4 |
| 406 | 0.2 | 4 | 4 | 3 | 4 | 5 |
| | 0.1 | 3 | 3 | 0 | 0 | 3 |
| A | 5 | 0 | 0 | 0 | 0 | 0 |
| B | 5 | 0 | 2 | 0 | 0 | 0 |
| C | 5 | 0 | 0 | 0 | 0 | 0 |
| D | 5 | 0 | 0 | 0 | 0 | 0 |

As shown in table 6, the present 3-(substituted phenyl)pyrazole derivatives or salt thereof, represented by the general formula (I), exhibit more excellent controlling effects of weeds than comparative compound A, B, C or D at post-emergence treatment in paddy fields. Even when the derivatives exhibit both herbicidal activity on weeds and phytotoxicity on crops at the same dosage, however, by the selection of a proper lower dosage, sufficient herbicidal activity is retained but phytotoxicity on crops is reduced remarkably.

TEST EXAMPLE 3

Herbicidal effect on upland field weeds of pre-emergence stage.

Polyethylene vats of 10 cm W×20 cm L×5 cm depth were filled with soil, and planted separately with seeds of barnyardgrass, velvetleaf, cocklebur, jimsonweed, birdseye speedwell, cleavers, which are upland field weeds, and separately with seeds of soybean and wheat as upland field crops.

Soil in each pot was sprayed with each of solutions containing compounds (listed in Table 1) of the present invention as active ingredient at a predetermined concentration. 14 Days later, the herbicidal effect was examined, the percentages of killed weeds were calculated in the same manner as in Test Example 1, and the phytotoxicity of soybean and wheat plants were also examined and judged according the criterion shown in Test Example 1.

Results of the test are shown in Table 7.

TABLE 7

| Comp'd No. | Amount of active ingredient Kg/ha | Phytotoxicity | | Pre-emergence treatment | | | | | |
|---|---|---|---|---|---|---|---|---|---|
| | | wheat | soybean | barnyard- grass | velvet- leaf | cocklebur | jimsonweed | birdseye speedwell | cleavers |
| 3 | 5 | 1 | 0 | 5 | 5 | 5 | 5 | — | 5 |
| 4 | 5 | 2 | 1 | 5 | 5 | 0 | 4 | — | 5 |
| 5 | 5 | 3 | 0 | 5 | 4 | 2 | 5 | — | 5 |
| 6 | 5 | 1 | 2 | 5 | 3 | 0 | 2 | — | 3 |
| 7 | 5 | 0 | 1 | 4 | 4 | 0 | 2 | — | 2 |
| 8 | 5 | 0 | 0 | 3 | 3 | 0 | 1 | — | 1 |
| 9 | 5 | 4 | 4 | 5 | 5 | — | 5 | — | 5 |
| | 0.8 | 2 | 0 | 5 | 4 | 3 | 5 | — | — |
| 10 | 5 | 5 | 4 | 5 | 5 | 5 | 5 | — | 5 |
| | 0.8 | 3 | 2 | 3 | 5 | 5 | 5 | — | — |
| 11 | 5 | 5 | 5 | 5 | 4 | 4 | 5 | — | 5 |
| 12 | 5 | 4 | 4 | 5 | 4 | — | 5 | — | 5 |
| | 0.8 | 3 | 1 | 5 | 2 | — | 5 | — | — |
| 13 | 5 | 4 | 4 | 5 | 5 | 5 | 5 | — | 5 |
| | 0.8 | 3 | 1 | 5 | 5 | 5 | 5 | — | — |
| 14 | 5 | 5 | 3 | 5 | 5 | — | 5 | — | 5 |
| | 0.8 | 3 | 0 | 5 | 5 | — | 5 | — | — |
| 16 | 5 | 1 | — | 4 | 3 | 2 | 4 | — | 5 |
| 17 | 5 | 0 | 0 | 1 | 0 | 0 | 4 | — | 0 |
| 18 | 5 | 1 | 2 | 4 | 4 | 2 | 4 | — | 5 |
| 19 | 5 | 1 | 1 | 5 | — | 1 | 4 | — | 4 |
| 20 | 5 | 1 | 0 | 3 | 0 | 0 | 3 | — | 5 |
| 21 | 5 | 0 | 0 | 4 | 2 | 0 | 1 | — | 0 |
| 23 | 5 | 0 | 0 | 4 | 0 | 0 | 1 | — | 0 |
| 24 | 5 | 0 | 1 | 0 | 0 | 0 | 4 | — | 4 |
| 25 | 5 | 1 | 0 | 3 | 2 | 0 | 5 | — | 4 |
| 26 | 5 | 4 | 3 | 5 | 5 | — | 5 | — | 5 |
| | 0.8 | 2 | 1 | 4 | 4 | 0 | 4 | — | 4 |

TABLE 7-continued

| Comp'd No. | Amount of active ingredient Kg/ha | Phytotoxicity wheat | soybean | Pre-emergence treatment barnyard- grass | velvet- leaf | cocklebur | jimsonweed | birdseye speedwell | cleavers |
|---|---|---|---|---|---|---|---|---|---|
| 27 | 5 | 4 | 4 | 5 | 5 | — | 5 | — | 5 |
|  | 0.8 | 2 | 2 | 4 | 4 | — | 5 | — | 4 |
| 28 | 5 | 4 | 2 | 4 | 5 | — | 5 | — | 5 |
|  | 0.8 | 2 | 0 | 3 | 4 | 0 | 5 | — | 5 |
| 29 | 5 | 2 | 3 | 5 | — | 2 | 5 | — | 4 |
| 30 | 5 | 3 | 3 | 4 | 5 | — | 5 | — | 5 |
|  | 0.8 | 1 | 1 | 3 | 4 | 1 | 5 | — | 3 |
| 31 | 5 | 3 | 2 | 5 | 4 | 3 | 5 | — | 5 |
| 32 | 5 | 3 | 2 | 4 | 5 | — | 5 | — | 4 |
|  | 0.8 | 1 | 0 | 3 | 4 | 0 | 5 | — | 3 |
| 33 | 5 | 4 | 2 | 4 | 4 | — | 5 | — | 5 |
|  | 0.8 | 2 | 0 | 3 | 3 | 0 | 5 | — | 5 |
| 34 | 5 | 3 | 2 | 3 | 5 | — | 5 | — | 5 |
|  | 0.8 | 1 | 0 | 2 | 4 | 0 | 5 | — | 4 |
| 35 | 5 | 3 | 2 | 5 | 4 | — | 5 | — | 3 |
|  | 0.8 | 1 | 0 | 4 | 3 | 0 | 5 | — | 2 |
| 37 | 5 | 3 | 3 | 5 | 5 | 4 | 5 | — | 5 |
| 38 | 5 | 2 | 1 | 5 | 5 | 0 | 5 | — | 5 |
| 40 | 5 | 0 | 0 | 0 | 3 | 0 | 5 | — | 0 |
| 41 | 5 | 2 | 2 | 2 | 4 | — | 4 | — | 4 |
| 42 | 5 | 0 | 0 | 3 | 1 | 0 | 0 | — | 0 |
| 43 | 5 | 0 | 0 | 4 | 2 | 0 | 3 | — | 5 |
| 44 | 5 | 0 | 0 | 4 | 3 | 0 | 5 | — | 5 |
| 45 | 5 | 0 | 0 | 4 | 2 | 0 | 2 | — | 4 |
| 46 | 5 | 0 | 0 | 3 | 3 | 0 | 4 | — | 4 |
| 47 | 5 | 0 | 0 | 4 | 5 | 1 | 5 | — | 5 |
| 48 | 5 | 0 | 0 | 1 | 2 | 0 | 2 | — | 4 |
| 49 | 5 | 3 | 5 | 5 | 4 | 0 | 5 | — | 5 |
| 50 | 5 | 2 | 5 | 5 | 4 | — | 5 | — | 5 |
| 51 | 5 | 2 | 5 | 5 | 5 | 5 | 5 | — | 5 |
| 52 | 5 | 0 | 3 | 5 | 5 | — | 5 | — | 5 |
| 54 | 5 | 1 | 5 | 5 | 5 | 5 | 5 | — | 5 |
| 55 | 5 | 0 | 0 | 3 | 1 | 0 | 2 | — | 1 |
| 57 | 5 | 0 | 0 | 3 | 2 | 0 | 0 | — | 0 |
| 59 | 5 | 0 | 0 | 4 | 1 | 0 | 2 | — | 0 |
| 71 | 5 | 3 | 5 | 5 | 5 | — | 5 | — | 5 |
| 72 | 5 | 1 | 1 | 5 | 4 | 4 | 5 | — | 5 |
| 73 | 5 | 1 | 1 | 4 | 5 | 0 | 4 | — | 4 |
| 74 | 5 | 2 | 2 | 5 | 5 | 2 | 5 | — | 5 |
| 76 | 5 | 1 | 1 | 5 | 5 | 1 | 5 | — | 2 |
| 77 | 5 | 0 | 1 | 5 | 5 | — | 3 | — | 4 |
| 78 | 5 | 0 | 0 | 5 | 4 | 0 | 2 | — | 2 |
| 81 | 5 | 5 | 4 | 5 | 5 | 5 | 5 | — | 5 |
|  | 0.8 | 3 | 2 | 5 | 5 | 4 | 5 | — | — |
| 82 | 5 | 5 | 4 | 5 | 5 | 5 | 5 | — | 5 |
|  | 0.8 | 3 | 2 | 5 | 5 | 4 | 5 | — | — |
| 83 | 5 | 4 | 3 | 5 | 5 | — | 5 | — | 5 |
|  | 0.8 | 2 | 2 | 5 | 4 | 4 | 5 | — | 5 |
| 84 | 5 | 5 | 4 | 5 | 5 | 5 | 5 | — | 5 |
|  | 0.8 | 3 | 2 | 5 | 5 | 4 | 5 | — | — |
| 85 | 5 | 5 | 4 | 5 | 5 | 5 | 5 | — | 5 |
|  | 0.8 | 2 | 1 | 4 | 5 | 4 | 5 | — | 4 |
| 86 | 5 | 5 | 5 | 5 | 5 | 5 | 5 | — | 5 |
|  | 0.8 | 3 | 3 | 5 | 5 | 5 | 5 | — | 5 |
| 87 | 5 | 5 | 4 | 5 | 5 | 5 | 5 | — | 5 |
|  | 0.8 | 3 | 3 | 5 | 5 | 5 | 5 | — | 5 |
| 88 | 5 | 4 | 3 | 5 | 5 | 5 | 5 | — | 5 |
|  | 0.8 | 3 | 0 | 5 | 4 | 3 | 5 | — | — |
| 89 | 5 | 4 | 3 | 5 | 5 | 3 | — | 5 | 5 |
|  | 0.8 | 1 | 1 | 5 | 3 | 1 | — | 5 | 5 |
| 90 | 5 | 4 | 2 | 5 | 5 | — | 5 | — | 0 |
|  | 0.8 | 2 | 0 | 4 | 4 | 3 | 4 | — | 0 |
| 91 | 5 | 4 | 4 | 5 | 5 | 5 | 5 | — | 5 |
|  | 0.8 | 2 | 2 | 4 | 5 | 5 | 5 | — | 5 |
| 92 | 5 | 4 | 3 | 5 | 5 | 5 | — | 5 | 5 |
|  | 0.8 | 1 | 1 | 5 | 4 | 4 | — | 5 | 5 |
| 93 | 5 | 4 | 2 | 5 | 5 | 5 | — | 5 | 5 |
|  | 0.8 | 1 | 1 | 4 | 3 | 4 | — | 5 | 5 |
| 94 | 5 | 4 | 2 | 5 | 5 | 5 | — | 5 | 5 |
|  | 0.8 | 2 | 1 | 5 | 5 | 5 | — | 5 | 5 |
| 95 | 5 | 3 | 2 | 5 | 4 | 3 | — | 5 | 5 |
|  | 0.8 | 1 | 1 | 5 | 2 | 1 | — | 5 | 5 |
| 96 | 5 | 4 | 4 | 5 | 5 | 5 | — | 5 | 5 |
|  | 0.8 | 1 | 1 | 5 | 5 | 5 | — | 5 | 5 |
| 97 | 5 | 3 | 3 | 5 | 5 | 5 | — | 5 | 5 |
|  | 0.8 | 1 | 1 | 4 | 5 | 3 | — | 5 | 5 |
| 98 | 5 | 4 | 3 | 5 | 5 | 5 | — | 5 | 5 |

TABLE 7-continued

| Comp'd No. | Amount of active ingredient Kg/ha | Phytotoxicity | | Pre-emergence treatment | | | | | |
|---|---|---|---|---|---|---|---|---|---|
| | | wheat | soybean | barnyard-grass | velvet-leaf | cocklebur | jimsonweed | birdseye speedwell | cleavers |
| | 0.8 | 1 | 1 | 4 | 5 | 4 | — | 5 | 5 |
| 99 | 5 | 3 | 3 | 5 | 5 | 5 | — | 5 | 5 |
| | 0.8 | 1 | 1 | 4 | 3 | 4 | — | 5 | 5 |
| 100 | 5 | 4 | 3 | 5 | 5 | 3 | — | 5 | 5 |
| | 0.8 | 1 | 1 | 3 | 4 | 1 | — | 5 | 5 |
| 101 | 5 | 4 | 3 | 5 | 5 | 3 | — | 5 | 5 |
| | 0.8 | 1 | 1 | 4 | 5 | 1 | — | 5 | 5 |
| 102 | 5 | 4 | 4 | 5 | 5 | 5 | — | 5 | 5 |
| | 0.8 | 1 | 1 | 4 | 5 | 4 | — | 5 | 5 |
| 103 | 5 | 4 | 3 | 5 | 5 | 2 | 5 | — | 5 |
| | 0.8 | 3 | 1 | 5 | 4 | 0 | — | — | 5 |
| 104 | 5 | 4 | 4 | 5 | 5 | — | 5 | — | 5 |
| | 0.8 | 3 | 2 | 4 | 5 | 0 | — | — | 5 |
| 105 | 5 | 4 | 3 | 5 | 5 | — | 5 | — | 5 |
| | 0.8 | 3 | 1 | 5 | 5 | — | 5 | — | 5 |
| 106 | 5 | 4 | 3 | 5 | 5 | 2 | — | 5 | 5 |
| | 0.8 | 3 | 1 | 5 | 5 | — | — | 5 | 4 |
| 107 | 5 | 5 | 3 | 5 | 5 | 3 | — | 5 | 5 |
| | 0.8 | 3 | 1 | 5 | 4 | — | — | 5 | 5 |
| 108 | 5 | 4 | 3 | 5 | 5 | 3 | — | 5 | 5 |
| | 0.8 | 3 | 1 | 5 | 5 | — | — | 5 | 5 |
| 109 | 5 | 4 | 3 | 5 | 5 | 2 | 5 | — | 5 |
| | 0.8 | 3 | 1 | 5 | 5 | — | 5 | — | 5 |
| 110 | 5 | 5 | 3 | 5 | 5 | 2 | 5 | — | 5 |
| | 0.8 | 3 | 1 | 5 | 5 | — | 5 | — | 5 |
| 111 | 5 | 4 | 2 | 2 | 5 | 1 | 4 | — | 5 |
| | 0.8 | 1 | 0 | 1 | 4 | — | 2 | — | 3 |
| 112 | 5 | 4 | 4 | 5 | 5 | 5 | 5 | — | 5 |
| | 0.8 | 3 | 2 | 5 | 5 | 3 | 5 | — | — |
| 113 | 5 | 5 | 4 | 5 | 5 | 5 | 5 | — | 5 |
| | 0.8 | 3 | 2 | 5 | 5 | 4 | 5 | — | — |
| 114 | 5 | 3 | 3 | 5 | 5 | 5 | 5 | — | 5 |
| | 0.8 | 0 | 1 | 3 | 5 | 4 | 5 | — | 4 |
| 115 | 5 | 3 | 3 | 5 | 5 | 2 | 5 | — | 5 |
| | 0.8 | 0 | 0 | 4 | 5 | — | 2 | — | 3 |
| 116 | 5 | 4 | 4 | 5 | 5 | 2 | 5 | — | 5 |
| | 0.8 | 3 | 2 | 5 | 5 | — | 5 | — | 5 |
| 117 | 5 | 4 | 3 | 5 | 5 | 2 | 5 | — | 5 |
| | 0.8 | 2 | 0 | 5 | 5 | 0 | 5 | — | 5 |
| 118 | 5 | 4 | 2 | 5 | 5 | 3 | — | 5 | 5 |
| | 0.8 | 2 | 0 | 4 | 4 | 1 | — | 5 | 5 |
| 119 | 5 | 4 | 2 | 5 | 5 | 4 | 5 | — | 5 |
| | 0.8 | 2 | 0 | 5 | 4 | 2 | 5 | — | 5 |
| 120 | 5 | 3 | 3 | 5 | 5 | 2 | 5 | — | 5 |
| | 0.8 | 1 | 1 | 4 | 5 | — | 4 | — | 4 |
| 121 | 5 | 4 | 3 | 5 | 5 | 3 | 5 | — | 5 |
| | 0.8 | 2 | 1 | 4 | 5 | 1 | 5 | — | 5 |
| 122 | 5 | 4 | 3 | 5 | 5 | 2 | 5 | — | 5 |
| | 0.8 | 2 | 0 | 4 | 4 | — | 5 | — | 5 |
| 123 | 5 | 4 | 3 | 5 | 5 | 2 | 5 | — | 5 |
| | 0.8 | 2 | 1 | 4 | 5 | — | 5 | — | 5 |
| 125 | 5 | 4 | 3 | 5 | 5 | 2 | — | 5 | 5 |
| | 0.8 | 2 | 1 | 5 | 4 | 1 | — | 5 | 5 |
| 126 | 5 | 4 | 4 | 5 | 5 | — | 5 | — | 5 |
| | 0.8 | 2 | 2 | 5 | 5 | — | 5 | — | 5 |
| 127 | 5 | 4 | 4 | 5 | 5 | — | 5 | — | 5 |
| | 0.8 | 2 | 1 | 4 | 5 | — | 5 | — | 5 |
| 128 | 5 | 4 | 4 | 5 | 5 | 0 | 4 | — | 5 |
| | 0.8 | 2 | 1 | 4 | 4 | 0 | 3 | — | 4 |
| 129 | 5 | 4 | 4 | 5 | 5 | — | 5 | — | 5 |
| | 0.8 | 2 | 1 | 5 | 5 | — | 5 | — | 5 |
| 130 | 5 | 4 | 4 | 5 | 5 | 0 | 5 | — | 5 |
| | 0.8 | 1 | 0 | 5 | 4 | 0 | 5 | — | 5 |
| 131 | 5 | 4 | 4 | 5 | 4 | — | 5 | — | 5 |
| | 0.8 | 0 | 0 | 4 | 3 | — | 4 | — | 4 |
| 132 | 5 | 3 | 3 | 4 | 3 | — | 2 | — | 2 |
| | 0.8 | 0 | 0 | 3 | 1 | — | 0 | — | 0 |
| 133 | 5 | 4 | 4 | 5 | 5 | — | 5 | — | 5 |
| | 0.8 | 2 | 2 | 4 | 5 | — | 5 | — | 4 |
| 134 | 5 | 4 | 3 | 4 | 5 | — | 5 | — | 5 |
| | 0.8 | 2 | 1 | 3 | 5 | — | 4 | — | 5 |
| 135 | 5 | 4 | 4 | 5 | 5 | — | 5 | — | 5 |
| | 0.8 | 2 | 2 | 4 | 5 | — | 4 | — | 4 |
| 136 | 5 | 4 | 4 | 5 | 5 | — | 5 | — | 5 |
| | 0.8 | 2 | 2 | 4 | 5 | — | 5 | — | 4 |
| 137 | 5 | 4 | 4 | 5 | 5 | — | 5 | — | 5 |
| | 0.8 | 2 | 2 | 4 | 5 | — | 5 | — | 5 |

TABLE 7-continued

| Comp'd No. | Amount of active ingredient Kg/ha | Phytotoxicity | | Pre-emergence treatment | | | | | |
|---|---|---|---|---|---|---|---|---|---|
| | | wheat | soybean | barnyard-grass | velvet-leaf | cocklebur | jimsonweed | birdseye speedwell | cleavers |
| 138 | 5 | 4 | 4 | 5 | 5 | 5 | 5 | — | — |
| | 0.8 | 2 | 2 | 4 | 5 | 1 | 5 | — | — |
| 139 | 5 | 4 | 4 | 5 | 5 | 5 | 5 | — | 5 |
| | 0.8 | 2 | 2 | 5 | 5 | 3 | 5 | — | 5 |
| 140 | 5 | 4 | 4 | 5 | 5 | — | 5 | — | 5 |
| | 0.8 | 3 | 2 | 5 | 5 | — | 5 | — | 5 |
| 141 | 5 | 4 | 3 | 5 | 5 | — | 5 | — | 5 |
| | 0.8 | 2 | 1 | 5 | 5 | — | 5 | — | 5 |
| 142 | 5 | 4 | 4 | 5 | 5 | — | 5 | — | 5 |
| | 0.8 | 3 | 3 | 5 | 5 | — | 5 | — | 5 |
| 143 | 5 | 5 | 4 | 5 | 5 | — | 5 | — | 5 |
| | 0.8 | 3 | 2 | 5 | 5 | — | 5 | — | 5 |
| 144 | 5 | 3 | 3 | 5 | 5 | — | 5 | — | 5 |
| | 0.8 | 1 | 1 | 4 | 4 | — | 5 | — | 4 |
| 145 | 5 | 5 | 5 | 5 | 5 | 2 | 5 | — | 5 |
| | 0.8 | 3 | 3 | 4 | 5 | 0 | 5 | — | 5 |
| 146 | 5 | 3 | 4 | 5 | 5 | 4 | 5 | — | 5 |
| 147 | 5 | 2 | 2 | 5 | 5 | 3 | 5 | — | 5 |
| 148 | 5 | 2 | 0 | 5 | 5 | 2 | 5 | — | 5 |
| 149 | 5 | 3 | 5 | 5 | 5 | 5 | 5 | — | 5 |
| 150 | 5 | 4 | 3 | 5 | 5 | 4 | 5 | — | 5 |
| | 0.8 | 2 | 1 | 5 | 5 | 2 | 5 | — | 5 |
| 151 | 5 | 5 | 3 | 5 | 5 | 3 | 5 | — | 5 |
| | 0.8 | 3 | 1 | 5 | 5 | 1 | 5 | — | 5 |
| 152 | 5 | 4 | 4 | 5 | 5 | 5 | 5 | — | 5 |
| | 0.8 | 2 | 2 | 5 | 5 | 4 | 5 | — | 5 |
| 153 | 5 | 4 | 4 | 5 | 5 | 5 | 5 | — | 5 |
| | 0.8 | 3 | 2 | 5 | 5 | 3 | 5 | — | 4 |
| 154 | 5 | 3 | 2 | 5 | 4 | 3 | 5 | — | 5 |
| | 0.8 | 1 | 0 | 4 | 2 | 2 | 4 | — | 4 |
| 155 | 5 | 3 | 3 | 5 | 5 | 4 | 5 | — | 5 |
| | 0.8 | 1 | 0 | 4 | 4 | 3 | 4 | — | 5 |
| 156 | 5 | 3 | 3 | 5 | 4 | 2 | 5 | — | 5 |
| | 0.8 | 1 | 0 | 4 | 3 | 0 | 4 | — | 4 |
| 157 | 5 | 3 | 3 | 4 | 3 | 5 | — | — | 5 |
| | 0.8 | 1 | 0 | 3 | 2 | 4 | — | — | 5 |
| 158 | 5 | 3 | 3 | 4 | 5 | 0 | 5 | — | 3 |
| | 0.8 | 1 | 0 | 3 | 4 | 0 | 4 | — | 0 |
| 159 | 5 | 3 | 3 | 4 | 5 | 0 | 5 | — | 2 |
| | 0.8 | 1 | 0 | 3 | 4 | 0 | 5 | — | 0 |
| 160 | 5 | 3 | 3 | 4 | 5 | 0 | 5 | — | 2 |
| | 0.8 | 0 | 0 | 3 | 3 | 0 | 3 | — | 0 |
| 161 | 5 | 3 | 3 | 5 | 5 | 2 | 4 | — | 4 |
| | 0.8 | 1 | 1 | 4 | 5 | 0 | 3 | — | — |
| 162 | 5 | 5 | 3 | 5 | 5 | 4 | 5 | — | 5 |
| | 0.8 | 3 | 1 | 5 | 4 | 3 | 5 | — | 4 |
| 163 | 5 | 5 | 3 | 5 | 5 | 2 | 5 | — | 5 |
| | 0.8 | 3 | 1 | 5 | 4 | 0 | 3 | — | 4 |
| 164 | 5 | 3 | 3 | 5 | 5 | — | 5 | — | 5 |
| | 0.8 | 1 | 1 | 5 | 4 | — | 5 | — | 5 |
| 165 | 5 | 4 | 3 | 5 | 5 | — | 5 | — | 5 |
| | 0.8 | 2 | 1 | 4 | 5 | — | 4 | — | 4 |
| 166 | 5 | 4 | 3 | 5 | 5 | — | 5 | — | 5 |
| | 0.8 | 2 | 0 | 4 | 4 | — | 4 | — | 4 |
| 167 | 5 | 3 | 3 | 5 | 5 | 3 | 5 | — | 5 |
| | 0.8 | 1 | 1 | 4 | 4 | 1 | 5 | — | 4 |
| 168 | 5 | 3 | 3 | 5 | 5 | 2 | 5 | — | 5 |
| | 0.8 | 0 | 0 | 4 | 4 | 1 | 4 | — | 4 |
| 169 | 5 | 3 | 3 | 5 | 5 | 5 | 2 | — | 5 |
| | 0.8 | 1 | 0 | 4 | 4 | 3 | 0 | — | 4 |
| 170 | 5 | 3 | 3 | 4 | 4 | 5 | 2 | — | 4 |
| | 0.8 | 0 | 0 | 2 | 2 | 3 | 0 | — | 4 |
| 171 | 5 | 3 | 5 | 5 | 4 | 0 | — | — | 5 |
| | 0.8 | 1 | 3 | 4 | 2 | 0 | — | — | 5 |
| 172 | 5 | 4 | 3 | 5 | 5 | — | 5 | — | 5 |
| | 0.8 | 2 | 1 | 4 | 4 | 0 | — | — | 4 |
| 173 | 5 | 3 | 3 | 3 | 2 | 0 | 2 | — | 4 |
| | 0.8 | 0 | 0 | 1 | 0 | 0 | 0 | — | 3 |
| 174 | 5 | 3 | 3 | 5 | 4 | 0 | 2 | — | 5 |
| | 0.8 | 1 | 0 | 4 | 3 | 0 | — | — | 4 |
| 175 | 5 | 4 | 4 | 5 | 5 | — | 5 | — | 5 |
| | 0.8 | 2 | 2 | 4 | 4 | 0 | — | — | 5 |
| 176 | 5 | 2 | 2 | 3 | 2 | 0 | 2 | — | 1 |
| 177 | 5 | 3 | 2 | 5 | 4 | 0 | 3 | — | 1 |
| | 0.8 | 0 | 0 | 4 | 3 | 0 | 2 | — | 0 |
| 178 | 5 | 3 | 3 | 5 | 4 | 0 | 2 | — | 1 |
| | 0.8 | 1 | 1 | 4 | 3 | 0 | 0 | — | 0 |

TABLE 7-continued

| Comp'd No. | Amount of active ingredient Kg/ha | Phytotoxicity | | Pre-emergence treatment | | | | | |
|---|---|---|---|---|---|---|---|---|---|
| | | wheat | soybean | barnyard-grass | velvet-leaf | cocklebur | jimsonweed | birdseye speedwell | cleavers |
| 179 | 5 | 3 | 3 | 5 | 4 | 0 | 5 | — | 5 |
| | 0.8 | 1 | 0 | 4 | 3 | 0 | 5 | — | 3 |
| 180 | 5 | 3 | 2 | 2 | 4 | — | 3 | — | 4 |
| | 0.8 | 1 | 0 | 1 | 2 | 0 | 1 | — | 2 |
| 181 | 5 | 3 | 3 | 4 | 5 | — | 5 | — | 2 |
| | 0.8 | 0 | 0 | 3 | 4 | 0 | 3 | — | 0 |
| 182 | 5 | 3 | 3 | 5 | 4 | — | 5 | — | 5 |
| | 0.8 | 0 | 0 | 4 | 3 | 0 | 5 | — | 5 |
| 183 | 5 | 3 | 2 | 4 | 3 | — | 5 | — | 5 |
| | 0.8 | 1 | 0 | 4 | 1 | — | 3 | — | 5 |
| 184 | 5 | 3 | 2 | 4 | 2 | — | 2 | — | 2 |
| 185 | 5 | 3 | 2 | 5 | 2 | 0 | 2 | — | 1 |
| 186 | 5 | 3 | 2 | 5 | 5 | 0 | 2 | — | 1 |
| 187 | 5 | 2 | 2 | 2 | 3 | 0 | 2 | — | 1 |
| 188 | 5 | 2 | 2 | 3 | 2 | — | 2 | 5 | 1 |
| 189 | 5 | 3 | 3 | 5 | 4 | — | 5 | — | 5 |
| | 0.8 | 1 | 0 | 4 | 2 | 0 | 4 | — | 4 |
| 190 | 5 | 3 | 3 | 4 | 4 | — | — | 5 | 5 |
| | 0.8 | 1 | 1 | 3 | 2 | — | 0 | 5 | 5 |
| 191 | 5 | 3 | 3 | 4 | 5 | 2 | — | 5 | 5 |
| | 0.8 | 1 | 1 | 3 | 3 | 1 | — | 5 | 5 |
| 192 | 5 | 3 | 3 | 5 | 2 | — | — | 5 | 5 |
| | 0.8 | 0 | 0 | 2 | 1 | 0 | — | 5 | 5 |
| 193 | 5 | 2 | 1 | 2 | 3 | — | 2 | — | 1 |
| 194 | 5 | 4 | 3 | 5 | 5 | 5 | 5 | — | 5 |
| | 0.8 | 2 | 1 | 4 | 5 | 2 | 5 | — | 5 |
| 195 | 5 | 3 | 3 | 5 | 5 | — | 4 | — | 1 |
| | 0.8 | 1 | 1 | 4 | 5 | 0 | 3 | — | 0 |
| 196 | 5 | 3 | 3 | 5 | 5 | — | 4 | — | 1 |
| | 0.8 | 0 | 1 | 4 | 5 | 0 | 3 | — | 0 |
| 197 | 5 | 3 | 3 | 5 | 4 | — | 5 | — | 5 |
| | 0.8 | 1 | 0 | 4 | 3 | — | 5 | — | 3 |
| 198 | 5 | 3 | 3 | 4 | 5 | — | — | 5 | 5 |
| | 0.8 | 1 | 1 | 3 | 3 | — | — | 5 | 5 |
| 199 | 5 | 3 | 3 | 4 | 4 | 2 | — | 5 | 2 |
| | 0.8 | 1 | 1 | 3 | 2 | 1 | — | 5 | 1 |
| 200 | 5 | 3 | 3 | 3 | 3 | — | — | 5 | 5 |
| | 0.8 | 1 | 0 | 2 | 1 | 0 | — | 5 | 5 |
| 201 | 5 | 3 | 3 | 4 | 4 | — | — | 5 | 5 |
| | 0.8 | 0 | 1 | 3 | 2 | 0 | — | 5 | 5 |
| 202 | 5 | 2 | 2 | 3 | 2 | — | — | 5 | 1 |
| | 0.8 | 0 | 0 | 2 | 0 | 0 | — | 5 | 0 |
| 203 | 5 | 2 | 2 | 3 | 2 | — | — | 5 | 1 |
| | 0.8 | 0 | 0 | 2 | 0 | 0 | — | 5 | 0 |
| 204 | 5 | 3 | 3 | 3 | 4 | 2 | — | 5 | 5 |
| | 0.8 | 1 | 1 | 2 | 2 | 1 | — | 5 | 5 |
| 206 | 5 | 3 | 3 | 4 | 2 | — | 4 | — | 5 |
| | 0.8 | 1 | 1 | 3 | 0 | 0 | 2 | — | 4 |
| 207 | 5 | 2 | 2 | 4 | 4 | — | 2 | — | 1 |
| | 0.8 | 0 | 0 | 3 | 2 | 0 | 0 | — | 0 |
| 208 | 5 | 2 | 2 | 4 | 5 | — | 5 | — | 1 |
| | 0.8 | 0 | 0 | 3 | 3 | 0 | 4 | — | 0 |
| 209 | 5 | 2 | 2 | 4 | 5 | — | 4 | — | 1 |
| | 0.8 | 0 | 0 | 3 | 3 | 0 | 2 | — | 0 |
| 210 | 5 | 1 | 1 | 4 | 1 | — | 4 | — | 4 |
| 212 | 5 | 2 | 1 | 4 | 3 | 0 | 0 | — | 5 |
| 216 | 5 | 3 | 2 | 4 | 3 | 5 | 2 | — | 5 |
| | 0.8 | 1 | 0 | 2 | 2 | 4 | 0 | — | 5 |
| 220 | 5 | 3 | 4 | 5 | 5 | 5 | 5 | — | 5 |
| | 0.8 | 0 | 2 | 5 | 4 | 1 | 5 | — | 5 |
| 221 | 5 | 3 | 3 | 5 | 4 | 0 | 5 | — | 5 |
| | 0.8 | 1 | 1 | 5 | 3 | — | 4 | — | 5 |
| 222 | 5 | 3 | 3 | 5 | 3 | 3 | 5 | — | 5 |
| | 0.8 | 3 | 0 | 5 | 2 | 1 | 5 | — | 5 |
| 224 | 5 | 3 | 2 | 4 | 4 | 1 | — | 5 | 1 |
| | 0.8 | 1 | 0 | 3 | 1 | 0 | — | .5 | 1 |
| 225 | 5 | 5 | 3 | 5 | 5 | 2 | — | 5 | 5 |
| | 0.8 | 3 | 1 | 4 | 5 | 0 | — | 5 | 5 |
| 227 | 5 | 3 | 3 | 3 | 4 | 0 | — | 5 | 2 |
| 229 | 5 | 3 | 2 | 4 | 5 | 1 | — | 5 | 5 |
| | 0.8 | 1 | 0 | 2 | 3 | 0 | — | 5 | 4 |
| 230 | 5 | 4 | 4 | 5 | 5 | 1 | — | 5 | 5 |
| | 0.8 | 2 | 2 | 4 | 5 | 0 | — | 5 | 5 |
| 231 | 5 | 3 | 3 | 4 | 5 | 1 | — | 5 | 5 |
| | 0.8 | 1 | 1 | 3 | 4 | 0 | — | 5 | 4 |
| 232 | 5 | 3 | 3 | 5 | 5 | 1 | — | 5 | 5 |
| | 0.8 | 1 | 1 | 4 | 5 | 0 | — | 5 | 5 |

TABLE 7-continued

| Comp'd No. | Amount of active ingredient Kg/ha | Phytotoxicity | | Pre-emergence treatment | | | | | |
|---|---|---|---|---|---|---|---|---|---|
| | | wheat | soybean | barnyard-grass | velvet-leaf | cocklebur | jimsonweed | birdseye speedwell | cleavers |
| 233 | 5 | 3 | 2 | 4 | 5 | 2 | — | 5 | 5 |
| | 0.8 | 1 | 0 | 3 | 5 | 1 | — | 5 | 5 |
| 234 | 5 | 3 | 3 | 5 | 5 | 1 | — | 5 | 5 |
| | 0.8 | 1 | 1 | 4 | 4 | 0 | — | 5 | 5 |
| 235 | 5 | 3 | 2 | 3 | 5 | 0 | — | 5 | 2 |
| | 0.8 | 1 | 0 | 2 | 4 | 0 | — | 5 | 0 |
| 236 | 0.8 | 2 | 1 | 4 | 5 | 1 | — | 5 | 4 |
| | 0.2 | 0 | 0 | 2 | 4 | 0 | — | 5 | 1 |
| 237 | 5 | 3 | 2 | 3 | 5 | 1 | — | 5 | 5 |
| | 0.8 | 1 | 0 | 2 | 3 | 0 | — | 5 | 4 |
| 238 | 5 | 4 | 4 | 5 | 5 | 2 | — | 5 | 5 |
| | 0.8 | 2 | 2 | 4 | 5 | — | — | 5 | 5 |
| 239 | 5 | 3 | 3 | 5 | 5 | 2 | — | 5 | 5 |
| | 0.8 | 1 | 1 | 4 | 5 | — | — | 5 | 5 |
| 240 | 5 | 3 | 3 | 5 | 5 | 2 | — | 5 | 5 |
| | 0.8 | 1 | 1 | 4 | 5 | — | — | 5 | 5 |
| 241 | 5 | 3 | 2 | 5 | 5 | 1 | — | 5 | 5 |
| | 0.8 | 1 | 0 | 3 | 4 | 0 | — | 5 | 3 |
| 242 | 5 | 3 | 2 | 5 | 5 | 1 | — | 5 | 4 |
| | 0.8 | 1 | 0 | 4 | 5 | 0 | — | 5 | 3 |
| 243 | 0.8 | 2 | 1 | 4 | 5 | 1 | — | 5 | 4 |
| | 0.2 | 0 | 0 | 2 | 4 | 0 | — | 5 | 1 |
| 244 | 5 | 3 | 3 | 5 | 5 | 5 | — | 5 | 5 |
| | 0.8 | 1 | 1 | 4 | 4 | 3 | — | 5 | 5 |
| 245 | 5 | 3 | 3 | 5 | 5 | 1 | — | 5 | 5 |
| | 0.8 | 1 | 1 | 3 | 4 | 0 | — | 5 | 5 |
| 247 | 5 | 3 | 3 | 3 | 4 | 0 | — | 5 | 2 |
| | 0.8 | 1 | 1 | 2 | 1 | 0 | — | 5 | 1 |
| 248 | 5 | 3 | 2 | 5 | 5 | 2 | — | 5 | 5 |
| | 0.8 | 1 | 0 | 3 | 3 | 0 | — | 5 | 4 |
| 249 | 5 | 3 | 3 | 5 | 5 | 2 | — | 5 | 5 |
| | 0.8 | 1 | 1 | 3 | 4 | 0 | — | 5 | 5 |
| 250 | 5 | 4 | 3 | 5 | 5 | 1 | — | 5 | 5 |
| | 0.8 | 2 | 1 | 5 | 5 | 0 | — | 5 | 5 |
| 251 | 5 | 4 | 3 | 5 | 5 | 4 | — | 5 | 5 |
| | 0.8 | 2 | 1 | 5 | 5 | 2 | — | 5 | 5 |
| 252 | 5 | 3 | 2 | 4 | 4 | 1 | — | 5 | 4 |
| | 0.8 | 1 | 0 | 3 | 2 | 0 | — | 5 | 2 |
| 253 | 5 | 4 | 3 | 5 | 5 | 3 | — | 5 | 5 |
| | 0.8 | 2 | 1 | 4 | 5 | 2 | — | 5 | 4 |
| 254 | 5 | 3 | 3 | 5 | 5 | 2 | — | 5 | 5 |
| | 0.8 | 1 | 1 | 4 | 4 | 0 | — | 5 | 5 |
| 255 | 0.8 | 5 | 5 | 5 | 5 | 4 | — | 5 | 5 |
| | 0.2 | 3 | 3 | 4 | 5 | 2 | — | 5 | 5 |
| 256 | 0.2 | 5 | 3 | 5 | 5 | 2 | — | 5 | 5 |
| | 0.1 | 3 | 2 | 4 | 5 | 1 | — | 5 | 5 |
| 257 | 0.8 | 3 | 2 | 5 | 5 | 2 | — | 5 | 5 |
| | 0.2 | 1 | 0 | 5 | 5 | 0 | — | 5 | 4 |
| 258 | 0.2 | 5 | 4 | 5 | 5 | 4 | — | 5 | 5 |
| | 0.1 | 3 | 3 | 4 | 5 | 2 | — | 5 | 5 |
| 259 | 0.8 | 3 | 3 | 4 | 3 | 1 | — | 5 | 4 |
| | 0.2 | 0 | 0 | 2 | 1 | 0 | — | 4 | 2 |
| 260 | 0.8 | 3 | 2 | 4 | 5 | 1 | — | 5 | 3 |
| | 0.2 | 1 | 0 | 3 | 3 | 0 | — | 5 | 5 |
| 261 | 0.8 | 4 | 3 | 5 | 5 | 4 | — | 5 | 5 |
| | 0.2 | 2 | 1 | 4 | 5 | 3 | — | 5 | 5 |
| 262 | 0.8 | 2 | 1 | 4 | 5 | 1 | — | 5 | 4 |
| | 0.2 | 0 | 0 | 2 | 3 | 0 | — | 5 | 2 |
| 263 | 0.8 | 2 | 1 | 3 | 4 | 1 | — | 5 | 3 |
| | 0.2 | 0 | 0 | 0 | 2 | 0 | — | 5 | 2 |
| 264 | 0.8 | 2 | 1 | 3 | 4 | 1 | — | 5 | 3 |
| | 0.2 | 0 | 0 | 0 | 1 | 1 | — | 5 | 0 |
| 265 | 0.8 | 3 | 1 | 4 | 5 | 1 | — | 5 | 3 |
| | 0.2 | 1 | 0 | 2 | 4 | 0 | — | 5 | 0 |
| 266 | 0.8 | 2 | 1 | 4 | 3 | 1 | — | 5 | 5 |
| | 0.2 | 0 | 0 | 2 | 0 | 0 | — | 5 | 5 |
| 267 | 0.8 | 2 | 2 | 3 | 4 | 1 | — | 5 | 5 |
| | 0.2 | 0 | 1 | 0 | 2 | 0 | — | 5 | 5 |
| 269 | 0.8 | 3 | 1 | 5 | 4 | 0 | — | 5 | 4 |
| | 0.2 | 1 | 0 | 2 | 2 | 0 | — | 5 | 3 |
| 270 | 0.8 | 3 | 1 | 5 | 5 | 1 | — | 5 | 4 |
| | 0.2 | 1 | 0 | 5 | 3 | 0 | — | 5 | 2 |
| 271 | 0.8 | 3 | 1 | 5 | 5 | 3 | — | 5 | 5 |
| | 0.2 | 1 | 0 | 4 | 5 | 3 | — | 5 | 3 |
| 272 | 0.8 | 3 | 2 | 5 | 5 | 2 | — | 5 | 5 |
| | 0.2 | 2 | 1 | 5 | 5 | 0 | — | 5 | 5 |
| 273 | 0.8 | 3 | 1 | 5 | 4 | 1 | — | 5 | 5 |

TABLE 7-continued

| Comp'd No. | Amount of active ingredient Kg/ha | Phytotoxicity | | Pre-emergence treatment | | | | | |
|---|---|---|---|---|---|---|---|---|---|
| | | wheat | soybean | barnyard-grass | velvet-leaf | cocklebur | jimsonweed | birdseye speedwell | cleavers |
| | 0.2 | 1 | 1 | 4 | 2 | 0 | — | 5 | 1 |
| 274 | 0.8 | 3 | 1 | 5 | 5 | 1 | — | 5 | 5 |
| | 0.2 | 1 | 0 | 3 | 5 | 1 | — | 5 | 4 |
| 275 | 0.8 | 3 | 1 | 5 | 5 | 1 | — | 5 | 5 |
| | 0.2 | 1 | 0 | 3 | 4 | 0 | — | 5 | 5 |
| 276 | 5 | 4 | 3 | 5 | 5 | 1 | — | 5 | 4 |
| | 0.8 | 2 | 1 | 3 | 4 | 0 | — | 5 | 3 |
| 277 | 5 | 3 | 3 | 4 | 5 | 1 | — | 5 | 4 |
| | 0.8 | 1 | 1 | 3 | 5 | 0 | — | 5 | 2 |
| 278 | 5 | 3 | 3 | 4 | 5 | 1 | — | 5 | 4 |
| | 0.8 | 1 | 1 | 3 | 4 | 0 | — | 5 | 3 |
| 279 | 5 | 3 | 3 | 4 | 5 | 1 | — | 5 | 4 |
| | 0.8 | 0 | 0 | 2 | 3 | 0 | — | 5 | 3 |
| 280 | 5 | 4 | 2 | 5 | 5 | 1 | — | 5 | 5 |
| | 0.8 | 2 | 0 | 4 | 3 | 0 | — | 5 | 5 |
| 281 | 5 | 3 | 3 | 5 | 5 | 1 | — | 5 | 5 |
| | 0.8 | 1 | 1 | 4 | 5 | 0 | — | 5 | 5 |
| 282 | 5 | 3 | 3 | 5 | 5 | 2 | — | 5 | 5 |
| | 0.8 | 1 | 1 | 4 | 5 | 0 | — | 5 | 5 |
| 283 | 5 | 3 | 3 | 5 | 5 | 2 | — | 5 | 5 |
| | 0.8 | 1 | 1 | 4 | 5 | 0 | — | 5 | 5 |
| 284 | 5 | 3 | 3 | 5 | 5 | 1 | — | 5 | 5 |
| | 0.8 | 1 | 1 | 4 | 3 | 0 | — | 5 | 5 |
| 285 | 5 | 3 | 3 | 5 | 5 | 3 | — | 5 | 5 |
| | 0.8 | 1 | 1 | 4 | 5 | 2 | — | 5 | 5 |
| 286 | 5 | 3 | 3 | 5 | 5 | 2 | — | 5 | 5 |
| | 0.8 | 1 | 1 | 3 | 4 | 0 | — | 5 | 5 |
| 287 | 5 | 4 | 2 | 5 | 5 | 2 | — | 5 | 5 |
| | 0.8 | 2 | 0 | 4 | 5 | — | — | 5 | 5 |
| 288 | 5 | 4 | 3 | 5 | 5 | 2 | — | 5 | 5 |
| | 0.8 | 2 | 1 | 4 | 5 | — | — | 5 | 5 |
| 289 | 5 | 4 | 3 | 5 | 5 | 2 | — | 5 | 5 |
| | 0.8 | 2 | 1 | 4 | 5 | — | — | 5 | 4 |
| 290 | 5 | 3 | 3 | 5 | 5 | 2 | — | 5 | 5 |
| | 0.8 | 1 | 1 | 5 | 5 | 1 | — | 5 | 5 |
| 291 | 5 | 3 | 3 | 5 | 3 | 2 | — | 5 | 5 |
| | 0.8 | 1 | 1 | 4 | 1 | 1 | — | 5 | 5 |
| 292 | 5 | 3 | 2 | 5 | 5 | 4 | — | 5 | 5 |
| | 0.8 | 1 | 0 | 3 | 4 | 2 | — | 5 | 5 |
| 293 | 5 | 3 | 1 | 3 | 5 | 2 | — | 5 | 5 |
| | 0.8 | 1 | 0 | 2 | 4 | 0 | — | 5 | 5 |
| 294 | 5 | 3 | 1 | 4 | 3 | 1 | — | 5 | 5 |
| | 0.8 | 1 | 0 | 3 | 1 | 0 | — | 5 | 5 |
| 295 | 5 | 3 | 2 | 5 | 5 | 1 | — | 5 | 5 |
| | 0.8 | 1 | 0 | 4 | 4 | 0 | — | 5 | 5 |
| 296 | 5 | 4 | 3 | 5 | 5 | 1 | — | 5 | 5 |
| | 0.8 | 2 | 1 | 4 | 4 | 0 | — | 5 | 5 |
| 297 | 5 | 3 | 3 | 5 | 5 | 1 | — | 5 | 5 |
| | 0.8 | 1 | 1 | 4 | 4 | — | — | 5 | 5 |
| 298 | 5 | 3 | 3 | 4 | 5 | 1 | — | 5 | 5 |
| | 0.8 | 1 | 1 | 3 | 4 | — | — | 5 | 5 |
| 299 | 5 | 4 | 3 | 5 | 5 | 1 | — | 5 | 5 |
| | 0.8 | 2 | 1 | 3 | 4 | 0 | — | 5 | 4 |
| 300 | 5 | 3 | 2 | 4 | 5 | 1 | — | 5 | 5 |
| | 0.8 | 1 | 0 | 2 | 3 | 0 | — | 5 | 4 |
| 302 | 5 | 4 | 2 | 5 | 5 | 2 | — | 5 | 5 |
| | 0.8 | 2 | 0 | 4 | 5 | 0 | — | 5 | 5 |
| 301 | 5 | 3 | 2 | 4 | 5 | 1 | — | 5 | 5 |
| | 0.8 | 1 | 0 | 3 | 3 | 0 | — | 5 | 5 |
| 303 | 5 | 4 | 2 | 4 | 5 | 1 | — | 5 | 5 |
| | 0.8 | 2 | 0 | 3 | 3 | 0 | — | 5 | 5 |
| 304 | 5 | 3 | 3 | 5 | 5 | 2 | — | 5 | 5 |
| | 0.8 | 1 | 1 | 4 | 4 | 1 | — | 5 | 5 |
| 305 | 5 | 3 | 3 | 5 | 5 | 1 | — | 5 | 5 |
| | 0.8 | 1 | 1 | 4 | 5 | 0 | — | 5 | 3 |
| 306 | 5 | 4 | 3 | 4 | 5 | 2 | — | 5 | 5 |
| | 0.8 | 2 | 1 | 3 | 3 | 1 | — | 5 | 5 |
| 307 | 5 | 3 | 2 | 5 | 5 | 2 | — | 5 | 5 |
| | 0.8 | 1 | 0 | 4 | 4 | 0 | — | 5 | 5 |
| 308 | 5 | 4 | 3 | 5 | 5 | 2 | — | 5 | 5 |
| | 0.8 | 2 | 1 | 4 | 5 | — | — | 5 | 4 |
| 309 | 5 | 4 | 4 | 5 | 5 | 2 | — | 5 | 5 |
| | 0.8 | 2 | 2 | 4 | 5 | — | — | 5 | 5 |
| 310 | 5 | 4 | 5 | 5 | 5 | 2 | — | 5 | 5 |
| | 0.8 | 2 | 3 | 3 | 5 | 0 | — | 5 | 5 |
| 312 | 5 | 3 | 2 | 3 | 4 | 1 | — | 5 | 5 |
| | 0.8 | 1 | 0 | 2 | 2 | 0 | — | 5 | 5 |

TABLE 7-continued

| Comp'd No. | Amount of active ingredient Kg/ha | Phytotoxicity wheat | Phytotoxicity soybean | Pre-emergence treatment barnyard-grass | velvet-leaf | cocklebur | jimsonweed | birdseye speedwell | cleavers |
|---|---|---|---|---|---|---|---|---|---|
| 313 | 5 | 3 | 3 | 5 | 5 | 2 | — | 5 | 5 |
|  | 0.8 | 1 | 1 | 4 | 5 | 0 | — | 5 | 5 |
| 314 | 5 | 3 | 2 | 4 | 5 | 2 | — | 5 | 5 |
|  | 0.8 | 1 | 0 | 2 | 5 | 0 | — | 5 | 5 |
| 315 | 5 | 3 | 3 | 5 | 5 | 1 | — | 5 | 5 |
|  | 0.8 | 1 | 1 | 3 | 4 | 0 | — | 5 | 5 |
| 316 | 5 | 4 | 3 | 5 | 5 | 2 | — | 5 | 5 |
|  | 0.8 | 2 | 1 | 3 | 4 | 1 | — | 5 | 5 |
| 317 | 5 | 4 | 3 | 5 | 5 | 2 | — | 5 | 5 |
|  | 0.8 | 2 | 1 | 3 | 4 | 1 | — | 5 | 5 |
| 318 | 5 | 3 | 2 | 5 | 3 | 2 | — | 5 | 5 |
|  | 0.8 | 1 | 0 | 4 | 1 | 1 | — | 5 | 5 |
| 319 | 5 | 3 | 3 | 5 | 5 | 5 | — | 5 | 5 |
|  | 0.8 | 1 | 1 | 5 | 5 | 3 | — | 5 | 5 |
| 320 | 5 | 3 | 3 | 5 | 5 | 2 | — | 5 | 4 |
|  | 0.8 | 0 | 0 | 4 | 5 | 1 | — | 5 | 2 |
| 321 | 5 | 3 | 2 | 4 | 5 | 1 | — | 5 | 5 |
|  | 0.8 | 1 | 0 | 2 | 3 | 0 | — | 5 | 4 |
| 322 | 5 | 2 | 1 | 3 | 4 | 1 | — | 5 | 4 |
|  | 0.8 | 0 | 0 | 0 | 1 | 0 | — | 3 | 2 |
| 323 | 5 | 4 | 4 | 5 | 5 | 5 | — |  | 5 |
|  | 0.8 | 2 | 2 | 5 | 4 | 3 | — | 5 | 4 |
| 324 | 5 | 5 | 4 | 5 | 5 | 4 | — | 5 | 5 |
|  | 0.8 | 3 | 2 | 5 | 4 | 3 | — | 5 | 3 |
| 325 | 5 | 3 | 4 | 5 | 5 | — | — | 5 | 5 |
|  | 0.8 | 1 | 2 | 4 | 5 | — | — | 5 | 4 |
| 326 | 5 | 4 | 3 | 5 | 5 | 5 | — | 5 | 5 |
|  | 0.8 | 2 | 1 | 4 | 5 | 3 | — | 5 | 5 |
| 327 | 5 | 4 | 3 | 5 | 5 | 5 | — | 5 | 5 |
|  | 0.8 | 2 | 1 | 4 | 5 | 2 | — | 5 | 5 |
| 328 | 5 | 3 | 4 | 5 | 5 | 4 | — | 5 | 5 |
|  | 0.8 | 1 | 2 | 4 | 5 | 2 | — | 5 | 4 |
| 329 | 5 | 2 | 1 | 3 | 3 | 1 | — | 5 | 4 |
|  | 0.8 | 0 | 0 | 1 | 0 | 0 | — | 5 | 1 |
| 330 | 5 | 3 | 1 | 4 | 5 | 1 | — | 5 | 5 |
| 331 | 5 | 5 | 5 | 5 | 5 | 5 | — | 5 | 5 |
|  | 0.8 | 3 | 4 | 5 | 5 | 5 | — | 5 | 5 |
| 332 | 0.8 | 5 | 5 | 5 | 5 | 5 | — | 5 | 5 |
|  | 0.2 | 3 | 3 | 3 | 4 | 3 | — | 5 | 4 |
| 333 | 5 | 3 | 2 | 4 | 5 | 1 | — | 5 | 2 |
|  | 0.8 | 1 | 0 | 3 | 3 | 1 | — | 5 | — |
| 334 | 5 | 2 | 2 | 3 | 4 | 1 | — | 5 | 5 |
|  | 0.8 | 0 | 0 | 2 | 2 | 0 | — | 5 | 5 |
| 335 | 5 | 2 | 1 | 4 | 5 | 1 | — | 5 | 5 |
|  | 0.8 | 0 | 0 | 0 | 0 | 0 | — | 4 | — |
| 336 | 5 | 2 | 2 | 5 | 5 | 2 | — | 5 | 5 |
|  | 0.8 | 0 | 0 | 4 | 5 | 1 | — | 5 | 4 |
| 337 | 5 | 2 | 2 | 4 | 3 | 1 | — | 5 | 5 |
|  | 0.8 | 0 | 0 | 3 | 1 | 0 | — | 5 | 3 |
| 338 | 5 | 3 | 2 | 4 | 5 | 1 | — | 5 | 5 |
|  | 0.8 | 1 | 0 | 3 | 3 | 0 | — | 5 | 5 |
| 339 | 5 | 2 | 1 | 4 | 4 | 0 | — | 5 | 4 |
| 340 | 5 | 2 | 2 | 3 | 4 | 1 | — | 5 | 5 |
|  | 0.8 | 0 | 0 | 2 | 2 | 0 | — | 5 | 5 |
| 341 | 0.8 | 3 | 1 | 3 | 4 | 1 | — | 5 | 4 |
|  | 0.2 | 1 | 0 | 0 | 1 | 0 | — | 3 | 3 |
| 342 | 0.8 | 3 | 1 | 5 | 5 | 1 | — | 5 | 4 |
|  | 0.2 | 1 | 0 | 4 | 5 | 0 | — | 5 | 2 |
| 343 | 0.8 | 3 | 1 | 5 | 5 | 1 | — | 5 | 4 |
|  | 0.2 | 1 | 0 | 4 | 5 | 0 | — | 5 | 2 |
| 344 | 0.8 | 3 | 1 | 5 | 5 | 1 | — | 5 | 4 |
|  | 0.2 | 1 | 0 | 3 | 3 | 0 | — | 5 | 2 |
| 345 | 0.8 | 3 | 2 | 5 | 5 | 1 | — | 5 | 4 |
|  | 0.2 | 1 | 1 | 3 | 4 | 0 | — | 5 | 2 |
| 346 | 0.8 | 3 | 1 | 5 | 5 | 1 | — | 5 | 4 |
|  | 0.2 | 1 | 0 | 3 | 4 | 0 | — | 5 | 2 |
| 347 | 0.8 | 3 | 1 | 5 | 5 | 1 | — | 5 | 4 |
|  | 0.2 | 1 | 0 | 3 | 4 | 0 | — | 5 | 1 |
| 348 | 0.8 | 3 | 1 | 5 | 5 | 1 | — | 5 | 4 |
|  | 0.2 | 1 | 0 | 3 | 5 | 0 | — | 5 | 1 |
| 349 | 0.8 | 3 | 1 | 4 | 5 | 1 | — | 5 | 4 |
|  | 0.2 | 1 | 0 | 2 | 4 | 0 | — | 5 | 1 |
| 350 | 0.8 | 3 | 1 | 4 | 5 | 1 | — | 5 | 4 |
|  | 0.2 | 1 | 0 | 2 | 3 | 0 | — | 5 | 4 |
| 351 | 0.8 | 2 | 1 | 3 | 4 | 1 | — | 5 | 4 |
|  | 0.2 | 0 | 0 | 0 | 3 | — | — | 5 | 1 |
| 352 | 0.8 | 3 | 1 | 4 | 5 | 1 | — | 5 | 5 |

TABLE 7-continued

| Comp'd No. | Amount of active ingredient Kg/ha | Phytotoxicity | | Pre-emergence treatment | | | | | |
|---|---|---|---|---|---|---|---|---|---|
| | | wheat | soybean | barnyard-grass | velvet-leaf | cocklebur | jimsonweed | birdseye speedwell | cleavers |
| | 0.2 | 1 | 0 | 2 | 4 | 0 | — | 5 | 4 |
| 353 | 0.8 | 2 | 1 | 4 | 5 | 1 | — | 5 | 3 |
| | 0.2 | 0 | 0 | 2 | 4 | 0 | — | 5 | 0 |
| 354 | 0.8 | 3 | 1 | 4 | 4 | 0 | — | 5 | 4 |
| | 0.2 | 1 | 0 | 2 | 2 | 0 | — | 5 | 4 |
| 355 | 0.8 | 2 | 1 | 4 | 4 | 0 | — | 5 | 4 |
| | 0.2 | 0 | 0 | 2 | 2 | 0 | — | 5 | 0 |
| 356 | 0.8 | 2 | 1 | 4 | 4 | 0 | — | 5 | 4 |
| | 0.2 | 1 | 0 | 1 | 1 | 0 | — | 5 | 0 |
| 357 | 0.8 | 2 | 1 | 4 | 4 | 1 | — | 5 | 4 |
| | 0.2 | 0 | 0 | 3 | 1 | 0 | — | 5 | 0 |
| 358 | 0.8 | 2 | 1 | 4 | 5 | 1 | — | 5 | 3 |
| | 0.2 | 0 | 0 | 3 | 4 | 0 | — | 5 | 0 |
| 359 | 0.8 | 3 | 1 | 5 | 5 | 1 | — | 5 | 4 |
| | 0.2 | 1 | 0 | 3 | 5 | 0 | — | 5 | 1 |
| 360 | 0.8 | 3 | 1 | 5 | 5 | 1 | — | 5 | 5 |
| | 0.2 | 1 | 0 | 4 | 5 | — | — | 5 | 3 |
| 361 | 0.8 | 3 | 1 | 4 | 4 | 1 | — | 5 | 4 |
| | 0.2 | 1 | 0 | 3 | 3 | 0 | — | 5 | 0 |
| 362 | 0.8 | 3 | 1 | 4 | 5 | 1 | — | 5 | 5 |
| | 0.2 | 1 | 0 | 5 | 5 | 0 | — | 5 | 3 |
| 363 | 5 | 5 | 3 | 5 | 5 | 2 | — | 5 | 5 |
| | 0.8 | 3 | 1 | 4 | 5 | 1 | — | 5 | 4 |
| 364 | 0.8 | 3 | 1 | 5 | 5 | 1 | — | 5 | 4 |
| | 0.2 | 1 | 0 | 3 | 5 | 0 | — | 5 | 2 |
| 365 | 0.8 | 2 | 1 | 5 | 5 | 1 | — | 5 | 4 |
| | 0.2 | 0 | 0 | 4 | 5 | 0 | — | 5 | 1 |
| 366 | 0.8 | 3 | 1 | 4 | 4 | 1 | — | 5 | 3 |
| | 0.2 | 1 | 0 | 3 | 2 | 0 | — | 5 | 0 |
| 367 | 0.8 | 2 | 1 | 4 | 4 | 1 | — | 5 | 3 |
| | 0.2 | 0 | 0 | 3 | 2 | 0 | — | 0 | 0 |
| 368 | 5 | 4 | 3 | 5 | 5 | 2 | — | 5 | 5 |
| | 0.8 | 2 | 1 | 5 | 5 | 1 | — | 5 | 5 |
| 369 | 0.8 | 3 | 2 | 5 | 5 | 2 | — | 5 | 5 |
| | 0.2 | 1 | 2 | 4 | 5 | 0 | — | 5 | 2 |
| 370 | 0.8 | 3 | 2 | 4 | 5 | 2 | — | 5 | 4 |
| | 0.2 | 0 | 1 | 2 | 4 | 0 | — | 4 | 0 |
| 371 | 0.8 | 3 | 1 | 5 | 5 | 1 | — | 5 | 4 |
| | 0.2 | 1 | 0 | 3 | 4 | 0 | — | 5 | 2 |
| 372 | 0.8 | 4 | 4 | 5 | 5 | 5 | — | 5 | 5 |
| | 0.2 | 2 | 2 | 5 | 4 | 4 | — | 5 | 4 |
| 373 | 0.8 | 4 | 4 | 5 | 5 | 4 | — | 5 | 5 |
| | 0.2 | 2 | 2 | 5 | 5 | 3 | — | 5 | 4 |
| 374 | 0.8 | 5 | 4 | 5 | 5 | 4 | — | 5 | 5 |
| | 0.2 | 3 | 2 | 5 | 5 | 2 | — | 5 | 5 |
| 375 | 0.8 | 5 | 4 | 5 | 5 | 4 | — | 5 | 5 |
| | 0.2 | 3 | 2 | 5 | 5 | 2 | — | 5 | 5 |
| 376 | 0.8 | 5 | 4 | 5 | 5 | 4 | — | 5 | 5 |
| | 0.2 | 3 | 2 | 5 | 5 | 2 | — | 5 | 5 |
| 377 | 0.8 | 3 | 3 | 5 | 5 | 5 | — | 5 | 5 |
| | 0.2 | 1 | 1 | 4 | 5 | 3 | — | 5 | 4 |
| 378 | 5 | 3 | 1 | 5 | 5 | 1 | — | 5 | 5 |
| | 0.8 | 0 | 0 | 1 | 0 | 0 | — | 4 | — |
| 379 | 5 | 3 | 3 | 4 | 5 | 2 | — | 5 | 5 |
| | 0.8 | 1 | 1 | 3 | 3 | 1 | — | 5 | 5 |
| 380 | 5 | 3 | 1 | 3 | 4 | 1 | — | 5 | 3 |
| | 0.8 | 1 | 0 | 2 | 2 | 0 | — | 4 | 2 |
| 381 | 5 | 2 | 3 | 3 | 5 | 1 | — | 5 | 3 |
| | 0.8 | 0 | 1 | 2 | 4 | 0 | — | 5 | 2 |
| 382 | 5 | 2 | 2 | 5 | 5 | 1 | — | 5 | 5 |
| | 0.8 | 0 | 0 | 4 | 3 | 0 | — | 5 | 5 |
| 383 | 5 | 3 | 2 | 5 | 5 | 1 | — | 5 | 3 |
| | 0.8 | 1 | 0 | 3 | 4 | 0 | — | 5 | — |
| 384 | 5 | 3 | 2 | 4 | 4 | 1 | — | 5 | 2 |
| | 0.8 | 1 | 0 | 3 | 2 | 0 | — | 5 | — |
| 385 | 5 | 4 | 3 | 4 | 4 | 1 | — | 5 | 2 |
| | 0.8 | 2 | 1 | 3 | 2 | 0 | — | 5 | — |
| 386 | 5 | 3 | 1 | 4 | 5 | 1 | — | 5 | 5 |
| | 0.8 | 0 | 0 | 2 | 3 | 0 | — | 5 | 4 |
| 388 | 5 | 3 | 2 | 4 | 5 | 1 | — | 5 | 5 |
| | 0.8 | 1 | 0 | 3 | 4 | 0 | — | 5 | 5 |
| 389 | 5 | 3 | 2 | 4 | 5 | 1 | — | 5 | 5 |
| | 0.8 | 1 | 0 | 3 | 4 | 0 | — | 5 | 5 |
| 390 | 5 | 3 | 3 | 4 | 5 | 1 | — | 5 | 5 |
| | 0.8 | 1 | 1 | 3 | 5 | 0 | — | 5 | 5 |
| 391 | 5 | 3 | 2 | 4 | 3 | 0 | — | 5 | 5 |
| | 0.8 | 1 | 0 | 3 | 1 | 0 | — | 5 | 5 |

TABLE 7-continued

| Comp'd No. | Amount of active ingredient Kg/ha | Phytotoxicity wheat | Phytotoxicity soybean | Pre-emergence treatment barnyard-grass | velvet-leaf | cocklebur | jimsonweed | birdseye speedwell | cleavers |
|---|---|---|---|---|---|---|---|---|---|
| 392 | 5 | 2 | 1 | 4 | 4 | 1 | — | 5 | 5 |
|  | 0.8 | 0 | 0 | 2 | 1 | 0 | — | 5 | 4 |
| 393 | 5 | 3 | 2 | 4 | 4 | 1 | — | 5 | 5 |
|  | 0.8 | 0 | 0 | 2 | 2 | 0 | — | 5 | 5 |
| 394 | 5 | 3 | 3 | 4 | 4 | 0 | — | 5 | 5 |
|  | 0.8 | 1 | 1 | 2 | 2 | 0 | — | 5 | 5 |
| 395 | 5 | 3 | 2 | 4 | 5 | 1 | — | 5 | 5 |
|  | 0.8 | 1 | 0 | 2 | 2 | 0 | — | 5 | 5 |
| 396 | 5 | 2 | 1 | 4 | 3 | 1 | — | 5 | 4 |
|  | 0.8 | 0 | 0 | 2 | 0 | 0 | — | 5 | 0 |
| 398 | 5 | 2 | 1 | 3 | 3 | 1 | — | 5 | 3 |
| 399 | 5 | 2 | 1 | 4 | 3 | 1 | — | 5 | 3 |
|  | 0.8 | 0 | 0 | 2 | 1 | 0 | — | 5 | 0 |
| 400 | 5 | 2 | 1 | 4 | 4 | 1 | — | 5 | 4 |
|  | 0.8 | 0 | 0 | 3 | 2 | 0 | — | 5 | 2 |
| 401 | 5 | 3 | 3 | 5 | 5 | 5 | — | 5 | 5 |
|  | 0.8 | 1 | 1 | 4 | 3 | 4 | — | 5 | 4 |
| 402 | 5 | 3 | 3 | 5 | 5 | 5 | — | 5 | 5 |
|  | 0.8 | 1 | 1 | 4 | 5 | 4 | — | 5 | 5 |
| 403 | 0.8 | 4 | 3 | 5 | 5 | 2 | — | 5 | 5 |
|  | 0.2 | 2 | 1 | 4 | 5 | 1 | — | 5 | 4 |
| 404 | 4 | 5 | 4 | 5 | 5 | 3 | — | 5 | 5 |
|  | 0.8 | 3 | 2 | 5 | 5 | 1 | — | 5 | 5 |
| 405 | 5 | 4 | 3 | 4 | 5 | 1 | — | 5 | 5 |
|  | 0.8 | 2 | 1 | 3 | 4 | 0 | — | 5 | 4 |
| 406 | 5 | 4 | 3 | 4 | 5 | 1 | — | 5 | 5 |
|  | 0.8 | 2 | 1 | 3 | 4 | 0 | — | 5 | 4 |
| A | 5 | 0 | 0 | 0 | 0 | 0 | 0 | 0 | 0 |
| B | 5 | 0 | 0 | 0 | 0 | 0 | 0 | 0 | 0 |
| C | 5 | 0 | 0 | 0 | 0 | 0 | 0 | 0 | 0 |
| D | 5 | 0 | 0 | 0 | 0 | 0 | 0 | 0 | 0 |

As shown in table 7, the present 3-(substituted phenyl)-pyrazole derivatives or salt thereof, represented by the general formula (I), exhibit more excellent controlling effects of weeds than comparative compound A, B, C or D at pre-emergence treatment in paddy fields. Ever when the derivatives exhibit both herbicidal activity on weeds and phytotoxicity on crops at the same dosage, however, by the selection of a proper lower dosage, sufficient herbicidal activity is retained but phytotoxicity on crops is reduced remarkably.

TEST EXAMPLE 4

Herbicidal effect on upland field weeds of post-emergence stage.

Polyethylene vats of 10 cm W×20 cm L×5 cm depth were filled with soil, and planted with seeds of upland field weeds shown below and with seeds of soybean and wheat as upland field crops. These weeds and crops were grown to leaf stages shown below. Then these weeds and crops were sprayed separately with solutions containing compounds (listed in Table 1) of the present invention as active ingredient at a predetermined concentration. 14 Days later, the herbicidal effect was examined, the percentages of killed weeds were calculated in the same manner as in Test Example 1, and the phytotoxicity of soybean and wheat plants were examined and judged according to the criterion shown in Test Example 1.

| Species of test weeds and leaf stage thereof and leaf stages of test soybean and wheat plants | |
|---|---|
| Barnyardgrass | 2-leaf stage |
| Velvetleaf | 2-leaf stage |
| Cocklebur | 1-leaf stage |
| Jimsonweed | 1-leaf stage |
| Birdseye Speedwell | 1-leaf stage |
| Cleavers | 2-leaf stage |
| Wheat | 2-leaf stage |
| Soybean | 1-leaf stage |

Results of the test are shown in Table 8.

TABLE 8

| Com'd. No. | Amount of active ingredient Kg/ha | Phytotoxicity wheat | Phytotoxicity soybean | post-emergence treatment barnyard grass | velvetleaf | cocklebur | jimsonweed | birdseye speedwell | cleavers |
|---|---|---|---|---|---|---|---|---|---|
| 2 | 5 | 1 | 2 | 2 | 5 | 4 | 5 | — | — |
| 3 | 5 | 2 | 4 | 5 | 4 | 4 | 4 | — | 4 |
| 4 | 5 | 5 | 5 | 5 | 5 | 5 | 5 | — | 5 |
|  | 0.2 | 3 | 4 | 4 | 5 | 5 | 5 | — | 5 |
| 5 | 5 | 5 | 5 | 5 | 5 | 5 | 5 | — | 5 |
|  | 0.2 | 3 | 4 | 5 | 5 | 5 | 5 | — | 5 |
| 6 | 5 | 3 | 5 | 5 | 5 | 5 | 5 | — | 5 |
| 7 | 5 | 2 | 4 | 4 | 5 | 5 | 5 | — | 4 |
| 8 | 5 | 1 | 4 | 2 | 5 | 2 | 5 | — | 1 |
| 9 | 5 | 5 | 5 | 4 | 5 | 5 | 5 | — | 5 |
|  | 0.8 | 3 | 5 | 2 | 5 | 5 | 5 | — | 5 |
| 10 | 0.8 | 5 | 5 | 5 | 5 | 5 | 5 | — | 5 |

TABLE 8-continued

| Com'd. No. | Amount of active ingredient Kg/ha | Phytotoxicity wheat | Phytotoxicity soybean | post-emergence treatment barnyard grass | velvetleaf | cocklebur | jimson-weed | birdseye speedwell | cleavers |
|---|---|---|---|---|---|---|---|---|---|
|  | 0.1 | 4 | 5 | 4 | 5 | 5 | 5 | — | 5 |
| 11 | 5 | 5 | 5 | 5 | 5 | 5 | 5 | — | 5 |
|  | 0.1 | 4 | 4 | 4 | 5 | 5 | 5 | — | 5 |
| 12 | 0.8 | 5 | 5 | 4 | 5 | 5 | 5 | — | 5 |
|  | 0.2 | 3 | 4 | 3 | 5 | 5 | 5 | — | 5 |
| 13 | 0.8 | 5 | 5 | 4 | 5 | 5 | 5 | — | 5 |
|  | 0.1 | 4 | 4 | 3 | 5 | 5 | 5 | — | 5 |
| 14 | 0.8 | 5 | 5 | 4 | 5 | 5 | 5 | — | 5 |
|  | 0.2 | 3 | 4 | 3 | 5 | 5 | 5 | — | 5 |
| 15 | 5 | 2 | 3 | 2 | 5 | 5 | 5 | — | 5 |
| 16 | 5 | 2 | 3 | 3 | 5 | 4 | 5 | — | 4 |
| 17 | 5 | 2 | 2 | 3 | 5 | 4 | 5 | — | 4 |
| 18 | 5 | 2 | 5 | 3 | 5 | 4 | 5 | — | 5 |
| 19 | 5 | 5 | 5 | 5 | 5 | 5 | 5 | — | 5 |
|  | 0.8 | 3 | 3 | 3 | 5 | 4 | 5 | — | 5 |
| 20 | 5 | 3 | 5 | 4 | 5 | 5 | 5 | — | 5 |
| 21 | 5 | 5 | 5 | 4 | 5 | 5 | 5 | — | 5 |
|  | 0.8 | 2 | 3 | 2 | 5 | 5 | 4 | — | 5 |
| 22 | 5 | 1 | 2 | 2 | 5 | 3 | 5 | — | 4 |
| 23 | 5 | 2 | 2 | 2 | 5 | 5 | 5 | — | 5 |
| 24 | 5 | 2 | 2 | 1 | 5 | 3 | 4 | — | 4 |
| 25 | 5 | 3 | 5 | 4 | 5 | 5 | 5 | — | 5 |
| 26 | 0.8 | 5 | 5 | 4 | 5 | 5 | 5 | — | 5 |
|  | 0.2 | 3 | 5 | 2 | 5 | 5 | 5 | — | 5 |
| 27 | 5 | 5 | 5 | 5 | 5 | 5 | 5 | — | 5 |
|  | 0.8 | 4 | 5 | 3 | 5 | 5 | 5 | — | 5 |
| 28 | 0.8 | 5 | 5 | 4 | 5 | 5 | 5 | — | 5 |
|  | 0.1 | 3 | 4 | 2 | 5 | 5 | 5 | — | 5 |
| 29 | 5 | 5 | 5 | 5 | 5 | 5 | 5 | — | 5 |
|  | 0.1 | 4 | 5 | 4 | 5 | 5 | 5 | — | 5 |
| 30 | 5 | 5 | 5 | 5 | 5 | 5 | 5 | — | 5 |
|  | 0.8 | 4 | 5 | 3 | 5 | 5 | 5 | — | 5 |
| 31 | 5 | 5 | 5 | 5 | 5 | 5 | 5 | — | 5 |
|  | 0.2 | 3 | 5 | 2 | 5 | 5 | 5 | — | 5 |
| 32 | 0.8 | 5 | 5 | 3 | 5 | 5 | 5 | — | 5 |
|  | 0.1 | 3 | 4 | 3 | 5 | 5 | 5 | — | 5 |
| 33 | 5 | 5 | 5 | 5 | 5 | 5 | 5 | — | 5 |
|  | 0.8 | 3 | 5 | 3 | 5 | 5 | 5 | — | 5 |
| 34 | 5 | 5 | 5 | 5 | 5 | 5 | 5 | — | 5 |
|  | 0.8 | 3 | 5 | 3 | 5 | 5 | 5 | — | 5 |
| 35 | 5 | 4 | 4 | 4 | 5 | 5 | 5 | — | 5 |
|  | 0.8 | 2 | 2 | 2 | 5 | 5 | 5 | — | 5 |
| 36 | 5 | 0 | 1 | 0 | 4 | 4 | 5 | — | 3 |
| 37 | 5 | 2 | 5 | 4 | 5 | 5 | 5 | — | 5 |
| 38 | 5 | 2 | 5 | 3 | 5 | 5 | 5 | — | 5 |
| 40 | 5 | 0 | 2 | 2 | 5 | 4 | 5 | — | 5 |
| 41 | 5 | 0 | 3 | 0 | 5 | 0 | 5 | — | 5 |
| 42 | 5 | 2 | 5 | 3 | 5 | 5 | 5 | — | 5 |
| 43 | 5 | 2 | 3 | 2 | 5 | 3 | 5 | — | 5 |
| 44 | 5 | 2 | 3 | 3 | 5 | 4 | 5 | — | 5 |
| 45 | 5 | 2 | 5 | 3 | 5 | 5 | 5 | — | 5 |
| 46 | 5 | 3 | 4 | 3 | 5 | 4 | 5 | — | 5 |
| 47 | 5 | 1 | 2 | 3 | 5 | 4 | 5 | — | 5 |
| 48 | 5 | 2 | 5 | 2 | 5 | 4 | 5 | — | 5 |
| 49 | 5 | 4 | 5 | 5 | 5 | 5 | 5 | — | 5 |
| 50 | 5 | 5 | 5 | 5 | 5 | 5 | 5 | — | 5 |
|  | 0.2 | 3 | 5 | 5 | 5 | 5 | 5 | — | 5 |
| 51 | 5 | 3 | 5 | 5 | 5 | 5 | 5 | — | 5 |
| 52 | 5 | 2 | 4 | 3 | 5 | 5 | 5 | — | 5 |
| 54 | 5 | 2 | 5 | 4 | 5 | 5 | 5 | — | 5 |
| 55 | 5 | 0 | 2 | 1 | 5 | 3 | 5 | — | 4 |
| 56 | 5 | 0 | 3 | 1 | 5 | 2 | 5 | — | 1 |
| 57 | 5 | 0 | 2 | 2 | 4 | 2 | 5 | — | 4 |
| 58 | 5 | 0 | 2 | 0 | 4 | 3 | 5 | — | 4 |
| 59 | 5 | 1 | 2 | 2 | 4 | 4 | 5 | — | — |
| 60 | 5 | 0 | 2 | 0 | 3 | 4 | 4 | — | 3 |
| 62 | 5 | 4 | 5 | 4 | 5 | 5 | — | 5 | 5 |
|  | 0.8 | 2 | 3 | 2 | 5 | 5 | — | 5 | 5 |
| 63 | 5 | 4 | 5 | 4 | 5 | 5 | — | 5 | 5 |
|  | 0.8 | 2 | 4 | 2 | 5 | 5 | — | 5 | 5 |
| 64 | 5 | 5 | 5 | 5 | 5 | 5 | — | 5 | 5 |
|  | 0.8 | 3 | 3 | 3 | 5 | 5 | — | 5 | 5 |
| 66 | 5 | 4 | 5 | 4 | 5 | 5 | — | 5 | 5 |
|  | 0.8 | 2 | 4 | 2 | 5 | 5 | — | 5 | 5 |
| 67 | 5 | 3 | 5 | 3 | 5 | 5 | — | 5 | 5 |
|  | 0.8 | 1 | 3 | 1 | 5 | 5 | — | 5 | 5 |
| 68 | 0.8 | 3 | 5 | 3 | 5 | 5 | — | 5 | 5 |

TABLE 8-continued

| Com'd. No. | Amount of active ingredient Kg/ha | Phytotoxicity wheat | Phytotoxicity soybean | post-emergence treatment barnyard grass | velvetleaf | cocklebur | jimson-weed | birdseye speedwell | cleavers |
|---|---|---|---|---|---|---|---|---|---|
| 70 | 5 | 0 | 1 | 0 | 1 | 1 | 3 | — | 0 |
| 71 | 5 | 3 | 5 | 5 | 5 | 5 | 5 | — | 5 |
| 72 | 5 | 2 | 4 | 4 | 5 | 5 | 5 | — | 5 |
| 73 | 5 | 1 | 3 | 1 | 5 | 3 | 5 | — | 2 |
| 74 | 5 | 1 | 3 | 1 | 5 | 2 | 5 | — | 2 |
| 75 | 5 | 1 | 2 | 1 | 5 | 2 | 5 | — | 1 |
| 76 | 5 | 2 | 1 | 2 | 5 | 2 | 5 | — | 2 |
| 77 | 5 | 2 | 5 | 4 | 5 | 5 | 5 | — | 4 |
| 78 | 5 | 1 | 4 | 3 | 5 | 4 | 5 | — | 3 |
| 79 | 5 | 1 | 2 | 1 | 5 | 2 | 5 | — | 3 |
| 81 | 0.8 | 5 | 5 | 5 | 5 | 5 | 5 | — | 5 |
|  | 0.2 | 3 | 5 | 5 | 5 | 5 | 5 | — | 5 |
| 82 | 0.8 | 5 | 5 | 5 | 5 | 5 | 5 | — | 5 |
|  | 0.2 | 3 | 5 | 5 | 5 | 5 | 5 | — | 5 |
| 83 | 0.8 | 5 | 5 | 5 | 5 | 5 | 5 | — | 5 |
|  | 0.2 | 3 | 4 | 3 | 5 | 5 | 5 | — | 5 |
| 84 | 0.8 | 5 | 5 | 5 | 5 | 5 | 5 | — | 5 |
|  | 0.2 | 3 | 5 | 4 | 5 | 5 | 5 | — | 5 |
| 85 | 0.8 | 5 | 5 | 5 | 5 | 5 | 5 | — | 5 |
|  | 0.2 | 3 | 3 | 4 | 5 | 5 | 5 | — | 5 |
| 86 | 0.8 | 5 | 5 | 5 | 5 | 5 | 5 | — | 5 |
|  | 0.2 | 3 | 5 | 5 | 5 | 5 | 5 | — | 5 |
| 87 | 0.8 | 5 | 5 | 5 | 5 | 5 | 5 | — | 5 |
|  | 0.1 | 4 | 5 | 5 | 5 | 5 | 5 | — | 5 |
| 88 | 0.8 | 5 | 5 | 5 | 5 | 5 | 5 | — | 5 |
|  | 0.1 | 3 | 5 | 5 | 5 | 5 | 5 | — | 5 |
| 89 | 5 | 5 | 5 | 5 | 5 | 5 | — | 5 | 5 |
|  | 0.8 | 4 | 5 | 4 | 5 | 5 | — | 5 | 5 |
| 90 | 0.8 | 5 | 5 | 5 | 5 | 5 | 5 | — | 5 |
|  | 0.2 | 3 | 3 | 3 | 5 | 5 | 5 | — | 5 |
| 91 | 5 | 5 | 5 | 5 | 5 | 5 | 5 | — | 5 |
|  | 0.8 | 3 | 5 | 5 | 5 | 5 | 5 | — | 5 |
| 92 | 5 | 5 | 5 | 5 | 5 | 5 | — | 5 | 5 |
|  | 0.8 | 2 | 5 | 4 | 5 | 5 | — | 5 | 5 |
| 93 | 5 | 5 | 5 | 5 | 5 | 5 | — | 5 | 5 |
|  | 0.8 | 2 | 5 | 4 | 5 | 5 | — | 5 | 5 |
| 94 | 5 | 5 | 5 | 5 | 5 | 5 | — | 5 | 5 |
|  | 0.8 | 3 | 5 | 5 | 5 | 5 | — | 5 | 5 |
| 95 | 5 | 5 | 5 | 5 | 5 | 5 | — | 5 | 5 |
|  | 0.8 | 2 | 5 | 4 | 5 | 5 | — | 5 | 5 |
| 96 | 5 | 5 | 5 | 5 | 5 | 5 | — | 5 | 5 |
|  | 0.8 | 2 | 5 | 4 | 5 | 5 | — | 5 | 5 |
| 97 | 5 | 5 | 5 | 5 | 5 | 5 | — | 5 | 5 |
|  | 0.8 | 2 | 5 | 4 | 5 | 5 | — | 5 | 5 |
| 98 | 5 | 5 | 5 | 5 | 5 | 5 | — | 5 | 5 |
|  | 0.8 | 2 | 5 | 4 | 5 | 5 | — | 5 | 5 |
| 99 | 5 | 5 | 5 | 5 | 5 | 5 | — | 5 | 5 |
|  | 0.8 | 2 | 5 | 4 | 5 | 5 | — | 5 | 5 |
| 100 | 5 | 5 | 5 | 4 | 5 | 5 | — | 5 | 5 |
|  | 0.8 | 2 | 5 | 3 | 5 | 5 | — | 5 | 5 |
| 101 | 5 | 5 | 5 | 5 | 5 | 5 | — | 5 | 5 |
|  | 0.8 | 2 | 5 | 4 | 5 | 5 | — | 5 | 5 |
| 102 | 5 | 5 | 5 | 5 | 5 | 5 | — | 5 | 5 |
|  | 0.8 | 2 | 5 | 4 | 5 | 5 | — | 5 | 5 |
| 103 | 5 | 5 | 5 | 5 | 5 | 5 | 5 | — | 5 |
|  | 0.8 | 3 | 4 | 3 | 5 | 5 | 5 | — | 5 |
| 104 | 5 | 5 | 5 | 5 | 5 | 5 | 5 | — | 5 |
|  | 0.8 | 3 | 4 | 3 | 5 | 5 | 5 | — | 5 |
| 105 | 5 | 5 | 5 | 5 | 5 | 5 | 5 | — | 5 |
|  | 0.8 | 4 | 5 | 5 | 5 | 5 | 5 | — | 5 |
| 106 | 5 | 5 | 5 | 5 | 5 | 5 | — | 5 | 5 |
|  | 0.8 | 3 | 5 | 5 | 5 | 5 | — | 5 | 5 |
| 107 | 5 | 5 | 5 | 5 | 5 | 5 | — | 5 | 5 |
|  | 0.8 | 3 | 5 | 4 | 5 | 5 | — | 5 | 5 |
| 108 | 5 | 5 | 5 | 5 | 5 | 5 | — | 5 | 5 |
|  | 0.8 | 3 | 5 | 5 | 5 | 5 | — | 5 | 5 |
| 109 | 5 | 5 | 5 | 5 | 5 | 5 | 5 | — | 5 |
|  | 0.8 | 4 | 5 | 5 | 5 | 5 | 5 | — | 5 |
| 110 | 5 | 5 | 5 | 5 | 5 | 5 | 5 | — | 5 |
|  | 0.8 | 4 | 5 | 5 | 5 | 5 | 5 | — | 5 |
| 111 | 5 | 4 | 5 | 4 | 5 | 5 | 5 | — | 5 |
|  | 0.8 | 2 | 5 | 2 | 5 | 4 | 5 | — | 4 |
| 112 | 0.8 | 5 | 5 | 5 | 5 | 5 | 5 | — | 5 |
|  | 0.2 | 3 | 5 | 4 | 5 | 5 | 5 | — | 5 |
| 113 | 0.8 | 5 | 5 | 5 | 5 | 5 | 5 | — | 5 |
|  | 0.2 | 3 | 5 | 5 | 5 | 5 | 5 | — | 5 |
| 114 | 5 | 4 | 5 | 5 | 5 | 5 | 5 | — | 5 |

TABLE 8-continued

| Com'd. No. | Amount of active ingredient Kg/ha | Phytotoxicity wheat | Phytotoxicity soybean | post-emergence treatment barnyard grass | velvetleaf | cocklebur | jimson-weed | birdseye speedwell | cleavers |
|---|---|---|---|---|---|---|---|---|---|
|  | 0.8 | 2 | 5 | 4 | 5 | 5 | 5 | — | 5 |
| 115 | 5 | 4 | 5 | 5 | 5 | 5 | 5 | — | 5 |
|  | 0.8 | 2 | 5 | 4 | 5 | 5 | 5 | — | 5 |
| 116 | 5 | 5 | 5 | 5 | 5 | 5 | 5 | — | 5 |
|  | 0.8 | 3 | 5 | 4 | 5 | 5 | 5 | — | 5 |
| 117 | 0.8 | 5 | 5 | 5 | 5 | 5 | 5 | — | 5 |
|  | 0.2 | 3 | 3 | 3 | 5 | 5 | 5 | — | 5 |
| 118 | 5 | 5 | 5 | 5 | 5 | 5 | — | 5 | 5 |
|  | 0.8 | 3 | 5 | 3 | 5 | 5 | — | 5 | 5 |
| 119 | 0.8 | 5 | 5 | 5 | 5 | 5 | 5 | — | 5 |
|  | 0.2 | 3 | 5 | 3 | 5 | 5 | 5 | — | 5 |
| 120 | 5 | 4 | 5 | 4 | 5 | 5 | 5 | — | 5 |
|  | 0.8 | 2 | 3 | 3 | 5 | 5 | 5 | — | 5 |
| 121 | 5 | 5 | 5 | 5 | 5 | 5 | 5 | — | 5 |
|  | 0.8 | 3 | 5 | 4 | 5 | 5 | 5 | — | 5 |
| 122 | 0.8 | 5 | 5 | 5 | 5 | 5 | 5 | — | 5 |
|  | 0.2 | 3 | 5 | 3 | 5 | 5 | 5 | — | 5 |
| 123 | 5 | 5 | 5 | 5 | 5 | 5 | 5 | — | 5 |
|  | 0.8 | 3 | 5 | 4 | 5 | 5 | 5 | — | 5 |
| 124 | 5 | 3 | 3 | 2 | 5 | 5 | 5 | — | 4 |
|  | 0.8 | 0 | 1 | 0 | 4 | 4 | 5 | — | 3 |
| 125 | 5 | 5 | 5 | 5 | 5 | 5 | — | 5 | 5 |
|  | 0.8 | 3 | 5 | 4 | 5 | 5 | — | 5 | 5 |
| 126 | 0.8 | 5 | 5 | 5 | 5 | 5 | 5 | — | 5 |
|  | 0.2 | 3 | 5 | 4 | 5 | 5 | 5 | — | 5 |
| 127 | 5 | 5 | 5 | 5 | 5 | 5 | 5 | — | 5 |
|  | 0.8 | 3 | 5 | 5 | 5 | 5 | 5 | — | 5 |
| 128 | 5 | 5 | 5 | 5 | 5 | 5 | 5 | — | 5 |
|  | 0.8 | 3 | 5 | 5 | 5 | 5 | 5 | — | 5 |
| 129 | 0.8 | 5 | 5 | 5 | 5 | 5 | 5 | — | 5 |
|  | 0.2 | 3 | 5 | 5 | 5 | 5 | 5 | — | 5 |
| 130 | 5 | 5 | 5 | 5 | 5 | 5 | 5 | — | 5 |
|  | 0.8 | 3 | 5 | 5 | 5 | 5 | 5 | — | 5 |
| 131 | 0.8 | 5 | 5 | 5 | 5 | 5 | 5 | — | 5 |
|  | 0.2 | 3 | 5 | 3 | 5 | 5 | 5 | — | 5 |
| 132 | 5 | 5 | 5 | 5 | 5 | 5 | 5 | — | 5 |
|  | 0.8 | 3 | 5 | 5 | 5 | 5 | 5 | — | 5 |
| 133 | 0.8 | 5 | 5 | 5 | 5 | 5 | 5 | — | 5 |
|  | 0.2 | 3 | 5 | 4 | 5 | 5 | 5 | — | 5 |
| 134 | 5 | 5 | 5 | 5 | 5 | 5 | 5 | — | 5 |
|  | 0.8 | 3 | 5 | 4 | 5 | 5 | 5 | — | 5 |
| 135 | 5 | 5 | 5 | 5 | 5 | 5 | 5 | — | 5 |
|  | 0.8 | 3 | 5 | 5 | 5 | 5 | 5 | — | 5 |
| 136 | 5 | 5 | 5 | 5 | 5 | 5 | 5 | — | 5 |
|  | 0.8 | 3 | 5 | 5 | 5 | 5 | 5 | — | 5 |
| 137 | 5 | 5 | 5 | 5 | 5 | 5 | 5 | — | 5 |
|  | 0.8 | 3 | 5 | 5 | 5 | 5 | 5 | — | 5 |
| 138 | 5 | 5 | 5 | 5 | 5 | 5 | 5 | — | 5 |
|  | 0.8 | 3 | 5 | 4 | 5 | 5 | 5 | — | 5 |
| 139 | 5 | 5 | 5 | 5 | 5 | 5 | 5 | — | 5 |
|  | 0.8 | 3 | 5 | 5 | 5 | 5 | 5 | — | 5 |
| 140 | 5 | 5 | 5 | 5 | 5 | 5 | 5 | — | 5 |
|  | 0.8 | 4 | 5 | 5 | 5 | 5 | 5 | — | 5 |
| 141 | 5 | 5 | 5 | 5 | 5 | 5 | 5 | — | 5 |
|  | 0.8 | 3 | 5 | 5 | 5 | 5 | 5 | — | 5 |
| 142 | 5 | 5 | 5 | 5 | 5 | 5 | 5 | — | 5 |
|  | 0.8 | 3 | 4 | 5 | 5 | 5 | 5 | — | 5 |
| 143 | 5 | 5 | 5 | 5 | 5 | 5 | 5 | — | 5 |
|  | 0.8 | 3 | 5 | 4 | 5 | 5 | 5 | — | 5 |
| 144 | 5 | 5 | 5 | 5 | 5 | 5 | 5 | — | 5 |
|  | 0.8 | 3 | 4 | 3 | 5 | 5 | 5 | — | 5 |
| 145 | 5 | 5 | 5 | 5 | 5 | 5 | 5 | — | 5 |
|  | 0.8 | 3 | 4 | 5 | 5 | 5 | 5 | — | 5 |
| 146 | 5 | 3 | 5 | 5 | 5 | 5 | 5 | — | 5 |
| 147 | 5 | 4 | 5 | 5 | 5 | 5 | 5 | — | 5 |
| 148 | 5 | 3 | 5 | 5 | 5 | 5 | 5 | — | 5 |
| 149 | 5 | 3 | 5 | 4 | 5 | 5 | 5 | — | 5 |
| 150 | 5 | 5 | 5 | 5 | 5 | 5 | 5 | — | 5 |
|  | 0.8 | 4 | 5 | 5 | 5 | 5 | 5 | — | 5 |
| 151 | 5 | 5 | 5 | 5 | 5 | 5 | 5 | — | 5 |
|  | 0.8 | 4 | 5 | 5 | 5 | 5 | 5 | — | 5 |
| 152 | 5 | 5 | 5 | 5 | 5 | 5 | 5 | — | 5 |
|  | 0.8 | 4 | 5 | 5 | 5 | 5 | 5 | — | 5 |
| 153 | 0.8 | 5 | 5 | 5 | 5 | 5 | 5 | — | 5 |
|  | 0.2 | 4 | 5 | 5 | 5 | 5 | 5 | — | 5 |
| 154 | 5 | 3 | 5 | 4 | 5 | 5 | 5 | — | 5 |
|  | 0.8 | 1 | 3 | 3 | 5 | 4 | 5 | — | 4 |

TABLE 8-continued

| Com'd. No. | Amount of active ingredient Kg/ha | Phytotoxicity | | post-emergence treatment | | | | | |
|---|---|---|---|---|---|---|---|---|---|
| | | wheat | soybean | barnyard grass | velvetleaf | cocklebur | jimson-weed | birdseye speedwell | cleavers |
| 155 | 5 | 5 | 5 | 5 | 5 | 5 | 5 | — | 5 |
| | 0.8 | 3 | 4 | 4 | 5 | 5 | 5 | — | 5 |
| 156 | 5 | 4 | 5 | 5 | 5 | 5 | 5 | — | 5 |
| | 0.8 | 2 | 4 | 4 | 5 | 5 | 5 | — | 5 |
| 157 | 5 | 5 | 5 | 5 | 5 | 5 | — | 5 | 5 |
| | 0.8 | 3 | 5 | 4 | 5 | 5 | — | 5 | 5 |
| 158 | 5 | 5 | 5 | 5 | 5 | 5 | 5 | — | 5 |
| | 0.8 | 3 | 3 | 4 | 5 | 5 | 5 | — | 5 |
| 159 | 5 | 5 | 5 | 5 | 5 | 5 | 5 | — | 5 |
| | 0.8 | 3 | 4 | 3 | 5 | 4 | 5 | — | 5 |
| 160 | 5 | 5 | 5 | 5 | 5 | 5 | 5 | — | 5 |
| | 0.8 | 3 | 5 | 4 | 5 | 5 | 5 | — | 5 |
| 161 | 5 | 5 | 5 | 5 | 5 | 5 | 5 | — | 5 |
| | 0.8 | 4 | 5 | 5 | 5 | 5 | 5 | — | 5 |
| 162 | 5 | 5 | 5 | 5 | 5 | 5 | 5 | — | 5 |
| | 0.8 | 4 | 5 | 4 | 5 | 5 | 5 | — | 5 |
| 163 | 5 | 5 | 5 | 5 | 5 | 5 | 5 | — | 5 |
| | 0.8 | 4 | 5 | 4 | 5 | 5 | 5 | — | 5 |
| 164 | 5 | 5 | 5 | 5 | 5 | 5 | 5 | — | 5 |
| | 0.8 | 3 | 5 | 4 | 5 | 5 | 5 | — | 5 |
| 165 | 5 | 4 | 5 | 4 | 5 | 5 | 5 | — | 5 |
| | 0.8 | 2 | 3 | 2 | 5 | 4 | 5 | — | 4 |
| 166 | 5 | 5 | 5 | 5 | 5 | 5 | 5 | — | 5 |
| | 0.8 | 2 | 5 | 3 | 5 | 5 | 5 | — | 5 |
| 167 | 5 | 5 | 5 | 5 | 5 | 5 | 5 | — | 5 |
| | 0.8 | 3 | 4 | 3 | 5 | 5 | 5 | — | 5 |
| 168 | 5 | 5 | 5 | 5 | 5 | 5 | 5 | — | 5 |
| | 0.8 | 3 | 5 | 3 | 5 | 5 | 5 | — | 5 |
| 169 | 5 | 5 | 5 | 5 | 5 | 5 | — | 5 | 5 |
| | 0.8 | 3 | 3 | 3 | 5 | 5 | — | 5 | 5 |
| 170 | 5 | 3 | 5 | 4 | 5 | 5 | — | 5 | 5 |
| | 0.8 | 1 | 4 | 2 | 5 | 5 | — | 5 | 4 |
| 171 | 5 | 5 | 5 | 5 | 5 | 5 | 5 | — | 5 |
| | 0.8 | 3 | 5 | 4 | 5 | 5 | 5 | — | 5 |
| 172 | 5 | 5 | 5 | 5 | 5 | 5 | 5 | — | 5 |
| | 0.8 | 4 | 5 | 4 | 5 | 5 | 5 | — | 5 |
| 173 | 5 | 3 | 5 | 4 | 5 | 5 | — | 5 | 5 |
| | 0.8 | 1 | 3 | 2 | 5 | 5 | — | 5 | 4 |
| 174 | 5 | 5 | 5 | 5 | 5 | 5 | 5 | — | 5 |
| | 0.8 | 3 | 5 | 4 | 5 | 5 | 5 | — | 5 |
| 175 | 0.8 | 5 | 5 | 4 | 5 | 5 | 5 | — | 5 |
| | 0.2 | 3 | 3 | 2 | 5 | 4 | 3 | — | 5 |
| 176 | 5 | 3 | 5 | 4 | 5 | 5 | 5 | — | 5 |
| | 0.8 | 1 | 5 | 2 | 5 | 5 | 5 | — | 5 |
| 177 | 5 | 5 | 5 | 5 | 5 | 5 | 5 | — | 5 |
| | 0.8 | 3 | 5 | 3 | 5 | 5 | 5 | — | 5 |
| 178 | 5 | 5 | 5 | 5 | 5 | 5 | 5 | — | 5 |
| | 0.8 | 3 | 5 | 4 | 5 | 5 | 5 | — | 5 |
| 179 | 5 | 5 | 5 | 5 | 5 | 5 | 5 | — | 5 |
| | 0.8 | 3 | 5 | 4 | 5 | 5 | 5 | — | 5 |
| 180 | 5 | 3 | 4 | 4 | 5 | 4 | 5 | — | 5 |
| | 0.8 | 1 | 2 | 2 | 5 | 3 | 5 | — | 4 |
| 181 | 5 | 4 | 5 | 4 | 5 | 5 | 5 | — | 5 |
| | 0.8 | 2 | 4 | 3 | 5 | 4 | 5 | — | 4 |
| 182 | 5 | 5 | 5 | 5 | 5 | 5 | 5 | — | 5 |
| | 0.8 | 3 | 5 | 4 | 5 | 5 | 5 | — | 5 |
| 183 | 5 | 5 | 5 | 5 | 5 | 5 | 5 | — | 5 |
| | 0.8 | 3 | 5 | 5 | 5 | 5 | 5 | — | 5 |
| 184 | 5 | 4 | 5 | 5 | 5 | 5 | 5 | — | 5 |
| | 0.8 | 2 | 5 | 3 | 5 | 5 | 5 | — | 5 |
| 185 | 5 | 4 | 5 | 4 | 5 | 5 | 5 | — | 5 |
| | 0.8 | 2 | 5 | 2 | 5 | 5 | 5 | — | 5 |
| 186 | 5 | 5 | 5 | 5 | 5 | 5 | 5 | — | 5 |
| | 0.8 | 3 | 5 | 3 | 5 | 5 | 5 | — | 5 |
| 187 | 5 | 3 | 5 | 4 | 5 | 5 | 5 | — | 5 |
| | 0.8 | 0 | 3 | 2 | 4 | 3 | 4 | — | 3 |
| 188 | 5 | 4 | 5 | 4 | 5 | 5 | 5 | — | 5 |
| | 0.8 | 2 | 5 | 3 | 5 | 5 | 5 | — | 5 |
| 189 | 5 | 5 | 5 | 5 | 5 | 5 | 5 | — | 5 |
| | 0.8 | 3 | 5 | 3 | 5 | 5 | 5 | — | 5 |
| 190 | 5 | 5 | 5 | 5 | 5 | 5 | — | 5 | 5 |
| | 0.8 | 4 | 5 | 4 | 5 | 5 | — | 5 | 5 |
| 191 | 5 | 5 | 5 | 5 | 5 | 5 | — | 5 | 5 |
| | 0.8 | 3 | 5 | 3 | 5 | 5 | — | 5 | 5 |
| 192 | 5 | 3 | 5 | 4 | 5 | 5 | — | 5 | 5 |
| | 0.8 | 1 | 3 | 2 | 5 | 5 | — | 5 | 5 |
| 193 | 5 | 3 | 3 | 3 | 5 | 4 | — | 4 | 4 |

TABLE 8-continued

| Com'd. No. | Amount of active ingredient Kg/ha | Phytotoxicity | | post-emergence treatment | | | | | |
|---|---|---|---|---|---|---|---|---|---|
| | | wheat | soybean | barnyard grass | velvetleaf | cocklebur | jimson-weed | birdseye speedwell | cleavers |
| | 0.8 | 0 | 0 | 1 | 4 | 2 | — | 2 | 2 |
| 194 | 5 | 5 | 5 | 5 | 5 | 5 | 5 | — | 5 |
| | 0.8 | 2 | 5 | 3 | 5 | 5 | 5 | — | 5 |
| 195 | 5 | 5 | 5 | 5 | 5 | 5 | 5 | — | 5 |
| | 0.8 | 3 | 5 | 3 | 5 | 5 | 5 | — | 5 |
| 196 | 0.8 | 5 | 5 | 4 | 5 | 5 | 5 | — | 5 |
| | 0.2 | 3 | 3 | 3 | 5 | 5 | 5 | — | 5 |
| 197 | 5 | 5 | 5 | 5 | 5 | 5 | 5 | — | 5 |
| | 0.8 | 4 | 5 | 4 | 5 | 5 | 5 | — | 5 |
| 198 | 5 | 5 | 5 | 5 | 5 | 5 | — | 5 | 5 |
| | 0.8 | 3 | 5 | 3 | 5 | 5 | — | 5 | 5 |
| 199 | 5 | 5 | 5 | 5 | 5 | 5 | — | 5 | 5 |
| | 0.8 | 3 | 4 | 3 | 5 | 5 | — | 5 | 5 |
| 200 | 5 | 5 | 5 | 5 | 5 | 5 | — | 5 | 5 |
| | 0.8 | 3 | 5 | 4 | 5 | 5 | — | 5 | 5 |
| 201 | 5 | 5 | 5 | 5 | 5 | 5 | — | 5 | 5 |
| | 0.8 | 3 | 5 | 4 | 5 | 5 | — | 5 | 5 |
| 202 | 5 | 4 | 5 | 4 | 5 | 5 | — | 5 | 5 |
| | 0.8 | 2 | 5 | 2 | 5 | 5 | — | 5 | 5 |
| 203 | 5 | 4 | 4 | 3 | 5 | 4 | — | 5 | 5 |
| | 0.8 | 2 | 2 | 1 | 5 | 3 | — | 5 | 4 |
| 204 | 5 | 5 | 5 | 5 | 5 | 5 | — | 5 | 5 |
| | 0.8 | 3 | 5 | 3 | 5 | 5 | — | 5 | 5 |
| 205 | 5 | 3 | 5 | 4 | 5 | 5 | 5 | — | 5 |
| | 0.8 | 1 | 5 | 3 | 5 | 3 | 5 | — | 4 |
| 206 | 5 | 4 | 5 | 4 | 5 | 5 | 5 | — | 5 |
| | 0.8 | 2 | 5 | 2 | 5 | 5 | 5 | — | 5 |
| 207 | 5 | 4 | 5 | 5 | 5 | 5 | 5 | — | 5 |
| | 0.8 | 2 | 3 | 3 | 5 | 4 | 5 | — | 5 |
| 208 | 5 | 5 | 5 | 5 | 5 | 5 | 5 | — | 5 |
| | 0.8 | 3 | 4 | 4 | 5 | 5 | 5 | — | 5 |
| 209 | 5 | 4 | 5 | 4 | 5 | 5 | 5 | — | — |
| | 0.8 | 2 | 3 | 2 | 5 | 4 | 5 | — | — |
| 210 | 5 | 3 | 4 | 4 | 5 | 5 | 5 | — | 5 |
| | 0.8 | 1 | 2 | 3 | 5 | 3 | 5 | — | 4 |
| 211 | 5 | 3 | 5 | 4 | 5 | 5 | 5 | — | 5 |
| | 0.8 | 1 | 4 | 2 | 5 | 4 | 5 | — | 5 |
| 212 | 5 | 5 | 5 | 5 | 5 | 5 | 5 | — | 5 |
| | 0.8 | 3 | 5 | 4 | 5 | 5 | 5 | — | 5 |
| 213 | 5 | 3 | 2 | 3 | 5 | 4 | 5 | — | 5 |
| | 0.8 | 1 | 0 | 1 | 3 | 3 | 5 | — | 3 |
| 214 | 5 | 3 | 5 | 4 | 5 | 5 | 5 | — | — |
| | 0.8 | 1 | 4 | 2 | 5 | 4 | 5 | — | — |
| 215 | 5 | 2 | 5 | 3 | 5 | 5 | 5 | — | 5 |
| 216 | 5 | 5 | 5 | 5 | 5 | 5 | — | 5 | 5 |
| | 0.8 | 3 | 4 | 3 | 5 | 5 | — | 5 | 5 |
| 218 | 5 | 4 | 5 | 3 | 5 | 5 | 5 | — | 5 |
| 220 | 5 | 5 | 5 | 5 | 5 | 5 | 5 | — | 5 |
| | 0.8 | 4 | 5 | 4 | 5 | 5 | 5 | — | 5 |
| 221 | 5 | 5 | 5 | 5 | 5 | 5 | 5 | — | 5 |
| | 0.8 | 3 | 5 | 3 | 5 | 5 | 5 | — | 5 |
| 222 | 0.8 | 5 | 5 | 4 | 5 | 5 | 5 | — | 5 |
| | 0.1 | 4 | 4 | 3 | 5 | 5 | 5 | — | 5 |
| 223 | 5 | 5 | 5 | 5 | 5 | 5 | — | 5 | 5 |
| | 0.8 | 3 | 5 | 5 | 5 | 5 | — | 5 | 5 |
| 224 | 5 | 5 | 5 | 5 | 5 | 5 | — | 5 | 5 |
| | 0.8 | 2 | 5 | 4 | 5 | 5 | — | 5 | 5 |
| 225 | 5 | 5 | 5 | 5 | 5 | 4 | — | 5 | 5 |
| | 0.8 | 2 | 2 | 3 | 4 | 2 | — | 4 | 3 |
| 226 | 5 | 5 | 5 | 5 | 5 | 4 | — | 4 | 5 |
| | 0.8 | 3 | 2 | 3 | 4 | 2 | — | 4 | 3 |
| 227 | 5 | 5 | 5 | 5 | 5 | 5 | — | 5 | 5 |
| | 0.8 | 3 | 3 | 3 | 5 | 4 | — | 4 | 4 |
| 228 | 0.8 | 5 | 3 | 5 | 5 | 5 | — | 5 | 5 |
| | 0.2 | 3 | 3 | 4 | 5 | 5 | — | 5 | 5 |
| 229 | 5 | 5 | 5 | 5 | 5 | 5 | — | 5 | 5 |
| | 0.8 | 3 | 2 | 4 | 5 | 5 | — | 5 | 5 |
| 230 | 5 | 5 | 5 | 5 | 5 | 5 | — | 5 | 5 |
| | 0.8 | 2 | 5 | 4 | 5 | 5 | — | 5 | 5 |
| 231 | 5 | 4 | 5 | 5 | 5 | 3 | — | 5 | 5 |
| | 0.8 | 2 | 5 | 4 | 5 | — | — | 5 | 5 |
| 232 | 5 | 5 | 5 | 5 | 5 | 5 | — | 5 | 5 |
| | 0.8 | 2 | 5 | 3 | 5 | 5 | — | 5 | 5 |
| 233 | 5 | 5 | 5 | 5 | 5 | 5 | — | 5 | 5 |
| | 0.8 | 2 | 5 | 4 | 5 | 5 | — | 5 | 5 |
| 234 | 5 | 5 | 5 | 5 | 5 | 5 | — | 5 | 5 |
| | 0.8 | 2 | 5 | 5 | 5 | 5 | — | 5 | 5 |

TABLE 8-continued

| Com'd. No. | Amount of active ingredient Kg/ha | Phytotoxicity | | post-emergence treatment | | | | | |
|---|---|---|---|---|---|---|---|---|---|
| | | wheat | soybean | barnyard grass | velvetleaf | cocklebur | jimson-weed | birdseye speedwell | cleavers |
| 235 | 5 | 5 | 5 | 5 | 5 | 5 | — | 5 | 5 |
| | 0.8 | 3 | 5 | 3 | 5 | 5 | — | 5 | 5 |
| 236 | 0.8 | 3 | 5 | 4 | 5 | 5 | — | 5 | 5 |
| | 0.2 | 1 | 4 | 2 | 5 | 5 | — | 5 | 5 |
| 237 | 5 | 4 | 5 | 5 | 5 | 5 | — | 5 | 5 |
| | 0.8 | 1 | 5 | 4 | 5 | 5 | — | 5 | 5 |
| 238 | 5 | 5 | 5 | 5 | 5 | 5 | — | 5 | 5 |
| | 0.8 | 2 | 5 | 4 | 5 | 5 | — | 5 | 5 |
| 239 | 5 | 5 | 5 | 5 | 5 | 5 | — | 5 | 5 |
| | 0.8 | 2 | 5 | 5 | 5 | 5 | — | 5 | 5 |
| 240 | 5 | 5 | 5 | 5 | 5 | 5 | — | 5 | 5 |
| | 0.8 | 2 | 5 | 5 | 5 | 5 | — | 5 | 5 |
| 241 | 5 | 4 | 5 | 5 | 5 | 5 | — | 5 | 5 |
| | 0.8 | 2 | 5 | 3 | 5 | 5 | — | 5 | 4 |
| 242 | 5 | 5 | 5 | 5 | 5 | 5 | — | 5 | 5 |
| | 0.8 | 3 | 5 | 3 | 5 | 5 | — | 5 | 5 |
| 243 | 0.8 | 3 | 4 | 4 | 5 | 5 | — | 5 | 5 |
| | 0.2 | 1 | 2 | 2 | 5 | 5 | — | 3 | 5 |
| 244 | 5 | 5 | 5 | 5 | 5 | 5 | — | 5 | 5 |
| | 0.8 | 3 | 3 | 3 | 5 | 5 | — | 5 | 5 |
| 245 | 5 | 5 | 5 | 5 | 5 | 5 | — | 5 | 5 |
| | 0.8 | 2 | 3 | 2 | 5 | 5 | — | 5 | 5 |
| 246 | 5 | 4 | 4 | 4 | 5 | 5 | — | 5 | 5 |
| | 0.8 | 2 | 2 | 2 | 5 | 4 | — | 4 | 4 |
| 247 | 5 | 4 | 5 | 4 | 5 | 5 | — | 5 | 5 |
| | 0.8 | 2 | 5 | 3 | 5 | 5 | — | 5 | 4 |
| 248 | 5 | 5 | 5 | 5 | 5 | 5 | — | 5 | 5 |
| | 0.8 | 2 | 5 | 4 | 5 | 5 | — | 5 | 5 |
| 249 | 5 | 4 | 5 | 5 | 5 | 5 | — | 5 | 5 |
| | 0.8 | 2 | 5 | 4 | 5 | 5 | — | 5 | 5 |
| 250 | 0.8 | 3 | 5 | 5 | 5 | 5 | — | 5 | 5 |
| 251 | 5 | 5 | 5 | 5 | 5 | 5 | — | 5 | 5 |
| | 0.8 | 3 | 3 | 5 | 5 | 5 | — | 5 | 5 |
| 252 | 5 | 5 | 5 | 5 | 5 | 5 | — | 5 | 5 |
| | 0.8 | 3 | 5 | 5 | 5 | 5 | — | 5 | 5 |
| 253 | 0.8 | 5 | 5 | 4 | 5 | 5 | — | 5 | 5 |
| | 0.1 | 3 | 4 | 3 | 5 | 5 | — | 5 | 5 |
| 254 | 5 | 5 | 5 | 5 | 5 | 5 | — | 5 | 5 |
| | 0.8 | 3 | 5 | 5 | 5 | 5 | — | 5 | 5 |
| 255 | 0.8 | 5 | 5 | 5 | 5 | 5 | — | 5 | 5 |
| | 0.2 | 3 | 5 | 5 | 5 | 5 | — | 5 | 5 |
| 256 | 0.2 | 5 | 5 | 5 | 5 | 5 | — | 5 | 5 |
| | 0.1 | 4 | 4 | 4 | 5 | 5 | — | 5 | 5 |
| 257 | 0.2 | 5 | 5 | 5 | 5 | 5 | — | 5 | 5 |
| | 0.1 | 4 | 5 | 4 | 5 | 5 | — | 5 | 5 |
| 258 | 0.2 | 5 | 5 | 5 | 5 | 5 | — | 5 | 5 |
| | 0.1 | 4 | 4 | 4 | 5 | 5 | — | 5 | 5 |
| 259 | 0.8 | 3 | 5 | 5 | 5 | 5 | — | 5 | 5 |
| | 0.2 | 1 | 3 | 3 | 5 | 5 | — | 5 | 5 |
| 260 | 0.8 | 4 | 5 | 5 | 5 | 5 | — | 5 | 5 |
| | 0.2 | 2 | 4 | 4 | 5 | 5 | — | 5 | 5 |
| 261 | 0.8 | 4 | 5 | 5 | 5 | 5 | — | 5 | 5 |
| | 0.2 | 2 | 5 | 4 | 5 | 5 | — | 5 | 5 |
| 262 | 0.8 | 4 | 5 | 5 | 5 | 5 | — | 5 | 5 |
| | 0.2 | 2 | 4 | 3 | 5 | 5 | — | 5 | 5 |
| 263 | 0.8 | 4 | 5 | 5 | 5 | 5 | — | 5 | 5 |
| | 0.2 | 2 | 5 | 4 | 5 | 5 | — | 5 | 5 |
| 264 | 0.8 | 4 | 5 | 5 | 5 | 5 | — | 5 | 5 |
| | 0.2 | 2 | 5 | 3 | 5 | 5 | — | 5 | 5 |
| 265 | 0.8 | 4 | 5 | 5 | 5 | 5 | — | 5 | 5 |
| | 0.2 | 2 | 5 | 3 | 5 | 5 | — | 5 | 5 |
| 266 | 0.8 | 4 | 5 | 5 | 5 | 5 | — | 5 | 5 |
| | 0.2 | 2 | 5 | 3 | 5 | 5 | — | 5 | 5 |
| 267 | 0.8 | 4 | 5 | 5 | 5 | 5 | — | 5 | 5 |
| | 0.2 | 2 | 5 | 4 | 5 | 5 | — | 5 | 5 |
| 268 | 0.8 | 5 | 5 | 5 | 5 | 5 | — | 5 | 5 |
| | 0.2 | 2 | 5 | 4 | 5 | 5 | — | 5 | 5 |
| 269 | 0.8 | 5 | 5 | 5 | 5 | 5 | — | 5 | 5 |
| | 0.2 | 2 | 5 | 4 | 5 | 5 | — | 5 | 5 |
| 270 | 0.8 | 5 | 5 | 5 | 5 | 5 | — | 5 | 5 |
| | 0.2 | 3 | 4 | 4 | 5 | 4 | — | 5 | 4 |
| 271 | 0.2 | 5 | 5 | 5 | 5 | 5 | — | 5 | 5 |
| | 0.1 | 4 | 5 | 5 | 5 | 5 | — | 5 | 5 |
| 272 | 0.2 | 5 | 5 | 5 | 5 | 5 | — | 5 | 5 |
| | 0.1 | 4 | 5 | 5 | 5 | 5 | — | 5 | 5 |
| 273 | 0.8 | 5 | 5 | 5 | 5 | 5 | — | 5 | 5 |
| | 0.2 | 3 | 3 | 5 | 5 | 5 | — | 5 | 5 |

TABLE 8-continued

| Com'd. No. | Amount of active ingredient Kg/ha | Phytotoxicity | | post-emergence treatment | | | | | |
|---|---|---|---|---|---|---|---|---|---|
| | | wheat | soybean | barnyard grass | velvetleaf | cocklebur | jimson-weed | birdseye speedwell | cleavers |
| 274 | 0.2 | 5 | 5 | 5 | 5 | 5 | — | 5 | 5 |
| | 0.1 | 4 | 5 | 5 | 5 | 5 | — | 5 | 5 |
| 275 | 0.2 | 5 | 5 | 5 | 5 | 5 | — | 5 | 5 |
| | 0.1 | 3 | 4 | 3 | 5 | 5 | — | 5 | 5 |
| 276 | 0.8 | 5 | 5 | 4 | 5 | 5 | — | 5 | 5 |
| | 0.2 | 3 | 3 | 2 | 5 | 5 | — | 5 | 4 |
| 277 | 5 | 5 | 5 | 5 | 5 | 5 | — | 5 | 5 |
| | 0.8 | 3 | 5 | 4 | 5 | 5 | — | 5 | 5 |
| 278 | 5 | 5 | 5 | 5 | 5 | 5 | — | 5 | 5 |
| | 0.8 | 3 | 5 | 4 | 5 | 5 | — | 5 | 5 |
| 279 | 5 | 5 | 5 | 5 | 5 | 5 | — | 5 | 5 |
| | 0.8 | 3 | 5 | 3 | 5 | 5 | — | 5 | 5 |
| 280 | 5 | 5 | 5 | 5 | 5 | 5 | — | 5 | 5 |
| | 0.8 | 2 | 3 | 3 | 5 | 5 | — | 5 | 5 |
| 281 | 5 | 5 | 5 | 5 | 5 | 5 | — | 5 | 5 |
| | 0.8 | 2 | 5 | 4 | 5 | 5 | — | 5 | 5 |
| 282 | 5 | 5 | 5 | 5 | 5 | 5 | — | 5 | 5 |
| | 0.8 | 2 | 5 | 4 | 5 | 5 | — | 5 | 5 |
| 283 | 5 | 5 | 5 | 5 | 5 | 5 | — | 5 | 5 |
| | 0.8 | 2 | 5 | 4 | 5 | 5 | — | 5 | 5 |
| 284 | 5 | 5 | 5 | 5 | 5 | 5 | — | 5 | 5 |
| | 0.8 | 2 | 5 | 3 | 5 | 5 | — | 5 | 5 |
| 285 | 5 | 5 | 5 | 5 | 5 | 5 | — | 5 | 5 |
| | 0.8 | 2 | 5 | 4 | 5 | 5 | — | 5 | 5 |
| 286 | 5 | 5 | 5 | 5 | 5 | 5 | — | 5 | 5 |
| | 0.8 | 2 | 3 | 2 | 5 | 5 | — | 5 | 5 |
| 287 | 5 | 5 | 5 | 5 | 5 | 5 | — | 5 | 5 |
| | 0.8 | 3 | 5 | 4 | 5 | 5 | — | 5 | 5 |
| 288 | 5 | 5 | 5 | 5 | 5 | 5 | — | 5 | 5 |
| | 0.8 | 3 | 5 | 4 | 5 | 5 | — | 5 | 5 |
| 289 | 5 | 5 | 5 | 5 | 5 | 5 | — | 5 | 5 |
| | 0.8 | 2 | 5 | 4 | 5 | 5 | — | 5 | 5 |
| 290 | 5 | 5 | 5 | 5 | 5 | 5 | — | 5 | 5 |
| | 0.8 | 2 | 5 | 4 | 5 | 5 | — | 5 | 5 |
| 291 | 5 | 5 | 5 | 4 | 5 | 5 | — | 5 | 5 |
| | 0.8 | 2 | 5 | 3 | 5 | 5 | — | 5 | 5 |
| 292 | 5 | 5 | 5 | 5 | 5 | 5 | — | 5 | 5 |
| | 0.8 | 2 | 5 | 4 | 5 | 5 | — | 5 | 5 |
| 293 | 5 | 5 | 5 | 5 | 5 | 5 | — | 5 | 5 |
| | 0.8 | 2 | 5 | 4 | 5 | 5 | — | 5 | 5 |
| 294 | 5 | 5 | 5 | 5 | 5 | 5 | — | 5 | 5 |
| | 0.8 | 2 | 5 | 4 | 5 | 5 | — | 5 | 5 |
| 295 | 5 | 5 | 5 | 4 | 5 | 5 | — | 5 | 5 |
| | 0.8 | 2 | 5 | 3 | 5 | 5 | — | 5 | 5 |
| 296 | 0.8 | 4 | 5 | 4 | 5 | 5 | — | 5 | 5 |
| | 0.2 | 3 | 3 | 3 | 5 | 5 | — | 5 | 5 |
| 297 | 5 | 5 | 5 | 5 | 5 | 5 | — | 5 | 5 |
| | 0.8 | 2 | 4 | 3 | 5 | 5 | — | 5 | 5 |
| 298 | 5 | 5 | 5 | 5 | 5 | 5 | — | 5 | 5 |
| | 0.8 | 3 | 3 | 3 | 5 | 5 | — | 5 | 5 |
| 299 | 5 | 5 | 5 | 5 | 5 | 5 | — | 5 | 5 |
| | 0.8 | 2 | 5 | 4 | 5 | 5 | — | 5 | 5 |
| 300 | 5 | 5 | 5 | 5 | 5 | 5 | — | 5 | 5 |
| | 0.8 | 2 | 5 | 3 | 5 | 5 | — | 5 | 5 |
| 301 | 5 | 5 | 5 | 5 | 5 | 5 | — | 5 | 5 |
| | 0.8 | 3 | 4 | 3 | 5 | 5 | — | 5 | 5 |
| 302 | 5 | 5 | 5 | 5 | 5 | 5 | — | 5 | 5 |
| | 0.8 | 3 | 5 | 3 | 5 | 5 | — | 5 | 5 |
| 303 | 5 | 5 | 5 | 5 | 5 | 5 | — | 5 | 5 |
| | 0.8 | 3 | 5 | 4 | 5 | 5 | — | 5 | 5 |
| 304 | 5 | 5 | 5 | 5 | 5 | 5 | — | 5 | 5 |
| | 0.8 | 3 | 5 | 4 | 5 | 5 | — | 5 | 5 |
| 305 | 5 | 5 | 5 | 5 | 5 | 5 | — | 5 | 5 |
| | 0.8 | 2 | 5 | 3 | 5 | 5 | — | 5 | 5 |
| 306 | 5 | 5 | 5 | 5 | 5 | 5 | — | 5 | 5 |
| | 0.8 | 3 | 5 | 4 | 5 | 5 | — | 5 | 5 |
| 307 | 5 | 5 | 5 | 5 | 5 | 5 | — | 5 | 5 |
| | 0.8 | 2 | 5 | 3 | 5 | 5 | — | 5 | 5 |
| 308 | 5 | 5 | 5 | 5 | 5 | 5 | — | 5 | 5 |
| | 0.8 | 3 | 5 | 4 | 5 | 5 | — | 5 | 5 |
| 309 | 5 | 5 | 5 | 5 | 5 | 5 | — | 5 | 5 |
| | 0.8 | 3 | 5 | 4 | 5 | 5 | — | 5 | 5 |
| 310 | 5 | 5 | 5 | 5 | 5 | 5 | — | 5 | 5 |
| | 0.8 | 2 | 5 | 3 | 5 | 5 | — | 5 | 5 |
| 311 | 5 | 5 | 5 | 5 | 5 | 5 | — | 5 | 5 |
| | 0.8 | 3 | 5 | 4 | 5 | 5 | — | 5 | 5 |
| 312 | 5 | 5 | 5 | 5 | 5 | 5 | — | 5 | 5 |

TABLE 8-continued

| Com'd. No. | Amount of active ingredient Kg/ha | Phytotoxicity | | post-emergence treatment | | | | | |
|---|---|---|---|---|---|---|---|---|---|
| | | wheat | soybean | barnyard grass | velvetleaf | cocklebur | jimson-weed | birdseye speedwell | cleavers |
| | 0.8 | 2 | 5 | 3 | 5 | 5 | — | 5 | 5 |
| 313 | 5 | 5 | 5 | 5 | 5 | 5 | — | 5 | 5 |
| | 0.8 | 2 | 5 | 3 | 5 | 5 | — | 5 | 5 |
| 314 | 5 | 5 | 5 | 5 | 5 | 5 | — | 5 | 5 |
| | 0.8 | 3 | 4 | 4 | 5 | 5 | — | 5 | 5 |
| 315 | 5 | 5 | 5 | 5 | 5 | 5 | — | 5 | 5 |
| | 0.8 | 2 | 5 | 4 | 5 | — | — | 5 | 5 |
| 316 | 5 | 5 | 5 | 5 | 5 | 5 | — | 5 | 5 |
| | 0.8 | 3 | 5 | 3 | 5 | — | — | 5 | 5 |
| 317 | 5 | 5 | 5 | 5 | 5 | — | — | 5 | 5 |
| | 0.8 | 3 | 5 | 4 | 5 | — | — | 5 | 5 |
| 318 | 5 | 5 | 5 | 5 | 5 | 5 | — | 5 | 5 |
| | 0.8 | 2 | 3 | 3 | 5 | 5 | — | 5 | 5 |
| 319 | 5 | 5 | 5 | 5 | 5 | 5 | — | 5 | 5 |
| | 0.8 | 3 | 3 | 3 | 5 | 5 | — | 5 | 5 |
| 320 | 5 | 5 | 5 | 5 | 5 | 5 | — | 5 | 5 |
| | 0.8 | 3 | 5 | 4 | 5 | 5 | — | 5 | 5 |
| 321 | 5 | 4 | 5 | 4 | 5 | 5 | — | 5 | 5 |
| | 0.8 | 2 | 3 | 3 | 5 | 5 | — | 5 | 5 |
| 322 | 5 | 5 | 5 | 5 | 5 | 5 | — | 5 | 5 |
| | 0.8 | 3 | 5 | 4 | 5 | 5 | — | 5 | 5 |
| 323 | 0.8 | 5 | 5 | 5 | 5 | 5 | — | 5 | 5 |
| | 0.1 | 4 | 5 | 5 | 5 | 5 | — | 5 | 5 |
| 324 | 0.8 | 5 | 5 | 5 | 5 | 5 | — | 5 | 5 |
| | 0.1 | 4 | 5 | 4 | 5 | 5 | — | 5 | 5 |
| 325 | 0.8 | 5 | 5 | 5 | 5 | 5 | — | 5 | 5 |
| | 0.2 | 3 | 5 | 5 | 5 | 5 | — | 5 | 5 |
| 326 | 0.8 | 5 | 5 | 5 | 5 | 5 | — | 5 | 5 |
| | 0.2 | 4 | 5 | 4 | 5 | 5 | — | 5 | 5 |
| 327 | 0.8 | 5 | 5 | 5 | 5 | 5 | — | 5 | 5 |
| | 0.2 | 4 | 5 | 4 | 5 | 5 | — | 5 | 5 |
| 328 | 5 | 5 | 5 | 5 | 5 | 5 | — | 5 | 5 |
| | 0.8 | 4 | 5 | 5 | 5 | 5 | — | 5 | 5 |
| 329 | 5 | 5 | 5 | 5 | 5 | 5 | — | 5 | 5 |
| | 0.8 | 2 | 3 | 3 | 5 | 5 | — | 5 | 5 |
| 330 | 5 | 4 | 5 | 5 | 5 | 5 | — | 5 | 5 |
| | 0.8 | 1 | 2 | 2 | 5 | 3 | — | 5 | 5 |
| 331 | 5 | 5 | 5 | 5 | 5 | 5 | — | 5 | 5 |
| | 0.8 | 2 | 5 | 4 | 5 | 5 | — | 5 | 5 |
| 332 | 0.8 | 5 | 5 | 5 | 5 | 5 | — | 5 | 5 |
| | 0.2 | 3 | 4 | 3 | 5 | 5 | — | 5 | 5 |
| 333 | 5 | 4 | 5 | 4 | 5 | 5 | — | 5 | 5 |
| | 0.8 | 2 | 4 | 2 | 5 | 5 | — | 5 | 5 |
| 334 | 5 | 4 | 4 | 5 | 5 | 5 | — | 5 | 5 |
| | 0.8 | 2 | 2 | 4 | 5 | 5 | — | 5 | 5 |
| 335 | 5 | 4 | 5 | 5 | 5 | 5 | — | 5 | 5 |
| | 0.8 | 2 | 3 | 3 | 5 | 4 | — | 5 | 5 |
| 336 | 5 | 5 | 5 | 5 | 5 | 5 | — | 5 | 5 |
| | 0.8 | 4 | 4 | 4 | 5 | 5 | — | 5 | 5 |
| 337 | 5 | 4 | 5 | 5 | 5 | 5 | — | 5 | 5 |
| | 0.8 | 2 | 4 | 3 | 5 | 5 | — | 5 | — |
| 338 | 5 | 5 | 5 | 5 | 5 | 5 | — | 5 | 5 |
| | 0.8 | 3 | 4 | 4 | 5 | 5 | — | 5 | 5 |
| 339 | 5 | 4 | 4 | 4 | 5 | 5 | — | 5 | 5 |
| | 0.8 | 2 | 2 | 2 | 5 | 5 | — | 5 | 5 |
| 340 | 5 | 4 | 5 | 5 | 5 | 5 | — | 5 | 5 |
| | 0.8 | 2 | 3 | 3 | 5 | 5 | — | 5 | 5 |
| 341 | 0.8 | 3 | 3 | 3 | 5 | 5 | — | 5 | 5 |
| | 0.2 | 1 | 1 | 2 | 5 | 4 | — | 5 | 4 |
| 342 | 0.2 | 5 | 5 | 5 | 5 | 5 | — | 5 | 5 |
| | 0.1 | 3 | 5 | 3 | 5 | 5 | — | 5 | 5 |
| 343 | 0.2 | 5 | 5 | 5 | 5 | 5 | — | 5 | 5 |
| | 0.1 | 3 | 4 | 3 | 5 | 5 | — | 5 | 4 |
| 344 | 0.2 | 5 | 5 | 5 | 5 | 5 | — | 5 | 5 |
| | 0.1 | 4 | 5 | 4 | 5 | 5 | — | 5 | 5 |
| 345 | 0.2 | 5 | 5 | 5 | 5 | 5 | — | 5 | 5 |
| | 0.1 | 3 | 5 | 4 | 5 | 5 | — | 5 | 5 |
| 346 | 0.2 | 5 | 5 | 5 | 5 | 5 | — | 5 | 5 |
| | 0.1 | 4 | 5 | 4 | 5 | 5 | — | 5 | 5 |
| 347 | 0.2 | 5 | 5 | 5 | 5 | 5 | — | 5 | 5 |
| | 0.1 | 4 | 5 | 4 | 5 | 5 | — | 5 | 5 |
| 348 | 0.8 | 4 | 5 | 4 | 5 | 5 | — | 5 | 5 |
| | 0.2 | 2 | 3 | 3 | 5 | 5 | — | 5 | 5 |
| 349 | 0.8 | 5 | 5 | 5 | 5 | 5 | — | 5 | 5 |
| | 0.2 | 4 | 5 | 4 | 5 | 5 | — | 5 | 5 |
| 350 | 0.8 | 5 | 5 | 5 | 5 | 5 | — | 5 | 5 |
| | 0.2 | 4 | 5 | 3 | 5 | 5 | — | 5 | 5 |

TABLE 8-continued

| Com'd. No. | Amount of active ingredient Kg/ha | Phytotoxicity | | post-emergence treatment | | | | | |
|---|---|---|---|---|---|---|---|---|---|
| | | wheat | soybean | barnyard grass | velvetleaf | cocklebur | jimson-weed | birdseye speedwell | cleavers |
| 351 | 0.2 | 5 | 5 | 5 | 5 | 5 | — | 5 | 5 |
| | 0.1 | 4 | 5 | 4 | 5 | 5 | — | 5 | 5 |
| 352 | 0.8 | 5 | 5 | 5 | 5 | 5 | — | 5 | 5 |
| | 0.2 | 3 | 5 | 5 | 5 | 5 | — | 5 | 5 |
| 353 | 0.2 | 5 | 5 | 5 | 5 | 5 | — | 5 | 5 |
| | 0.1 | 4 | 5 | 5 | 5 | 5 | — | 5 | 5 |
| 354 | 0.8 | 5 | 5 | 5 | 5 | 5 | — | 5 | 5 |
| | 0.2 | 3 | 5 | 3 | 5 | 5 | — | 5 | 5 |
| 355 | 0.8 | 5 | 5 | 5 | 5 | 5 | — | 5 | 5 |
| | 0.2 | 3 | 5 | 4 | 5 | 5 | — | 5 | 5 |
| 356 | 0.8 | 5 | 5 | 5 | 5 | 5 | — | 5 | 5 |
| | 0.2 | 3 | 5 | 4 | 5 | 5 | — | 5 | 5 |
| 357 | 0.8 | 4 | 5 | 4 | 5 | 5 | — | 5 | 5 |
| | 0.2 | 2 | 3 | 2 | 5 | 4 | — | 5 | 5 |
| 358 | 0.8 | 4 | 4 | 5 | 5 | 5 | — | 5 | 5 |
| | 0.2 | 2 | 2 | 3 | 5 | 5 | — | 5 | 5 |
| 359 | 0.8 | 5 | 5 | 5 | 5 | 5 | — | 5 | 5 |
| | 0.2 | 3 | 5 | 5 | 5 | 5 | — | 5 | 5 |
| 360 | 0.2 | 5 | 5 | 5 | 5 | 5 | — | 5 | 5 |
| | 0.1 | 4 | 5 | 4 | 5 | 5 | — | 5 | 5 |
| 361 | 0.2 | 5 | 5 | 5 | 5 | 5 | — | 5 | 5 |
| | 0.1 | 4 | 5 | 4 | 5 | 5 | — | 5 | 5 |
| 362 | 0.2 | 5 | 5 | 5 | 5 | 5 | — | 5 | 5 |
| | 0.1 | 4 | 4 | 4 | 5 | 5 | — | 5 | 5 |
| 363 | 0.8 | 5 | 5 | 5 | 5 | 5 | — | 5 | 5 |
| | 0.2 | 3 | 5 | 4 | 5 | 5 | — | 5 | 5 |
| 364 | 0.2 | 5 | 5 | 5 | 5 | 5 | — | 5 | 5 |
| | 0.1 | 4 | 5 | 4 | 5 | 5 | — | 5 | 5 |
| 365 | 0.8 | 5 | 5 | 5 | 5 | 5 | — | 5 | 5 |
| | 0.2 | 3 | 5 | 5 | 5 | 5 | — | 5 | 5 |
| 366 | 0.8 | 4 | 5 | 5 | 5 | 5 | — | 5 | 5 |
| | 0.2 | 2 | 4 | 3 | 5 | 4 | — | — | 5 |
| 367 | 0.8 | 4 | 5 | 5 | 5 | 5 | — | 5 | 5 |
| | 0.2 | 2 | 5 | 3 | 5 | 5 | — | 5 | 5 |
| 368 | 0.8 | 5 | 5 | 4 | 5 | 5 | — | 5 | 5 |
| | 0.1 | 4 | 4 | 3 | 5 | 5 | — | 5 | 5 |
| 369 | 0.2 | 5 | 5 | 5 | 5 | 5 | — | 5 | 5 |
| | 0.1 | 4 | 5 | 4 | 5 | 5 | — | 5 | 5 |
| 370 | 0.8 | 4 | 5 | 5 | 5 | 5 | — | 5 | 5 |
| | 0.2 | 2 | 5 | 4 | 5 | 5 | — | 5 | 4 |
| 371 | 0.2 | 5 | 5 | 5 | 5 | 5 | — | 5 | 5 |
| | 0.1 | 4 | 5 | 5 | 5 | 5 | — | 5 | 5 |
| 372 | 0.2 | 5 | 5 | 5 | 5 | 5 | — | 5 | 5 |
| | 0.1 | 4 | 5 | 5 | 5 | 5 | — | 5 | 5 |
| 373 | 0.8 | 5 | 5 | 5 | 5 | 5 | — | 5 | 5 |
| | 0.2 | 4 | 5 | 4 | 5 | 5 | — | 5 | 5 |
| 374 | 0.2 | 5 | 5 | 5 | 5 | 5 | — | 5 | 5 |
| | 0.1 | 4 | 5 | 4 | 5 | 5 | — | 5 | 5 |
| 375 | 0.2 | 5 | 5 | 5 | 5 | 5 | — | 5 | 5 |
| | 0.1 | 4 | 5 | 4 | 5 | 5 | — | 5 | 5 |
| 376 | 0.2 | 5 | 5 | 5 | 5 | 5 | — | 5 | 5 |
| | 0.1 | 4 | 5 | 4 | 5 | 5 | — | 5 | 5 |
| 377 | 0.2 | 5 | 5 | 5 | 5 | 5 | — | 5 | 5 |
| | 0.1 | 4 | 5 | 5 | 5 | 5 | — | 5 | 5 |
| 378 | 5 | 4 | 4 | 4 | 5 | 5 | — | 5 | 5 |
| | 0.8 | 2 | 2 | 2 | 5 | 5 | — | 5 | 5 |
| 379 | 5 | 5 | 5 | 5 | 5 | 5 | — | 5 | 5 |
| | 0.8 | 3 | 5 | 3 | 5 | 5 | — | 5 | 5 |
| 380 | 5 | 4 | 5 | 5 | 5 | 5 | — | 5 | 5 |
| | 0.8 | 2 | 5 | 3 | 5 | 5 | — | 5 | 5 |
| 381 | 5 | 4 | 5 | 5 | 5 | 5 | — | 5 | 5 |
| | 0.8 | 2 | 5 | 4 | 5 | 5 | — | 5 | 5 |
| 382 | 5 | 5 | 5 | 5 | 5 | 5 | — | 5 | 5 |
| | 0.8 | 3 | 5 | 5 | 5 | 5 | — | 5 | 5 |
| 383 | 5 | 4 | 5 | 5 | 5 | 5 | — | 5 | 5 |
| | 0.8 | 2 | 5 | 3 | 5 | 5 | — | 5 | 5 |
| 384 | 5 | 5 | 5 | 5 | 5 | 5 | — | 5 | 5 |
| | 0.8 | 2 | 5 | 3 | 5 | 5 | — | 5 | 5 |
| 385 | 5 | 5 | 5 | 5 | 5 | 5 | — | 5 | 5 |
| | 0.8 | 2 | 5 | 4 | 5 | 5 | — | 5 | 5 |
| 386 | 5 | 5 | 5 | 5 | 5 | 5 | — | 5 | 5 |
| | 0.8 | 2 | 5 | 4 | 5 | 5 | — | 5 | 5 |
| 387 | 5 | 5 | 5 | 5 | 5 | 5 | — | 5 | 5 |
| | 0.8 | 3 | 5 | 4 | 5 | 5 | — | 5 | 5 |
| 388 | 0.8 | 5 | 5 | 4 | 5 | 5 | — | 5 | 5 |
| | 0.1 | 4 | 4 | 3 | 5 | 5 | — | 5 | 5 |
| 389 | 0.8 | 5 | 5 | 4 | 5 | 5 | — | 5 | 5 |

TABLE 8-continued

| Com'd. No. | Amount of active ingredient Kg/ha | Phytotoxicity wheat | Phytotoxicity soybean | post-emergence treatment barnyard grass | velvetleaf | cocklebur | jimson-weed | birdseye speedwell | cleavers |
|---|---|---|---|---|---|---|---|---|---|
|  | 0.2 | 4 | 4 | 4 | 5 | 5 | — | 5 | 5 |
| 390 | 0.8 | 5 | 5 | 4 | 5 | 5 | — | 5 | 5 |
|  | 0.1 | 4 | 4 | 3 | 5 | 5 | — | 5 | 5 |
| 391 | 5 | 5 | 5 | 4 | 5 | 5 | — | 5 | 2 |
|  | 0.8 | 3 | 5 | 2 | 5 | 5 | — | 5 | 0 |
| 392 | 5 | 5 | 5 | 5 | 5 | 5 | — | 5 | 5 |
|  | 0.8 | 2 | 5 | 3 | 5 | 5 | — | 5 | 5 |
| 393 | 5 | 5 | 5 | 5 | 5 | 5 | — | 5 | 5 |
|  | 0.8 | 3 | 5 | 4 | 5 | 5 | — | 5 | 5 |
| 394 | 5 | 5 | 5 | 5 | 5 | 5 | — | 5 | 5 |
|  | 0.8 | 3 | 5 | 4 | 5 | 5 | — | 5 | 5 |
| 395 | 5 | 5 | 5 | 5 | 5 | 5 | — | 5 | 5 |
|  | 0.8 | 2 | 5 | 3 | 5 | 5 | — | 5 | 5 |
| 396 | 5 | 4 | 5 | 4 | 5 | 5 | — | 5 | 5 |
|  | 0.8 | 2 | 5 | 2 | 5 | 5 | — | 5 | 5 |
| 397 | 5 | 5 | 5 | 5 | 5 | 5 | — | 5 | 5 |
|  | 0.8 | 3 | 4 | 2 | 5 | 5 | — | 5 | 5 |
| 398 | 5 | 4 | 5 | 4 | 5 | 5 | — | 5 | 5 |
|  | 0.8 | 2 | 5 | 2 | 5 | 5 | — | 5 | 5 |
| 399 | 5 | 5 | 5 | 5 | 5 | 5 | — | 5 | 5 |
|  | 0.8 | 2 | 5 | 3 | 5 | 5 | — | 5 | 5 |
| 400 | 0.8 | 5 | 5 | 4 | 5 | 5 | — | 5 | 5 |
|  | 0.2 | 4 | 5 | 4 | 5 | 5 | — | 5 | 5 |
| 401 | 5 | 5 | 5 | 5 | 5 | 5 | — | 5 | 5 |
|  | 0.8 | 2 | 5 | 4 | 5 | 5 | — | 5 | 5 |
| 402 | 5 | 5 | 5 | 5 | 5 | 5 | — | 5 | 5 |
|  | 0.8 | 2 | 5 | 4 | 5 | 5 | — | 5 | 5 |
| 403 | 0.8 | 5 | 5 | 4 | 5 | 5 | — | 5 | 5 |
|  | 0.2 | 4 | 5 | 3 | 5 | 5 | — | 5 | 5 |
| 404 | 5 | 5 | 5 | 4 | 5 | 5 | — | 5 | 5 |
|  | 0.8 | 3 | 4 | 3 | 5 | 5 | — | 5 | 5 |
| 405 | 5 | 5 | 5 | 4 | 5 | 5 | — | 5 | 5 |
|  | 0.8 | 3 | 4 | 3 | 5 | 5 | — | 5 | 5 |
| 406 | 5 | 5 | 5 | 4 | 5 | 5 | — | 5 | 5 |
|  | 0.8 | 3 | 4 | 3 | 5 | 4 | — | 5 | 5 |
| A | 5 | 0 | 2 | 0 | 3 | 1 | 2 | — | 3 |
| B | 5 | 0 | 1 | 0 | 2 | 0 | 3 | — | 2 |
| C | 5 | 0 | 1 | 0 | 1 | 0 | 1 | — | 1 |
| D | 5 | 0 | 2 | 2 | 3 | 1 | 3 | — | 3 |

As shown in table 8, the present invented 3-(substituted phenyl)pyrazole derivatives or salt thereof, represented by the general formula (I), exhibit more excellent controlling effect on weeds than comparative compound A, B, C or D on post-emergence treatment in upland fields. Even when the invented derivatives exhibit both herbicidal activity on weeds and phytotoxicity on crops at same dosage, by the selection of proper lower dosage, sufficient herbicidal activity is retained and chemical injury on crops is diminished remarkably.

FORMULATION EXAMPLE 1

A wettable powder composition was prepared by uniform mixing and grinding of the following ingredients:

| | |
|---|---|
| Compound No. 1 | 50 parts |
| Clay-white carbon mixture (clay is the major component) | 45 parts |
| Polyoxyethylene nonyphenyl ether | 5 parts |

FORMULATION EXAMPLE 2

A granular composition was prepared by uniform mixing and grinding of the following ingredients, kneading the mixture with a suitable amount of water, and granulating the kneaded mixture.

| | |
|---|---|
| Compound No. 7 | 5 parts |
| Bentonite-clay mixture | 90 parts |
| Calcium ligninsulfonate | 5 parts |

FORMULATION EXAMPLE 3

An emulsifiable concentrate was prepared by uniform mixing of the following ingredients:

| | |
|---|---|
| Compound No. 12 | 50 parts |
| Xylene | 40 parts |
| Mixture of polyoxyethylene nonylphenyl ether and calcium alkylbenzenesulfonate | 10 parts |

FORMULATION EXAMPLE 4

A wettable powder composition was prepared by uniform mixing and grinding of the following ingredients:

| | |
|---|---|
| Compound No. 33 | 50 parts |
| Clay-white carbon mixture (clay is the major component) | 45 parts |
| Polyoxyethylene nonylphenyl ether | 5 parts |

FORMULATION EXAMPLE 5

A granular composition was prepared by uniform mixing and grinding of the following ingredients, kneading the mixture with a suitable amount of water, and granulating the kneaded mixture.

| Compound No. 122 | 5 parts |
| --- | --- |
| Bentonite-clay mixture | 90 parts |
| Calcium ligninsulfonate | 5 parts |

FORMULATION EXAMPLE 6

An emulsifiable concentrate was prepared by uniform mixing the following ingredients:

| Compound No. 381 | 50 parts |
| --- | --- |
| Xylene | 40 parts |
| Mixture of polyoxyethylene nonylphenyl ether and calcium alkylbenzenesulfonate | 10 parts |

What is claimed is:

1. A 3-(substituted phenyl)pyrazole derivative or a salt thereof, the derivative being represented by the formula

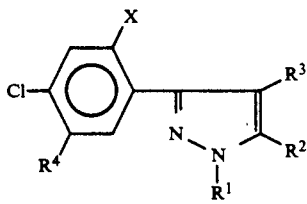

(I)

wherein,

X denotes halogen, $R^1$ denotes lower alkyl or lower haloalkyl, $R^2$ denotes —A—$R^5$ wherein, $R^5$ denotes hydrogen, lower alkyl, or lower haloalkyl and A denotes —O— or —S—, $R^3$ denotes hydrogen or halogen, and $R^4$ denotes (i) formyl, (ii) nitro, (iii) —CO—B—$R^6$ wherein; B denotes —O—, —S—, or —NR$^7$; $R^6$ and $R^7$ are the same or different and each denote hydrogen, lower alkyl, lower alkenyl, lower alkynyl, lower alkoxycarbonylalkyl, cycloalkyl, lower alkylsulfonyl, lower alkoxyalkyl, or di(lower alkoxy)phosphinylalkyl and when B is —O—, $R^6$ can be an alkali metal atom or a quaternary ammonium salt, (iv) —D—$R^8$ wherein, D denotes —O—, —S-(O)$_n$, n being an integer of 0 to 2, or —NR$^9$— and $R^8$ and $R^9$ is the same or different and each denote; hydrogen; alkyl; haloalkyl; lower alkenyl; lower haloalkenyl; lower alkynyl; lower cyanoalkyl; lower cycloalkyl; lower alkoxyalkyl; lower alkylthioalkyl; lower alkoxyalkoxyalkyl; lower alkylsulfonyl; di(lower alkyl)aminosulfonyl; aminosulfonyl having one or more substituents which are the same or different and selected from hydrogen, lower alkynyl, and lower alkyl; phenylalkyl or phenoxyalkyl optionally having, on the phenyl ring, one or more substituents which are the same or different and selected from halogen, lower alkyl, lower haloalkyl, and lower alkoxy; tri(lower alkyl)silylalkyl; or di(lower alkoxy)phosphinylalkyl; or (V)—(CHR$^{10}$)$_m$—CO—E—$R^{12}$ wherein, E denotes —O—, —S—, or —NR$^{11}$ wherein $R^{11}$ is as defined below, $R^{10}$ denotes hydrogen or lower alkyl, and $R^{11}$ and $R^{12}$ are the same or different and each denote; hydrogen; alkyl; haloalkyl; lower alkenyl; lower haloalkenyl; lower alkynyl; lower haloalkynyl; lower alkoxyalkyl; lower cycloalkyl; lower cyanoalkyl; lower alkylthioalkyl; lower alkoxyalkoxyalkoxy; tri(lower alkyl)silylalkyl; di(lower alkoxy)phosphinylalkyl; phenyl optionally having, on the phenyl ring, one or more substituents selected from halogen, lower alkyl, lower haloalkyl, and lower alkoxy; or phenylalkyl optionally having, on the phenyl ring, one or more substituents selected from halogen, lower alkyl, lower haloalkyl, and lower alkoxy; or $R^{11}$, jointly with $R^{12}$, forms piperidino or morpholino, and when E is —O—, $R^{12}$ can be an alkali metal atom or a quaternary ammonium salt; and m denote an integer of 0 to 3.

2. A 3-(substituted phenyl)pyrazole derivative or a salt thereof according to claim 1, wherein; X denotes halogen; $R^1$ denotes lower alkyl; $R^2$ denotes —A—$R^5$ wherein, $R^5$ denotes lower alkyl or lower haloalkyl and A denotes —O— or —S—; $R^3$ denotes halogen; and $R^4$ denotes (i)—CO—B—$R^6$ wherein, B denotes —O—, —S—, or —NR$^7$ and $R^6$ and $R^7$ are the same or different and each denote hydrogen, lower alkyl, lower alkenyl, lower alkynyl, or lower alkoxycarbonylalkyl, (ii) —D—$R^8$ wherein, D denotes —O—, —S—, or —NR$^9$— and $R^8$ and $R^9$ are the same or different and each denote; lower alkyl; lower haloalkyl; lower alkenyl; lower haloalkenyl; lower alkynyl; lower cyanoalkyl; lower cycloalkyl lower alkoxyalkyl; lower alkylsulfonyl; or aminosulfonyl having one or more substituents which are the same or different and selected from hydrogen and lower alkyl; or (iii) —CHR$^{10}$—CO—E—$R^{12}$ wherein, E denotes —O—, —S—, or —NR$^{11}$, $R^{11}$ being as defined below; $R^{10}$ denotes hydrogen or lower alkyl, and $R^{11}$ and $R^{12}$ are the same or different and each denote lower alkyl, lower haloalkyl, lower alkenyl, lower haloalkenyl, lower alkynyl; lower haloalkynyl, lower alkoxyalkyl, lower cycloalkyl, lower alkoxyalkoxyalkoxy, or tri(lower alkyl)silylalkyl.

3. A 3-(substituted phenyl)pyrazole derivative or a salt thereof according to claim 2, wherein; X denotes halogen; $R^1$ denotes lower alkyl; $R^2$ denotes —A—$R^5$ wherein, $R^5$ denotes lower haloalkyl and A denotes —O— or —S—; $R^3$ denotes halogen; and $R^4$ denotes (i) —CO—B—$R^6$ wherein, B denotes —O— or —S— and $R^6$ denotes lower alkyl or lower alkoxycarbonylalkyl, (ii) —D—$R^8$ wherein, B denotes —O—, —S—, or —NR$^9$— and $R^8$ and $R^9$ are the same or different and each denote hydrogen, lower alkenyl or lower alkynyl, or —CHR$^{10}$—CO—E—$R^{12}$ wherein, E denotes —O— or —S—, $R^{10}$ denotes hydrogen or lower alkyl, and $R^{12}$ denotes lower alkyl or lower haloalkyl.

4. A 3-(substituted phenyl)pyrazole derivative or a salt thereof according to claim 3, wherein; X denotes halogen; $R^1$ denotes methyl; $R^2$ denotes difluoromethoxy; $R^3$ denotes halogen; and $R^4$ denotes (i) —CO—B—$R^6$ wherein, $R^6$ denotes lower alkyl or lower alkoxycarbonylalkyl and B denotes —O— or —S—, (ii) —D—$R^8$ wherein, D denotes —O—, —S— or —NR$^9$— and $R^8$ and $R^9$ are the same or different and each denotes hydrogen, lower alkenyl, or lower alkynyl, or (iii) —CHR$^{10}$—CO—E—$R^{12}$ wherein, E denotes —O— or —S—, $R^{10}$ denotes hydrogen or lower alkyl, and $R^{12}$ denotes lower alkyl or lower haloalkyl.

5. A 3-(substituted phenyl)pyrazole derivative or a salt thereof according to claim 4, which derivative is methyl 5-(4-chloro-5-difluoromethoxy-1-methyl-1H-pyrazol-3-yl)-2,4-dichlorobenzoate,
   ethyl 5-(4-chloro-5-difluoromethoxy-1-methyl-1H-pyrazol-3-yl)-2,4-dichlorobenzoate,
   methyl 2-chloro-5-(4-chloro-5-difluoromethoxy-1-methyl-1H-pyrazol-3-yl)-4-fluorobenzoate,
   ethyl 2-chloro-5-(4-chloro-5-difluoromethoxy-1-methyl-1H-pyrazol-3-yl)-4-fluorobenzoate,
   1-(methoxycarbonyl)ethyl 2,4-dichloro-5-(4-chloro-5-difluoromethoxy-1-methyl-1H-pyrazol-3-yl)benzoate,
   1-(ethoxycarbonyl)ethyl 2,4-dichloro-5-(4-chloro-5-difluoromethoxy-1-methyl-1H-pyrazol-3-yl)benzoate,
   1-(methoxycarbonyl)ethyl 2-chloro-5-(4-chloro-5-difluoromethoxy-1-methyl-1H-pyrazol-3-yl)-4-fluorobenzoate,
   1-(ethoxycarbonyl)ethyl 2-chloro-5-(4-chloro-5-difluoromethoxy-1-methyl-1H-pyrazol-3-yl)-4fluorobenzoate,
   4-chloro-3-[2,4-dichloro-5-(2-propenyloxy)phenyl]-5-difluoromethoxy-1-methyl-1H-pyrazole,
   4-chloro-3-[2,4-dichloro-5-(2-propynyloxy)phenyl]-5-difluoromethoxy-1-methyl-1H-pyrazole,
   4-chloro-3-[4-chloro-2-fluoro-5-(2-propenyloxy)-phenyl]-5-difluoromethoxy-1-methyl-1H-pyrazole,
   4-chloro-3-[4-chloro-2-fluoro-5-(2-propynyloxy)-phenyl]-5-difluoromethoxy-1-methyl-1H-pyrazole,
   4-chloro-3-[4-chloro-2-fluoro-5-(2-propenylthio)-phenyl]-5-difluoromethoxy-1-methyl-1H-pyrazole,
   4-chloro-3-[4-chloro-2-fluoro-5-(2-propynylthio)-phenyl]-5-difluoromethoxy-1-methyl-1H-pyrazole,
   4-chloro-3-[4-chloro-2-fluoro-5-(2-propenylamino)-phenyl]-5-difluoromethoxy-1-methyl-1H-pyrazole,
   4-chloro-3-[4-chloro-2-fluoro-5-(2-propynylamino)-phenyl]-5-difluoromethoxy-1-methyl-1H-pyrazole,
   methyl 5-(4-chloro-5-difluoromethoxy-1-methyl-1H-pyrazol-3-yl)-2,4-dichlorophenoxyacetate,
   ethyl 5-(4-chloro-5-difluoromethoxy-1-methyl-1H-pyrazol-3-yl)-2,4-dichlorophenoxyacetate,
   n-propyl 5-(4-chloro-5-difluoromethoxy-1-methyl-1H-pyrazol-3-yl)-2,4-dichlorophenoxyacetate,
   isopropyl 5-(4-chloro-5-difluoromethoxy-1-methyl-1H-pyrazol-3-yl)-2,4-dichlorophenoxyacetate,
   methyl 2-chloro-5-(4-chloro-5-difluoromethoxy-1-methyl-1H-pyrazol-3-yl)-4-fluorophenoxy acetate,
   ethyl 2-chloro-5-(4-chloro-5-difluoromethoxy-1-methyl-1H-pyrazol-3-yl)-4-fluorophenoxyacetate,
   n-propyl 2-chloro-5-(4-chloro-5-difluoromethoxy-1-methyl-1H-pyrazol-3-yl)-4-fluorophenoxy acetate,
   isopropyl 2-chloro-5-(4-chloro-5-difluoromethoxy-1-methyl-1H-pyrazol-3-yl)-4-fluorophenoxyacetate,
   methyl 5-(4-chloro-5-difluoromethoxy-1-methyl-1H-pyrazol-3-yl)-2,4-dichlorophenylthioacetate,
   ethyl 5-(4-chloro-5-difluoromethoxy-1-methyl-1H-pyrazol-3-yl)-2,4-dichlorophenylthioacetate,
   methyl 2-chloro-5-(4-chloro-5-difluoromethoxy-1-methyl-1H-pyrazol-3-yl)-4-fluorophenylthioacetate,
   ethyl 2-chloro-5-(4-chloro-5-difluoromethoxy-1-methyl-1H-pyrazol-3-yl)-4-fluorophenylthioacetate,
   ethyl 2-[5-(4-chloro-5-difluoromethoxy-1-methyl-1H-pyrazol-3-yl)-2,4-dichlorophenoxy)propionate,
   methyl 2-[5-(4-chloro-5-difluoromethoxy-1-methyl-1H-pyrazol-3-yl)-2,4-dichlorophenylthio]propionate,
   ethyl 2-[5-(4-chloro-5-difluoromethoxy-1-methyl-1H-pyrazol-3-yl)-2,4-dichlorophenylthio]propionate,
   methyl 2-[2-chloro-5-(4-chloro-5-difluoromethoxy-1-methyl-1H-pyrazol-3-yl)-4-fluorophenoxy]propionate,
   ethyl 2-[2-chloro-5-(4-chloro-5-difluoromethoxy-1-methyl-1H-pyrazol-3-yl)-4-fluorophenoxy]propionate,
   methyl 2-[2-chloro-5-(4-chloro-5-difluoromethoxy-1-methyl-1H-pyrazol-3-yl)-4-fluorophenylthio]propionate, or
   ethyl 2-[2-chloro-5-(4-chloro-5-difluoromethoxy-1-methyl-1H-pyrazol-3-yl)-4-fluorophenylthio]propionate.

6. A herbicidal composition which contains an agriculturally and horticulturally acceptable carrier and an effective amount of 3-(substituted phenyl)pyrazole derivative or a salt thereof as an active ingredient, the pyrazole derivative being represented by the formula

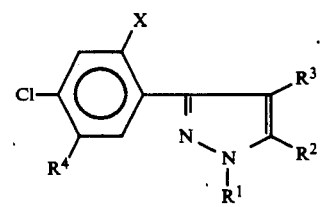

wherein,
X denotes halogen,
$R^1$ denotes lower alkyl or lower haloalkyl,
$R^2$ denotes —A—$R^5$ wherein, $R^5$ denotes hydrogen, lower alkyl, or lower haloalkyl and A denotes —O— or —S—,
$R^3$ denotes hydrogen or halogen, and
$R^4$ denotes (i) formyl, (ii) nitro, (iii) —CO—B—$R^6$ wherein; B denotes —O—, —S—, or —NR$^7$; $R^6$ and $R^7$ are the same or different and each denote hydrogen, lower alkyl, lower alkenyl, lower alkynyl, lower alkoxycarbonylalkyl, cycloalkyl, lower alkylsulfonyl, lower alkoxyalkyl, or di(lower alkoxy)phosphinylalkyl and when B is —O—, $R^6$ can be an alkali metal atom or a quaternary ammonium salt, (iv) —D—$R^8$ wherein, D denotes —O—, —S-(O)$_n$, n being an integer of 0 to 2, or —NR$^9$— and $R^8$ and $R^9$ is the same or different and each denote; hydrogen; alkyl; haloalkyl; lower alkenyl; lower haloalkenyl; lower alkynyl; lower cyanoalkyl; lower cycloalkyl; lower alkoxyalkyl; lower alkylthioalkyl; lower alkoxyalkoxyalkyl; lower alkylsulfonyl; di(lower alkyl)aminosulfonyl; aminosulfonyl having one or more substituents which are the same or different and selected from hydrogen, lower alkynyl, and lower alkyl; phenylalkyl or phenoxyalkyl optionally having, on the phenyl ring, one or more substituents which are the same or different and selected from halogen, lower alkyl, lower haloalkyl, and lower alkoxy; tri(lower alkyl)silylalkyl; or di(lower alkoxy)phosphinylalkyl; or (v) —(CHR$^{10}$)$_m$—CO—E—R$^{12}$ wherein, E denotes —O—, —S—, or —NR$^{11}$ wherein R$^{11}$ is as defined below, R$^{10}$ denotes hydrogen or lower alkyl, and R$^{11}$ and R$^{12}$ are the same or different and each denote; hydrogen; alkyl; haloalkyl; lower alkenyl; lower haloalkenyl; lower alkynyl; lower haloalkynyl; lower alkoxyalkyl; lower cycloalkyl; lower cyanoalkyl; lower alkylthioalkyl; lower alkoxyalkoxyalkoxy; tri(lower alkyl)silylalkyl; di(lower alkoxy)phosphinylalkyl; phenyl optionally having, on the phenyl ring, one or more substituents selected from halogen, lower alkyl, lower haloalkyl, and lower alkoxy; or phenylalkyl optionally having, on the phenyl ring, one or more substituents selected from halogen, lower alkyl, lower haloalkyl, and lower alkoxy; or $R^{11}$, jointly with $R^{12}$, forms piperidino or morpholino, and when E is —O—, $R^{12}$ can be an alkali metal atom or a quaternary ammonium salt; and m denote an integer of 0 to 3.

7. A herbicidal composition according to claim 6, wherein;
X denotes halogen;
$R^1$ denotes lower alkyl; $R^2$ denotes —A—$R^5$ wherein, $R^5$ denotes lower alkyl or lower haloalkyl and A denotes —O— or —S—; $R^3$ denotes halogen; and $R^4$ denotes (i) —CO—B—$R^6$ wherein, B denotes —O—, —S—, or —$NR^7$ and $R^6$ and $R^7$ are the same or different and each denote hydrogen, lower alkyl, lower aLkenyl, lower alkynyl, or lower alkoxycarbonylalkyl, (ii) —D—$R^8$ wherein, D denotes —O—, —S—, or —$NR^9$— and $R^8$ and $R^9$ are the same or different and each denote; lower alkyl; lower haloalkyl; lower alkenyl; lower haloalkenyl; lower alkynyl; lower cyanoalkyl; lower cycloalkyl lower alkoxyalkyl; lower alkylsulfonyl; or aminosulfonyl having one or more substituents which are the same or different and selected from hydrogen and lower alkyl; or (iii) —$CHR^{10}$—CO—E—$R^{12}$ wherein, E denotes —O—, —S—, or —$NR^{11}$—, $R^{11}$ being as defined below, $R^{10}$ denotes hydrogen or lower alkyl, and $R^{11}$ and $R^{12}$ are the same or different and each denote lower alkyl, lower haloalkyl, lower alkenyl, lower haloalkenyl, lower alkynyl, lower haloalkynyl, lower alkoxyalkyl, lower cycloalkyl, lower alkoxyalkoxyalkoxy, or tri(lower alkyl)silylalkyl.

8. A herbicidal composition according to claim 7, wherein; X denotes halogen; $R^1$ denotes lower alkyl; $R^2$ denotes —A—$R^5$ wherein, $R^5$ denotes lower haloalkyl and A denotes —O— or —S—; $R^3$ denotes halogen; and $R^4$ denotes (i) —CO—B—$R^6$ wherein, B denotes —O— or —S— and $R^6$ denotes lower alkyl or lower alkoxycarbonylalkyl, (ii) wherein, —D—$R^8$ wherein, D denotes —O—, —S—, or —$NR^9$— and $R^8$ and $R^9$ are the same or different and each denote hydrogen, lower alkyl, lower alkenyl, or lower alkynyl, or (iii) —$(CHR^{10})_m$—CO—E—$R^{12}$ wherein, E denotes —O— or —S—, $R^{10}$ denotes hydrogen or lower alkyl, $R^{12}$ denotes alkyl or lower haloalkyl, and m denotes 0 or 1.

9. A herbicidal composition according to claim 8, wherein; X denotes halogen; $R^1$ denotes methyl; $R^2$ denotes difluoromethoxy; $R^3$ denotes halogen; and $R^4$ denotes (i) —CO—B—$R^6$ wherein, $R^6$ denotes lower alkyl or lower alkoxycarbonylalkyl and B denotes —O— or —S—, (ii) —D—$R^8$ wherein, D denotes —O—, —S— and —$NR^9$— and $R^8$ and $R^9$ are the same or different and each denote hydrogen, lower alkenyl, or lower alkynyl, or (iii) —$(CHR^{10})_m$—CO—E—$R^{12}$ wherein, E denotes —O— or —S—, $R^{10}$ denotes hydrogen or lower alkyl, $R^{12}$ denotes alkyl or lower haloalkyl, and m denotes 0 or 1.

10. A herbicidal composition according to claim 9, wherein the pyrazole derivative is
methyl 5-(4-chloro-5-difluoromethoxy-1-methyl-1H-pyrazol-3-yl)-2,4-dichlorobenzoate,
ethyl 5-(4-chloro-5-difluoromethoxy-1-methyl-1H-pyrazol-3-yl)-2,4-dichlorobenzoate,
methyl 2-chloro-5-(4-chloro-5-difluoromethoxy-1-methyl-1H-pyrazol-3-yl)-4-fluorobenzoate,
ethyl 2-chloro-5-(4-chloro-5-difluoromethoxy-1-methyl-1H-pyrazol-3-yl)-4-fluorobenzoate,
1-(methoxycarbonyl)ethyl 2,4-dichloro-5-(4-chloro-5-difluoromethoxy-1-methyl-1H-pyrazol-3-yl)benzoate,
1-(ethoxycarbonyl)ethyl 2,4-dichloro-5-(4-chloro-5-difluoromethoxy-1-methyl-1H-pyrazol-3-yl)benzoate,
1-(methoxycarbonyl)ethyl 2-chloro-5-(4-chloro-5-difluoromethoxy-1-methyl-1H-pyrazol-3-yl)-4-fluorobenzoate,
1-(ethoxycarbonyl)ethyl 2-chloro-5-(4-chloro-5-difluoromethoxy-1-methyl-1H-pyrazol-3-yl)-4-fluorobenzoate,
4-chloro-3-[2,4-dichloro-5-(2-propenyloxy)phenyl]-5-difluoromethoxy-1-methyl-1H-pyrazole,
4-chloro-3-[2,4-dichloro-5-(2-propynyloxy)phenyl]-5-difluoromethoxy-1-methyl-1H-pyrazole,
4-chloro-3-[4-chloro-2-fluoro-5-(2propenyloxy)-phenyl]-5-difluoromethoxy-1-methyl-1H-pyrazole,
4-chloro-3-[4-chloro-2-fluoro-5-(2-propynyloxy)-phenyl]-5-difluoromethoxy-1-methyl-1H-pyrazol,
4-chloro-3-[4-chloro-2-fluoro-5-(2-propenylthio)-phenyl]-5-difluoromethoxy-1-methyl-1H-pyrazole,
4-chloro-3-[4-chloro-2-fluoro-5-(2-propynylthio)-phenyl]-5-difluoromethoxy-1-methyl-1H-pyrazol,
4-chloro-3-[4-chloro-2-fluoro-5-(2-propenylamino)-phenyl]-5-difluoromethoxy-1-methyl-1H-pyrazole,
4-chloro-3-[4-chloro-2-fluoro-5-(2-propynylamino)-phenyl]-5-difluoromethoxy-1-methyl-1H-pyrazole,
methyl 5-(4-chloro-5-difluoromethoxy-1-methyl-1H-pyrazol-3-yl)-2,4-dichlorophenoxyacetate,
ethyl 5-(4-chloro-5-difluoromethoxy-1-methyl-1H-pyrazol-3-yl)-2,4-dichlorophenoxyacetate,
n-propyl 5-(4-chloro-5-difluoromethoxy-1-methyl-1H-pyrazol-3-yl)-2,4-dichlorophenoxyacetate,
isopropyl 5-(4-chloro-5-difluoromethoxy-1-methyl-1H-pyrazol-3-yl)-2,4-dichlorophenoxyacetate,
methyl 2-chloro-5-(4-chloro-5-difluoromethoxy-1-methyl-1H-pyrazol-3-yl)-4-fluorophenoxyacetate,
ethyl 2-chloro-5-(4-chloro-5-difluoromethoxy-1-methyl-1H-pyrazol-3-yl)-4-fluorophenoxyacetate,
n-propyl 2-chloro-5-(4-chloro-5-difluoromethoxy-1-methyl-1H-pyrazol-3-yl)-4-fluorophenoxyacetate,
isopropyl 2-chloro-5-(4-chloro-5-difluoromethoxy-1-methyl-1H-pyrazol-3-yl)-4-fluorophenoxyacetate,
methyl 5-(4-chloro-5-difluoromethoxy-1-methyl-1H-pyrazole-3-yl)-2,4-dichlorophenylthioacetate,
ethyl 5-(4-chloro-5-difluoromethoxy-1-methyl-1H-pyrazole-3-yl)-2,4-dichlorophenylthioacetate,
methyl 2-chloro-5-(4-chloro-5-difluoromethoxy-1-methyl-1H-pyrazol-3-yl)-4-fluorophenylthioacetate,
ethyl 2-chloro-5-(4-chloro-5-difluoromethoxy-1-methyl-1H-pyrazol-3-yl)-4-fluorophenylthioacetate,
ethyl 2-[5-(4-chloro-5-difluoromethoxy-1-methyl-4-pyrazol-3-yl)-2,4-dichlorophenoxy]propionate, methyl 2-[5-(4-chloro-5-difluoromethoxy-1-methyl-1H-pyrazol-3-yl)-2,4-dichlorophenylthio]propionate,
ethyl 2-[5-(4-chloro-5-difluoromethoxy-1-methyl-1H-pyrazol-3-yl)-2,4-dichlorophenylthio]propionate,
methyl 2-[2-chloro-5-(4-chloro-5-difluoromethoxy-1-methyl-1H-pyrazol-3-yl)-4-fluorophenoxy]propionate,
ethyl 2-[2-chloro-5-(4-chloro-5-difluoromethoxy-1-methyl-1H-pyrazol-3-yl),-4-fluorophenoxy]propionate,
methyl 2-[2-chloro-5-(4-chloro-5-difluoromethoxy-1-methyl-1H-pyrazol-3-yl)-4-fluorophenylthio]propionate, or
ethyl 2-[2-chloro-5-(4-chloro-5-difluoromethoxy-1-methyl-1H-pyrazol-3-yl)-4-fluorophenylthio]propionate.

11. A herbicidal composition according to claim 10, which is for paddy fields, upland fields, or non-farming areas.

12. A herbicidal composition according to claim 11, which, for paddy field purposes, contains
4-chloro-3-[2,4-dichloro-5-(2-propenyloxy)phenyl]-5-difluoromethoxy-1-methyl-1H-pyrazole,
4-chloro-3-[2,4-dichloro-5-(2-propynyloxy)phenyl]-5-difluoromethoxy-1-methyl-1H-pyrazole,
4-chloro-3-[4-chloro-2-fluoro-5-(2-propenyloxy)-phenyl]-5-difluoromethoxy-1-methyl-1H-pyrazole,
4-chloro-3-[4-chloro-2-fluoro-5-(2-propynyloxy)-phenyl]-5-difluoromethoxy-1-methyl-1H-pyrazole,
4-chloro-3-[4-chloro-2-fluoro-5-(2-propenylthio)-phenyl]-5-difluoromethoxy-1-methyl-1H-pyrazole,
4-chloro-3-[4-chloro-2-fluoro-5-(2-propynylthio)-phenyl]-5-difluoromethoxy-1-methyl-1H-pyrazole,
4-chloro-3-[4-chloro-2-fluoro-5-(2-propenylamino)-phenyl]-5-difluoromethoxy-1-methyl-1H-pyrazole, or
4-chloro-3-[4-chloro-2-fluoro-5-(2-propynylamino)-phenyl]-5-difluoromethoxy-1-methyl-1H-pyrazole.

13. A herbicidal composition according to claim 11, the upland field purpose composition of which is particularly applied to wheat fields.

14. A herbicidal composition according to claim 13, which, for upland field purposes, contains
methyl 5-(4-chloro-5-difluoromethoxy-1-methyl-1H-pyrazole-3-yl)-2,4-dichlorophenoxyacetate,
ethyl 5-(4-chloro-5-difluoromethoxy-1-methyl-1H-pyrazol-3-yl)-2,4-dichlorophenoxyacetate,
n-propyl 5-(4-chloro-5-difluoromethoxy-1-methyl-1H-pyrazol-3-yl)-2,4-dichlorophenoxyacetate,
isopropyl 5-(4-chloro-5-difluoromethoxy-1-methyl-1H-pyrazol-3-yl)-2,4-dichlorophenoxyacetate,
methyl 2-chloro-5-(4-chloro-5-difluoromethoxy-1-methyl-1H-pyrazol-3-yl)-4-fluorophenoxyacetate,
ethyl 2-chloro-5-(4-chloro-5-difluoromethoxy-1-methyl-1H-pyrazol-3-yl)-4-fluorophenoxyacetate,
n-propyl 2-chloro-5-(4-chloro-5-difluoromethoxy-1-methyl-1H-pyrazol-3-yl)-4-fluorophenoxyacetate,
isopropyl 2-chloro-5-(4-chloro-5-difluoromethoxy-1-methyl-1H-pyrazol-3-yl)-4-fluorophenoxyacetate,
methyl 5-(4-chloro-5-difluoromethoxy-1-methyl-1H-pyrazol-3-yl)-2,4-dichlorophenylthioacetate,
ethyl 5-(4-chloro-5-difluoromethoxy-1-methyl-1H-pyrazol-3-yl)-2,4-dichlorophenylthioacetate,
methyl 2-chloro-5-(4-chloro-5-difluoromethoxy-1-methyl-1H-pyrazol-3-yl)-4-fluorophenylthioacetate,
ethyl 2-chloro-5-(4-chloro-5-difluoromethoxy-1-methyl-1H-pyrazol-3-yl)-4-fluorophenylthioacetate.

15. A herbicidal composition according to claim 11, which, for non-farming area purposes, contains
methyl 5-(4-chloro-5-difluoromethoxy-1-methyl-1H-pyrazol-3-yl)-2,4-dichlorobenzoate,
ethyl 5-(4-chloro-5-difluoromethoxy-1-methyl-1H-pyrazol-3-yl)-2,4-dichlorobenzoate,
methyl 2-chloro-5-(4-chloro-5-difluoromethoxy-1-methyl-1H-pyrazol-3-yl)-4-fluorobenzoate,
ethyl 2-chloro-5-(4-chloro-5-difluoromethoxy-1-methyl-1H-pyrazol-3-yl)-4-fluorobenzoate,
1-(methoxycarbonyl)ethyl 5-(4-chloro-5-difluromethoxy-1-methyl-1H-pyrazol-3-yl)-2,4-dichlorobenzoate,
1-(ethoxycarbonyl)ethyl 5-(4-chloro-5-difluoromethoxy-1-methyl-1H-pyrazol-3-yl)-2,4-dichlorobenzoate,
1-(methoxycarbonyl)ethyl 2-chloro-5-(4-chloro-5-difluoromethoxy-1-methyl-1H-pyrazol-3-yl)4-fluorobenzoate,
1-(ethoxycarbonyl)ethyl 2-chloro-5-(4-chloro-5-difluoromethoxy-1-methyl-1H-pyrazol-3-yl)4-fluorobenzoate,
ethyl 2-[5-(4-chloro-5-difluoromethoxy-1-methyl-1H-pyrazol-3-yl)-2,4-dichlorophenoxy]propionate,
methyl 2-[5-(4-chloro-5-difluoromethoxy-1-methyl-1H-pyrazol-3-yl)-2,4-dichlorophenylthio]propionate,
ethyl 2-[5-(4-chloro-5-difluoromethoxy-1-methyl-1H-pyrazol-3-yl)-2,4-dichlorophenylthio]propionate,
methyl 2-[2-chloro-5-(4-chloro-5-difluoromethoxy-1-methyl-1H-pyrazol-3-yl)-4-fluorophenoxy]propionate,
ethyl 2-[2-chloro-5-(4-chloro-5-difluoromethoxy-1-methyl-1H-pyrazol-3-yl)-4-fluorophenoxy]propionate,
methyl 2-[2-chloro-5-(4-chloro-5-difluoromethoxy-1-methyl-1H-pyrazol-3-yl)-4-fluorophenylthio]propionate, or
ethyl 2-[2-chloro-5-(4-chloro-5-difluoromethoxy-1-methyl,-1H-pyrazol-3-yl)-4-fluorophenylthio]propionate.

16. A method for controlling undesirable plants which comprises applying a herbicidal composition containing a 3-(substituted phenyl)pyrazole derivative represented by the following general formula (I) or a salt of the derivative as an active ingredient, in a dose of 1.0 g to 10 Kg in terms of the quantity of active ingredient per hectare,

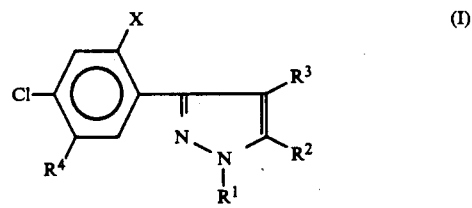

wherein,
X denotes halogen,
$R^1$ denotes lower alkyl or lower haloalkyl,
$R^2$ denotes —A—$R^5$ wherein, $R^5$ denotes hydrogen, lower alkyl, or lower haloalkyl and A denotes —O— or —S—,
$R^3$ denotes hydrogen or halogen, and $R^4$ denotes (i) formyl, (ii) nitro, (iii) —CO—B—$R^6$ wherein; B denotes —O—, —S—, or —$NR^7$; $R^6$ and $R^7$ are the same or different and each denote hydrogen, lower alkyl, lower alkenyl, lower alkynyl, lower alkoxycarbonylalkyl, cycloalkyl, lower alkylsulfonyl, lower alkoxyalkyl, or di(lower alkoxy)phosphinylalkyl and when B is —O—, $R^6$ can be an alkali metal atom or a quaternary ammonium salt, (iv) —D—$R^8$ wherein, D denotes —O—, —S-(O)$_n$, n being an integer of 0 to 2, or —$NR^9$— and $R^8$ and $R^9$ is the same or different and each denote; hydrogen; alkyl; haloalkyl; lower alkenyl; lower haloalkenyl; lower alkynyl; lower cyanoalkyl; lower cycloalkyl; lower alkoxyalkyl; lower alkylthioalkyl; lower alkoxyalkoxyalkyl; lower alkylsulfonyl; di(lower alkyl)aminosulfonyl; aminosulfonyl having one or more substituents which are the same or different and selected from hydrogen, lower alkynyl, and lower alkyl; phenylalkyl or phenoxyalkyl optionally having, on the phenyl ring, one or more substituents which are the same or different and selected from halogen, lower alkyl, lower haloalkyl, and lower alkoxy; tri(lower alkyl)silylalkyl; or di(lower alkoxy)phosphinylalkyl; or (v) —(CHR$^{10}$)$_m$—CO—E—R$^{12}$ wherein, E denotes —O—, —S—, or —NR$^{11}$ wherein R$^{11}$ is as defined below, R$^{10}$ denotes hydrogen or lower alkyl, and R$^{11}$ and R$^{12}$ are the same or different and each denote; hydrogen; alkyl; haloalkyl; lower alkenyl; lower haloalkenyl; lower alkynyl; lower haloalkynyl; lower alkoxyalkyl; lower cycloalkyl; lower cyanoalkyl; lower alkylthioalkyl; lower alkoxyalkoxyalkoxy; tri(lower alkyl)silylalkyl; di(lower alkoxy)phosphinylalkyl; phenyl optionally having, on the phenyl ring, one or more substituents selected from halogen, lower alkyl, lower haloalkyl, and lower alkoxy; or phenylalkyl optionally having, on the phenyl ring, one or more substituents selected from halogen, lower alkyl, lower haloalkyl, and lower alkoxy; or R$^{11}$, jointly with R$^{12}$, forms piperidino or morpholino, and when E is —O—, R$^{12}$ can be an alkali metal atom or a quaternary ammonium salt; and m denote an integer of 0 to 3.

17. The method of claim 16, wherein paddy fields are treated with said herbicidal composition.

18. The method of claim 16, wherein upland fields are treated with said herbicidal composition.

19. The method of claim 18, wherein said upland fields are wheat fields.

20. The method of claim 16, wherein non-farming areas are treated with said herbicidal composition.

* * * * *

UNITED STATES PATENT AND TRADEMARK OFFICE
CERTIFICATE OF CORRECTION

PATENT NO. : 5,032,165
DATED : July 16, 1991
INVENTOR(S) : MIURA et al

It is certified that error appears in the above-indentified patent and that said Letters Patent is hereby corrected as shown below:

Col. 1, line 37, after "salt]," add --or--;
            62, delete "or" (first instance) and delete "]"; and
            63, delete "[" and insert therefore --(--.

Col.111, line 52, after "salt," add --or--;
            67, delete "or"; and
            68, delete "(V)".

Col.112, line 29, after "alkoxycarbonylalkyl," add --or--;
            35, delete "or" (first instance);
            37, delete "(iii)";
            51, after "alkoxycarbonylalkyl," add --or--;
            64, after "-s-," add --or--; and
            67, delete "or" (first instance) and delete "(iii)".

Col.114, line 48, after "salt," add --or--;
            63, delete "or"; and
            64, delete "(V)".

UNITED STATES PATENT AND TRADEMARK OFFICE
CERTIFICATE OF CORRECTION

PATENT NO. : 5,032,165
DATED : July 16, 1991
INVENTOR(S) : MIURA et al

It is certified that error appears in the above-indentified patent and that said Letters Patent is hereby corrected as shown below:

```
Col.115, line 26, after "oxycarbonylalkyl," add --or--;
            31, delete "or";
            34, delete "(iii)";
            50, after "carbonylalkyl," add --or-- and delete
                "wherein," (first instance);
            53, delete "or" (first instance) and delete "(iii)";
            62, after "-s-," add --or--; and
            65, delete "or" (first instance) and delete "(iii)".
Col.119, line  9, after "salt," add --or--;
            24, delete "or"; and
            25, delete "(V)".
```

Signed and Sealed this

Twenty-third Day of November, 1993

Attest:

BRUCE LEHMAN

Attesting Officer      Commissioner of Patents and Trademarks